(12) United States Patent
Shirotori et al.

(10) Patent No.: US 11,280,853 B2
(45) Date of Patent: Mar. 22, 2022

(54) MAGNETIC SENSOR, SENSOR MODULE, AND DIAGNOSTIC DEVICE

(71) Applicant: KABUSHIKI KAISHA TOSHIBA, Tokyo (JP)

(72) Inventors: Satoshi Shirotori, Yokohama Kanagawa (JP); Kenichiro Yamada, Minato Tokyo (JP); Yoshihiko Fuji, Kawasaki Kanagawa (JP); Yoshihiro Higashi, Komatsu Ishikawa (JP); Akira Kikitsu, Yokohama Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 73 days.

(21) Appl. No.: 16/814,060

(22) Filed: Mar. 10, 2020

(65) Prior Publication Data

US 2020/0319269 A1 Oct. 8, 2020

(30) Foreign Application Priority Data

Apr. 2, 2019 (JP) .............................. JP2019-070823
Feb. 17, 2020 (JP) .............................. JP2020-024215

(51) Int. Cl.
  *G01R 33/04* (2006.01)
  *G01R 33/00* (2006.01)
  *H01F 10/32* (2006.01)
(52) U.S. Cl.
  CPC ......... *G01R 33/04* (2013.01); *G01R 33/0052* (2013.01); *H01F 10/3259* (2013.01)
(58) Field of Classification Search
  CPC .... G01R 33/04; G01R 33/0052; G01R 33/09; H01F 10/3259

(Continued)

(56) References Cited

U.S. PATENT DOCUMENTS

| 7,375,516 B2 * | 5/2008 | Takenaga | ............... B82Y 25/00 324/207.11 |
| 2004/0029296 A1 * | 2/2004 | Tuttle | .................... H01L 27/222 438/3 |

(Continued)

FOREIGN PATENT DOCUMENTS

| JP | 2017-3336 A | 1/2017 |
| JP | 2018-155719 A | 10/2018 |
| JP | 2019-207167 A | 12/2019 |

OTHER PUBLICATIONS

Marinho et al., "Three dimensional magnetic flux concentrators with improved efficiency for magnetoresistive sensors," Journal of Applied Physics, 109:07E521-1 to 07E521-3 (2011).

(Continued)

*Primary Examiner* — Christopher E Mahoney
(74) *Attorney, Agent, or Firm* — Finnegan, Henderson, Farabow, Garrett & Dunner L.L.P

(57) ABSTRACT

According to one embodiment, a magnetic sensor includes a first element, a first wire, and a first magnetic part. The first element includes a first magnetic layer, a first counter magnetic layer, and a first nonmagnetic layer provided between the first magnetic layer and the first counter magnetic layer. A direction from the first counter magnetic layer toward the first magnetic layer is along a first direction. The first wire extends in a second direction crossing the first direction. The first magnetic part includes a first region and a first counter region. At least a portion of the first wire is between the first region and the first counter region in the first direction.

14 Claims, 26 Drawing Sheets

(58) Field of Classification Search
USPC .................. 324/252, 244, 251, 260, 207.21
See application file for complete search history.

(56) References Cited

U.S. PATENT DOCUMENTS

| | | | |
|---|---|---|---|
| 2013/0027031 A1* | 1/2013 | Dimitrov | G01R 33/093 324/252 |
| 2015/0022199 A1* | 1/2015 | Mito | G01R 15/207 324/252 |
| 2015/0247884 A1* | 9/2015 | Ogimoto | G01R 33/098 324/252 |
| 2018/0271395 A1 | 9/2018 | Iwasaki et al. | |
| 2019/0369172 A1 | 12/2019 | Kikitsu et al. | |

OTHER PUBLICATIONS

Valadeiro et al., "Improved Efficiency of Tapered magnetic Flux Concentrators With Double-Layer Architecture," IEEE Transactions On Magnetics vol. 53, No. 11 (Nov. 2017), 5 pages.
Fujiwara et al., "Magnetocardiography and magnetoencephalography measurements at room temperature using tunnel magneto-resistance sensors," Applied Physics Express, 11:023001-1 to 023001-4 (2018).

\* cited by examiner

MAGNETIC SENSOR, SENSOR MODULE, AND DIAGNOSTIC DEVICE

CROSS-REFERENCE TO RELATED APPLICATIONS

This application is based upon and claims the benefit of priority from Japanese Patent Application No. 2019-070823, filed on Apr. 2, 2019, and Japanese Patent Application No. 2020-24215, filed on Feb. 17, 2020; the entire contents of which are incorporated herein by reference.

FIELD

Embodiments described herein relate generally to a magnetic sensor, a sensor module, and a diagnostic device.

BACKGROUND

There is a magnetic sensor using a magnetic layer. There is a diagnostic device using the magnetic sensor. It is desirable to increase the detection sensitivity of the magnetic sensor.

DETAILED DESCRIPTION

Figure 1A:
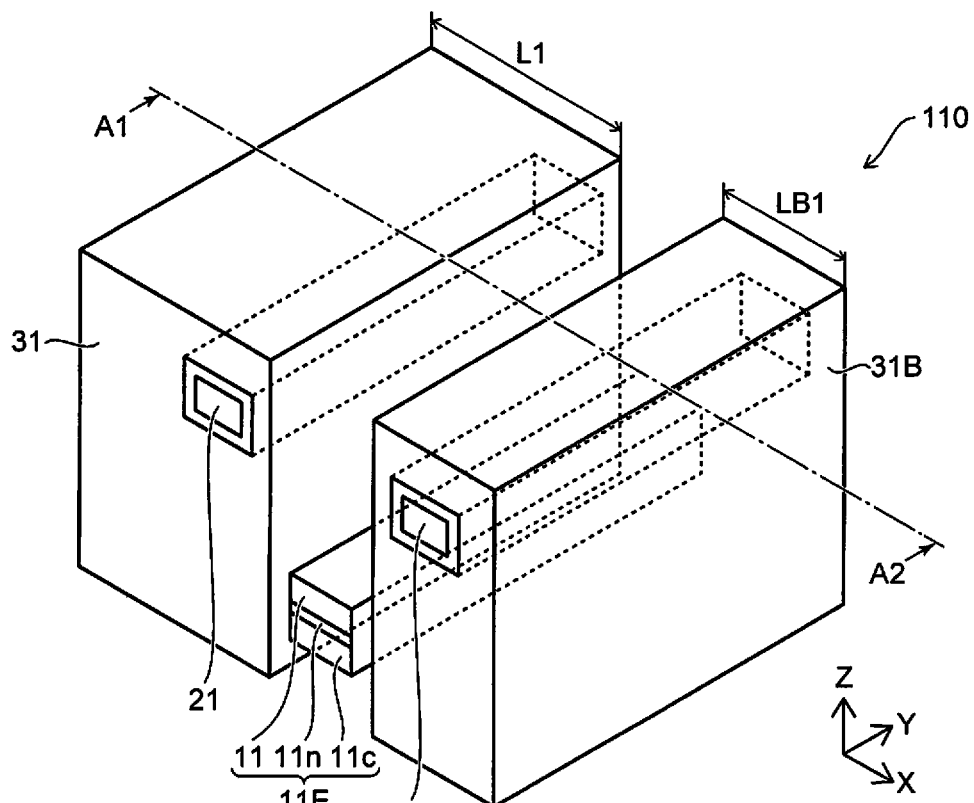
FIG. 1A and FIG. 1B are schematic views illustrating a magnetic sensor according to a first embodiment.

According to one embodiment, a magnetic sensor includes a first element, a first wire, and a first magnetic part. The first element includes a first magnetic layer, a first counter magnetic layer, and a first nonmagnetic layer provided between the first magnetic layer and the first counter magnetic layer. A direction from the first counter magnetic layer toward the first magnetic layer is along a first direction. The first wire extends in a second direction crossing the first direction. The first magnetic part includes a first region and a first counter region. At least a portion of the first wire is between the first region and the first counter region in the first direction.

According to one embodiment, a magnetic sensor includes a first element, a first wire, a first counter wire, and a first magnetic part. The first element includes a first magnetic layer, a first counter magnetic layer, and a first nonmagnetic layer provided between the first magnetic layer and the first counter magnetic layer. A direction from the first counter magnetic layer toward the first magnetic layer is along a first direction. The first wire extends in a second direction crossing the first direction. The first counter wire extends in the second direction. The first magnetic part is provided between the first wire and the first counter wire in the first direction.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
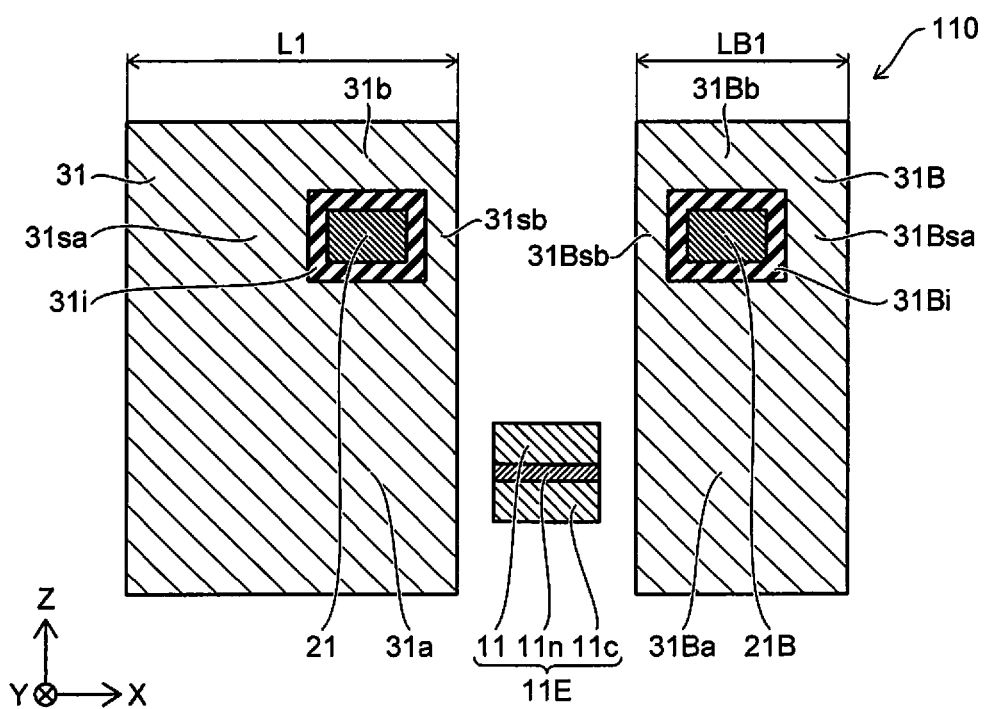

FIG. 1A and FIG. 1B are schematic views illustrating a magnetic sensor according to a first embodiment.

FIG. 1A is a perspective view. FIG. 1B is a line A1-A2 cross-sectional view of FIG. 1A.

As shown in FIG. 1A, the magnetic sensor 110 according to the embodiment includes a first element 11E, a first wire 21, and a first magnetic part 31.

The first element 11E includes a first magnetic layer 11, a first counter magnetic layer 11c, and a first nonmagnetic layer 11n. The first nonmagnetic layer 11n is provided between the first magnetic layer 11 and the first counter magnetic layer 11c.

The first nonmagnetic layer 11n is, for example, conductive. In such a case, the first nonmagnetic layer 11n includes Cu, etc. In such a case, the first element 11E functions as a GMR element. For example, the first nonmagnetic layer 11n may be insulative. In such a case, the first nonmagnetic layer 11n includes MgO, etc. In such a case, the first element 11E functions as a TMR element.

The direction from the first counter magnetic layer 11c toward the first magnetic layer 11 is along a first direction. The first direction is taken as a Z-axis direction. One direction perpendicular to the Z-axis direction is taken as an X-axis direction. A direction perpendicular to the Z-axis direction and the X-axis direction is taken as a Y-axis direction.

The first wire 21 extends in a second direction. The second direction crosses the first direction (the Z-axis direction). The second direction is, for example, the Y-axis direction.

The length along the Y-axis direction of the first wire 21 is longer than the length along the Z-axis direction of the first wire 21. The length along the Y-axis direction of the first wire 21 is longer than the length along the X-axis direction of the first wire 21.

The first magnetic part 31 includes a first region 31a and a first counter region 31b. At least a portion of the first wire 21 is between the first region 31a and the first counter region 31b in the first direction (the Z-axis direction).

A magnetic field which is the measurement object is applied to the first element 11E. The electrical resistance of the first element 11E changes according to the magnetic field. For example, the angle between the magnetization of the first magnetic layer 11 and the magnetization of the first counter magnetic layer 11c changes due to the applied magnetic field. The electrical resistance changes due to the change of the angle. For example, the change of the electrical resistance is based on a magnetoresistance effect.

In the embodiment as described below, an alternating current is supplied to the first wire 21. An alternating-current magnetic field is generated from the first wire 21 by the alternating current. The magnetic field which is the measurement object and the alternating-current magnetic field are applied to the first element 11E. The electrical resistance of the first element 11E is modulated by these two types of magnetic fields. The magnetic field which is the measurement object is detected by detecting an electrical signal corresponding to the modulated electrical resistance and by performing appropriate processing.

For example, the first magnetic part 31 functions as a MFC (Magnetic Flux Concentrator). The first magnetic part 31 includes, for example, at least one selected from the group consisting of a NiFe alloy, an FeCo alloy, and a CoZrNb alloy. The first magnetic part 31 includes, for example, an amorphous alloy. The first magnetic part 31 includes, for example, a material having a high permeability. The first magnetic part 31 includes, for example, a soft magnetic material. For example, the magnetic field from the outside concentrates easily in the region of the first element 11E due to the high permeability.

In the embodiment, at least a portion of the first wire 21 is between the first region 31a and the first counter region 31b. Thereby, the alternating-current magnetic field that is generated when the alternating current flows in the first wire 21 is confined easily inside the first magnetic part 31. The alternating-current magnetic field is applied efficiently to the first element 11E. The detection sensitivity can be increased thereby. According to the embodiment, a magnetic sensor can be provided in which the detection sensitivity can be increased.

In the embodiment, it is favorable for the distance (e.g., the distance along the X-axis direction) between the first magnetic part 31 and the first element 11E to be, for example, not more than $1/1000$ times the length (e.g., the width) along the third direction (the X-axis direction) of the first magnetic part 31. Thereby, the magnetic field from the first magnetic part 31 easily is applied efficiently to the first element 11E.

As shown in FIG. 1B, an insulating region 31i may be provided between the first wire 21 and the first magnetic part 31.

In the example as shown in FIG. 1B, the third direction from the first region 31a toward the first element 11E crosses a plane (the Z-Y plane) including the first direction and the second direction. The third direction is, for example, the X-axis direction.

In the embodiment, the direction from the first region 31a toward the first element 11E may be along the first direction (the Z-axis direction).

In the example, the first magnetic part 31 further includes a first side region 31sa and a first counter side region 31sb. At least a portion of the first wire 21 is between the first side region 31sa and the first counter side region 31sb in the third direction (the X-axis direction). In the example, the first region 31a, the first counter region 31b, the first side region 31sa, and the first counter side region 31sb are continuous with each other. As described below, a portion of these regions may be divided by an insulating region, etc.

In the example as shown in FIG. 1A and FIG. 1B, the magnetic sensor 110 further includes a first side wire 21B and a first side magnetic part 31B.

The first side magnetic part 31B includes in a first region 31Ba of the first side magnetic part 31B and a first counter region 31Bb of the first side magnetic part 31B. At least a portion of the first side wire 21B is between the first region 31Ba of the first side magnetic part 31B and the first counter region 31Bb of the first side magnetic part 31B in the first direction (the Z-axis direction).

In the example, the position in the third direction (the X-axis direction) of the first element 11E is between the position in the third direction of the first wire 21 and the position in the third direction of the first side wire 21B.

As described below, the first wire 21 and the first side wire 21B are electrically connected in parallel to each other. For example, the currents that flow in the first wire 21 and the first side wire 21B have the same orientation. The magnetic field that is generated from the first wire 21 and the magnetic field that is generated from the first side wire 21B have the same orientation at the position of the first element 11E.

These magnetic fields are applied efficiently to the first element 11E. Higher detection sensitivity is obtained thereby.

In the example as described above, the first magnetic part 31 includes the first side region 31sa of the first magnetic part 31 and the first counter side region 31sb of the first magnetic part 31. At least a portion of the first wire 21 is between the first side region 31sa of the first magnetic part 31 and the first counter side region 31sb of the first magnetic part 31 in the third direction (the X-axis direction).

The first side magnetic part 31B includes a first side region 31Bsa of the first side magnetic part 31B and a first counter side region 31Bsb of the first side magnetic part 31B. At least a portion of the first side wire 21B is between the first side region 31Bsa of the first side magnetic part 31B and the first counter side region 31Bsb of the first side magnetic part 31B in the third direction (the X-axis direction).

The position in the third direction (the X-axis direction) of the first counter side region 31sb of the first magnetic part 31 is between the position in the third direction of the first side region 31sa of the first magnetic part 31 and the position in the third direction of the first side region 31Bsa of the first side magnetic part 31B.

The position in the third direction (the X-axis direction) of the first counter side region 31Bsb of the first side magnetic part 31B is between the position in the third direction of the first counter side region 31sb of the first magnetic part 31 and the position in the third direction of the first side region 31Bsa of the first side magnetic part 31B.

For example, such a configuration functions as one sensor part.

As shown in FIG. 1A and FIG. 1B, the length along the third direction (the X-axis direction) of the first magnetic part 31 is taken as a length L1. The length along the third direction (the X-axis direction) of the first side magnetic part 31B is taken as a length LB1. These lengths may be different from each other. For example, the length L1 along the third direction of the first magnetic part 31 is longer than the length LB1 along the third direction of the first side magnetic part 31B.

For example, a plurality of the configurations (the one sensor parts) including the first element 11E, the first wire 21, the first side wire 21B, the first magnetic part 31, and the first side magnetic part 31B may be provided. In such a case, the widths of the magnetic parts provided in the region between two elements in the X-axis direction may be less than the widths of the magnetic parts provided in the regions outward of the two elements. The size of the entire magnetic sensor is reduced easily thereby.

As shown in FIG. 1B, an insulating region 31Bi may be provided between the first side wire 21B and the first side magnetic part 31B.

An example of the current supplied to the magnetic sensor 110 will now be described.

Figure 2:
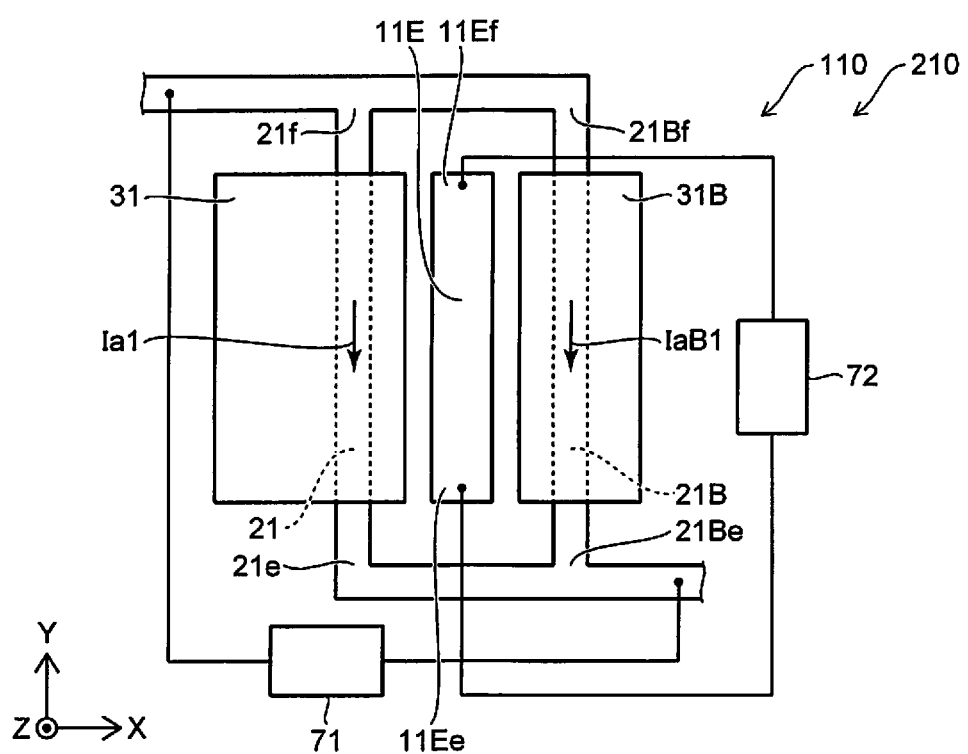
FIG. 2 is a schematic plan view illustrating the magnetic sensor according to the first embodiment.

FIG. 2 is a schematic plan view illustrating the magnetic sensor according to the first embodiment.

As shown in FIG. 2, the magnetic sensor 110 may further include a first circuit 71.

The first wire 21 includes a first end portion 21e of the first wire 21 and a first other end portion 21f of the first wire 21. The direction from the first end portion 21e of the first wire 21 toward the first other end portion 21f of the first wire 21 is along the second direction (the Y-axis direction).

The first side wire 21B includes a first end portion 21Be of the first side wire 21B and a first other end portion 21Bf of the first side wire 21B. The direction from the first end portion 21Be of the first side wire 21B toward the first other end portion 21Bf of the first side wire 21B is along the second direction (the Y-axis direction).

The direction from the first end portion 21e of the first wire 21 toward the first end portion 21Be of the first side wire 21B is along the third direction (the X-axis direction). The direction from the first other end portion 21f of the first wire 21 toward the first other end portion 21Bf of the first side wire 21B is along the third direction (the X-axis direction).

The first end portion 21e of the first wire 21 and the first end portion 21Be of the first side wire 21B are electrically connected to each other. The first other end portion 21f of the first wire 21 and the first other end portion 21Bf of the first side wire 21B are electrically connected to each other. Thus, the first wire 21 and the first side wire 21B are connected in parallel to each other.

The first circuit 71 is electrically connected to the first end portion 21e of the first wire 21 (and the first end portion 21Be of the first side wire 21B) and the first other end portion 21f of the first wire 21 (and the first other end portion 21Bf of the first side wire 21B). The first circuit 71 supplies an alternating current (an alternating current Ia1 and an alternating current IaB1) to the first wire 21 and the first side wire 21B.

For example, the alternating current IaB1 flows from the first other end portion 21Bf of the first side wire 21B toward the first end portion 21Be of the first side wire 21B when the alternating current Ia1 flows from the first other end portion 21f of the first wire 21 toward the first end portion 21e of the first wire 21.

The magnetic sensor 110 may further include a second circuit 72. The second circuit 72 is electrically connected to the first element 11E. For example, the second circuit 72 is electrically connected to a first end portion 11Ee of the first element 11E and a first other end portion 11Ef of the first element 11E. In the first element 11E of the example, a direct current flows between the first end portion 11Ee and the first other end portion 11Ef. In such a case, the first element 11E is a current-in-plane element.

In the embodiment, the current that flows through the first element 11E may flow along the Z-axis direction. In such a case, the first element 11E is a current-perpendicular-to-plane element.

For example, the second circuit 72 may detect a value corresponding to the change of a value (an electrical resistance, a voltage, a current, etc.) corresponding to the electrical resistance of the first element 11E.

Figure 3:
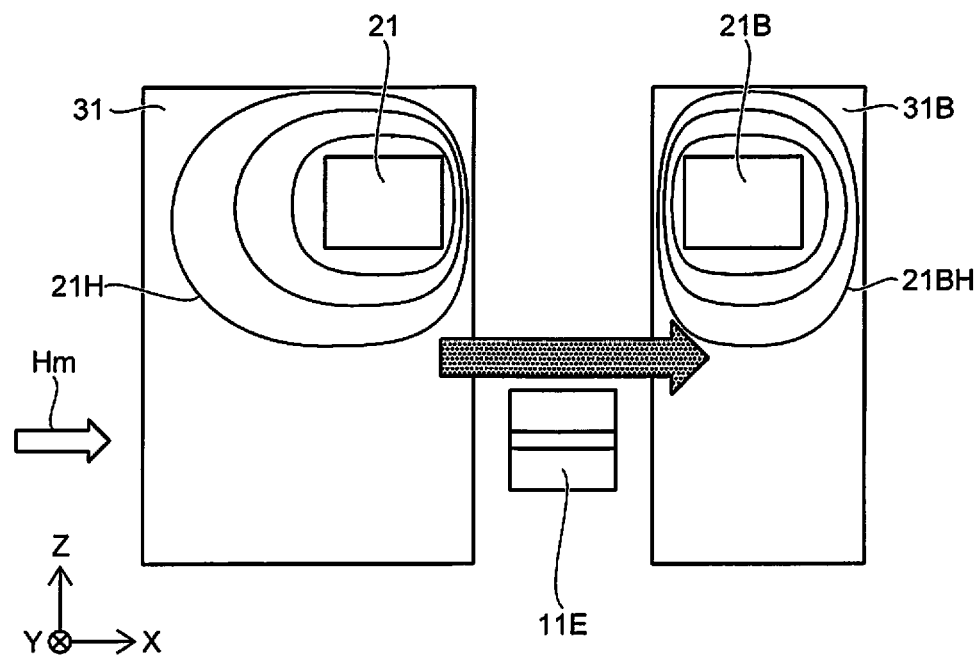
FIG. 3 is a schematic cross-sectional view illustrating an operation of the magnetic sensor according to the first embodiment.

FIG. 3 is a schematic cross-sectional view illustrating an operation of the magnetic sensor according to the first embodiment.

As shown in FIG. 3, a magnetic flux 21H is generated when the current flows in the first wire 21. A magnetic flux 21BH is generated when the current flows in the first side wire 21B. The magnetic flux 21H is substantially confined inside the first magnetic part 31. The magnetic flux 21BH is substantially confined inside the first side magnetic part 31B. The magnetic flux 21H and the magnetic flux 21BH are applied efficiently to the first element 11E in the region between the first magnetic part 31 and the first side magnetic part 31B.

Also, a magnetic field Hm from the outside which is the detection object is concentrated and applied efficiently to the first element 11E by the first magnetic part 31 and the first side magnetic part 31B.

Thereby, in the first element 11E, a large change of the electrical resistance occurs corresponding to the alternating current flowing in the first wire 21 and the alternating current flowing in the first side wire 21B. Also, a large change of the electrical resistance occurs corresponding to the magnetic field Hm from the outside which is the detection object. High detection sensitivity is obtained thereby.

A sensor module 210 according to the embodiment (referring to FIG. 2) includes, for example, the magnetic sensor 110 and the first circuit 71. The sensor module 210 may include the second circuit 72.

Figure 4:
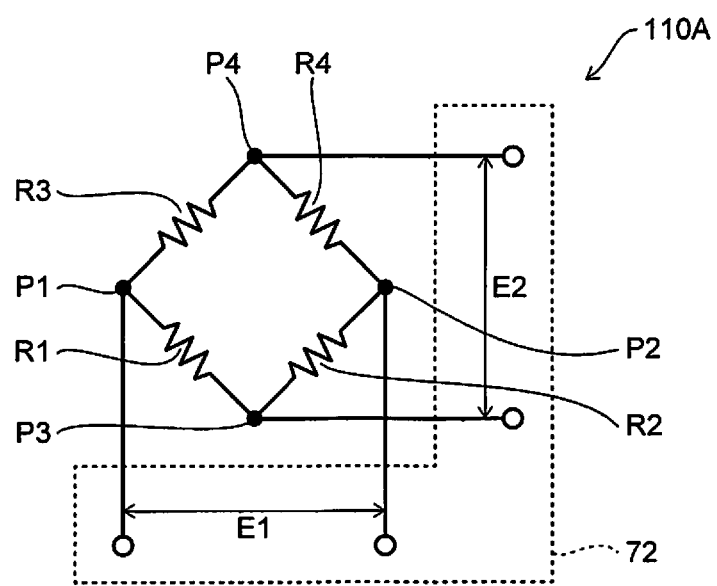
FIG. 4 is a schematic view illustrating a magnetic sensor according to the first embodiment.

FIG. 4 is a schematic view illustrating a magnetic sensor according to the first embodiment.

As shown in FIG. 4, the magnetic sensor 110A according to the embodiment includes first to fourth resistance parts R1 to R4. For example, one end of the first resistance part R1 is connected to one end of the second resistance part R2. The other end of the first resistance part R1 is connected to one end of the third resistance part R3. The other end of the second resistance part R2 is connected to one end of the fourth resistance part R4. The other end of the third resistance part R3 is connected to the other end of the fourth resistance part R4.

For example, the connection point between the other end of the first resistance part R1 and the one end of the third resistance part R3 is taken as a first connection point P1. The connection point between the other end of the second resistance part R2 and the one end of the fourth resistance part R4 is taken as a second connection point P2. The connection point between the one end of the first resistance part R1 and the one end of the second resistance part R2 is taken as a third connection point P3. The connection point between the other end of the third resistance part R3 and the other end of the fourth resistance part R4 is taken as a fourth connection point P4.

For example, a voltage E1 is applied between the first connection point P1 and the second connection point P2. At this time, a voltage E2 between the third connection point P3 and the fourth connection point P4 is detected. For example, the application of the voltage E1 and the detection of the voltage E2 are performed by the second circuit 72. The magnetic sensor 110A includes, for example, a bridge circuit.

In the magnetic sensor 110A, an element that includes the first element 11E, the first wire 21, and the first magnetic part 31 is used as any of the first to fourth resistance parts R1 to R4. For example, the first element 11E is used as the first resistance part R1 recited above. The first end portion 11Ee of the first element 11E corresponds to the one end of the first resistance part R1. The first other end portion 11Ef of the first element 11E corresponds to the other end of the first resistance part R1.

For example, higher detection sensitivity is obtained by the magnetic sensor 110A including the bridge circuit.

In one example, the second to fourth resistance parts R2 to R4 each include the first element 11E and the first wire 21 but do not include the first magnetic part 31 when the first resistance part R1 includes the first element 11E, the first wire 21, and the first magnetic part 31. A MFC is not provided in such second to fourth resistance parts R2 to R4. For example, the magnetic field which is the detection object applied to the second to fourth resistance parts R2 to R4 is not more than about 1/100 of the magnetic field applied to the first resistance part R1. In such a case, the second to fourth resistance parts R2 to R4 can be considered to be resistors.

Multiple such sensor parts may be provided. An example of a sensor part including a second element will now be described.

Figure 5A:
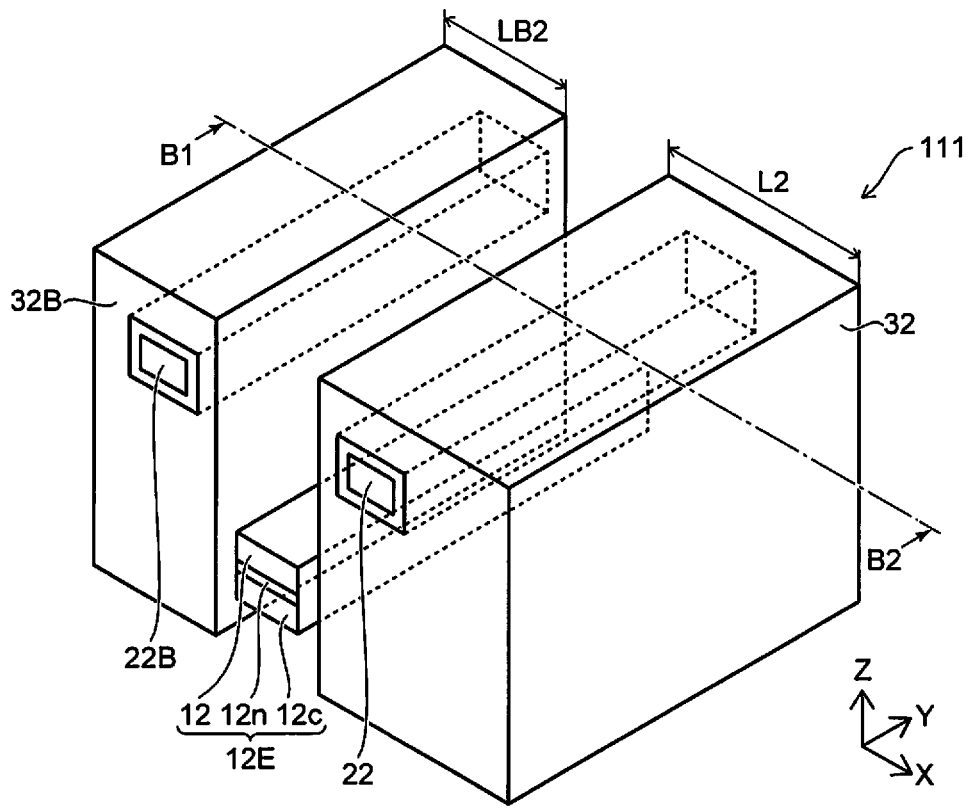
FIG. 5A and FIG. 5B are schematic views illustrating a portion of a magnetic sensor according to the first embodiment.
Figure 5B:
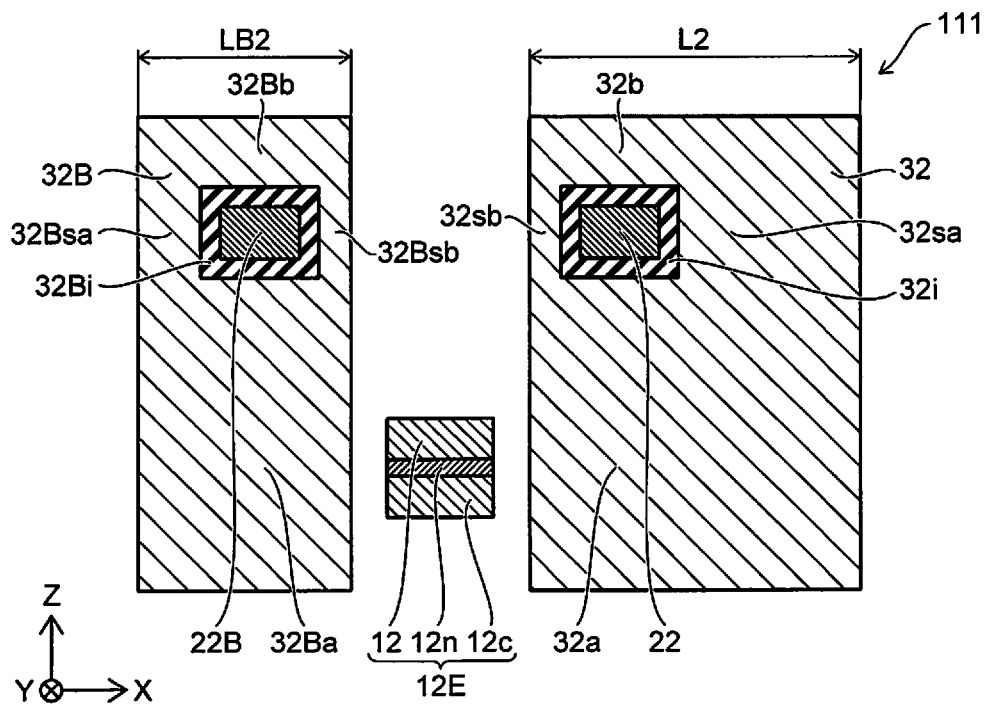

FIG. 5A and FIG. 5B are schematic views illustrating a portion of the magnetic sensor according to the first embodiment.

FIG. 5A is a perspective view. FIG. 5B is a line B1-B2 cross-sectional view of FIG. 5A.

As shown in FIG. 5A, the magnetic sensor 111 according to the embodiment further includes a second element 12E, a second wire 22, and a second magnetic part 32 in addition to the first element 11E, the first wire 21, and the first magnetic part 31 (referring to FIG. 1A). The configurations described above are applied to the first element 11E, the first wire 21, and the first magnetic part 31; and a description is therefore omitted.

As shown in FIG. 5A, the second element 12E includes a second magnetic layer 12, a second counter magnetic layer 12c, and a second nonmagnetic layer 12n. The second nonmagnetic layer 12n is provided between the second magnetic layer 12 and the second counter magnetic layer 12c. The direction from the second counter magnetic layer 12c toward the second magnetic layer 12 is along the first direction (the Z-axis direction).

The second wire 22 extends in the second direction (the Y-axis direction). The second magnetic part 32 includes a second region 32a and a second counter region 32b. At least a portion of the second wire 22 is between the second region 32a and the second counter region 32b in the first direction (the Z-axis direction).

A magnetic field that is generated by a current flowing through the second wire 22 is applied efficiently to the second element 12E. High detection sensitivity is obtained thereby.

In the example, the direction from the second element 12E toward the second region 32a is along the third direction (the X-axis direction).

In the example, the second magnetic part 32 further includes a second side region 32sa and a second counter side region 32sb. At least a portion of the second wire 22 is between the second side region 32sa and the second counter side region 32sb in the third direction (the X-axis direction).

A second side wire 22B and a second side magnetic part 32B are provided in the example. The second side wire 22B extends in the second direction (the Y-axis direction). The second side magnetic part 32B includes a second region 32Ba of the second side magnetic part 32B and a second counter region 32Bb of the second side magnetic part 32B. At least a portion of the second side wire 22B is between the second region 32Ba of the second side magnetic part 32B and the second counter region 32Bb of the second side magnetic part 32B in the first direction (the Z-axis direction).

The position in the third direction (the X-axis direction) of the second element 12E is between the position in the third direction of the second wire 22 and the position in the third direction of the second side wire 22B.

For example, the second side magnetic part 32B further includes a second side region 32Bsa of the second side magnetic part 32B and a second counter side region 32Bsb of the second side magnetic part 32B.

At least a portion of the second side wire 22B is between the second side region 32Bsa of the second side magnetic part 32B and the second counter side region 32Bsb of the second side magnetic part 32B in the third direction (the X-axis direction).

The position in the third direction (the X-axis direction) of the second counter side region 32sb of the second magnetic part 32 is between the position in the third direction of the second side region 32sa of the second magnetic part 32 and the position in the third direction of the second side region 32Bsa of the second side magnetic part 32B.

The position in the third direction (the X-axis direction) of the second counter side region 32Bsb of the second side magnetic part 32B is between the position in the third direction of the second counter side region 32sb of the second magnetic part 32 and the position in the third direction of the second side region 32Bsa of the second side magnetic part 32B.

In the example as well, the length along the X-axis direction of the second magnetic part 32 may be different from the length along the X-axis direction of the second side magnetic part 32B. For example, a length L2 along the third direction (the X-axis direction) of the second magnetic part 32 may be longer than a length LB2 along the third direction of the second side magnetic part 32B.

Thereby, for example, the distance (the distance along the X-axis direction) between the first element 11E and the second element 12E can be short. For example, the size of the magnetic sensor 111 can be small.

As shown in FIG. 5B, an insulating region 32i may be provided between the second wire 22 and the second magnetic part 32. An insulating region 32Bi may be provided between the second side wire 22B and the second side magnetic part 32B.

Figure 6A:
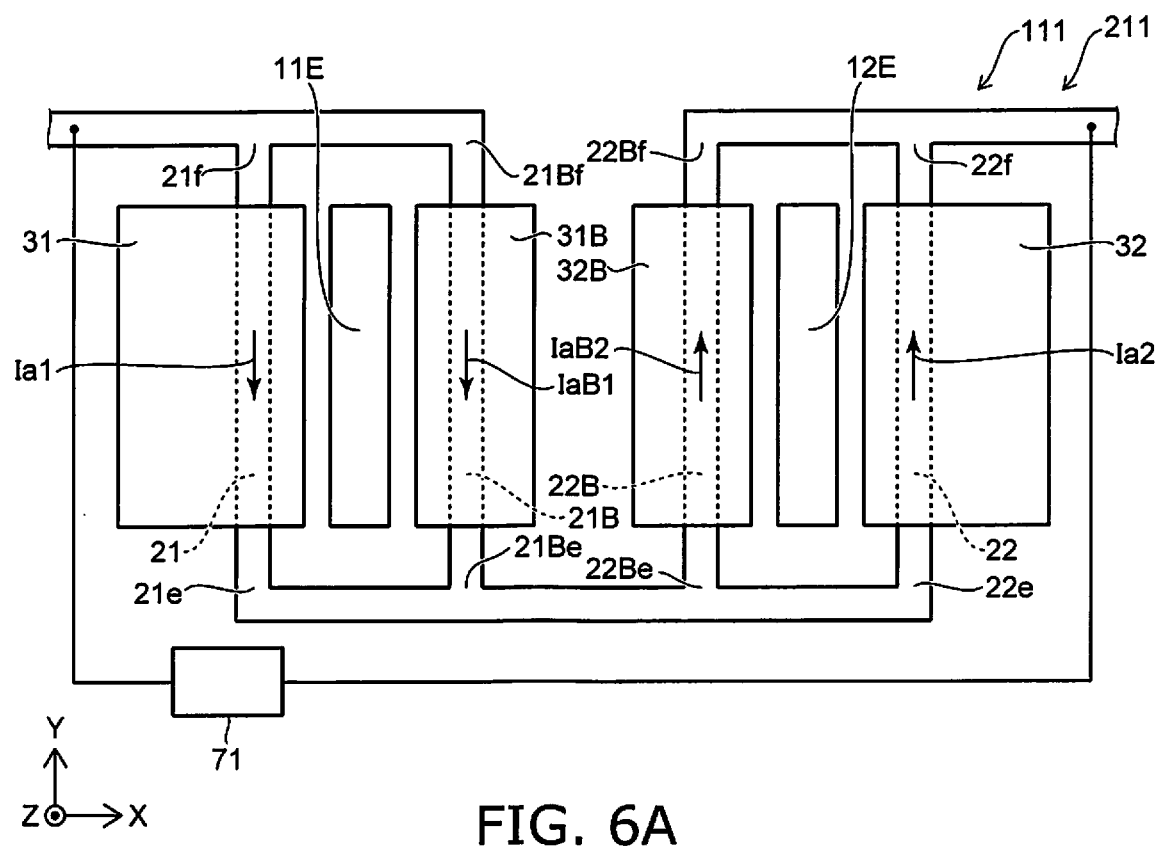
FIG. 6A and FIG. 6B are schematic plan views illustrating the magnetic sensor according to the first embodiment.
Figure 6B:
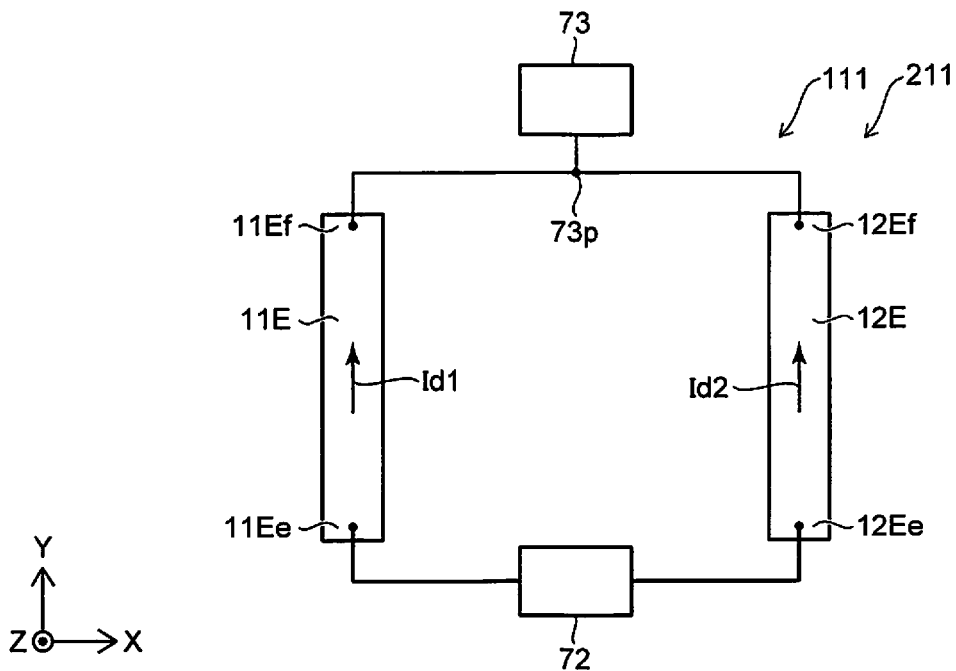

FIG. 6A and FIG. 6B are schematic plan views illustrating the magnetic sensor according to the first embodiment.

As shown in FIG. 6A, for example, the first side wire 21B is provided between the first wire 21 and the second wire 22 in the X-axis direction. For example, the second side wire 22B is provided between the first side wire 21B and the second wire 22 in the X-axis direction.

The first wire 21 includes the first end portion 21e of the first wire 21 and the first other end portion 21f of the first wire 21. The direction from the first end portion 21e of the first wire 21 toward the first other end portion 21f of the first wire 21 is along the second direction (the Y-axis direction).

The first side wire 21B includes the first end portion 21Be of the first side wire 21B and the first other end portion 21Bf of the first side wire 21B. The direction from the first end portion 21Be of the first side wire 21B toward the first other end portion 21Bf of the first side wire 21B is along the second direction (the Y-axis direction).

The direction from the first end portion 21e of the first wire 21 toward the first end portion 21Be of the first side wire 21B is along the third direction (the X-axis direction). The direction from the first other end portion 21f of the first wire 21 toward the first other end portion 21Bf of the first side wire 21B is along the third direction (the X-axis direction). The first end portion 21e of the first wire 21 and the first end portion 21Be of the first side wire 21B are electrically connected to each other. The first other end portion 21f of the first wire 21 and the first other end portion 21Bf of the first side wire 21B are electrically connected to each other.

The second wire 22 includes a second end portion 22e of the second wire 22 and a second other end portion 22f of the second wire 22. The direction from the second end portion 22e of the second wire 22 toward the second other end portion 22f of the second wire 22 is along the second direction (the Y-axis direction).

The second side wire 22B includes a second end portion 22Be of the second side wire 22B and a second other end portion 22Bf of the second side wire 22B. The direction from the second end portion 22Be of the second side wire 22B toward the second other end portion 22Bf of the second side wire 22B is along the second direction (the Y-axis direction).

The direction from the second end portion 22Be of the second side wire 22B toward the second end portion 22e of the second wire 22 is along the third direction (the X-axis direction). The direction from the second other end portion 22Bf of the second side wire 22B toward the second other end portion 22f of the second wire 22 is along the third direction (the X-axis direction). The second end portion 22e of the second wire 22 and the second end portion 22Be of the second side wire 22B are electrically connected to each other. The second other end portion 22f of the second wire 22 and the second other end portion 22Bf of the second side wire 22B are electrically connected to each other.

The second end portion 22e of the second wire 22 is electrically connected to the first end portion 21e of the first wire 21.

The first circuit 71 is electrically connected to the first other end portion 21f of the first wire 21 and the second other end portion 22f of the second wire 22. The first circuit 71 supplies an alternating current to the first wire 21, the first side wire 21B, the second wire 22, and the second side wire 22B.

For example, the first circuit 71 supplies the alternating current Ia1 to the first wire 21. The first circuit 71 supplies the alternating current IaB1 to the first side wire 21B. The first circuit 71 supplies an alternating current Ia2 to the second wire 22. The first circuit 71 supplies an alternating current IaB2 to the second side wire 22B. For example, the frequencies of these alternating currents are substantially the same.

The orientation of the alternating current IaB1 is the same as the orientation of the alternating current Ia1. The orientation of the alternating current IaB2 is the same as the orientation of the alternating current Ia2. The orientation of the alternating current Ia2 is the reverse of the orientation of the alternating current Ia1.

As shown in FIG. 6A, for example, the first element 11E is provided between the first wire 21 and the first side wire 21B in the X-axis direction. For example, the second element 12E is provided between the second side wire 22B and the second wire 22 in the X-axis direction.

As shown in FIG. 6B, the first element 11E includes the first end portion 11Ee and the first other end portion 11Ef. The direction from the first end portion 11Ee toward the first other end portion 11Ef is along the Y-axis direction. The second element 12E includes a second end portion 12Ee and a second other end portion 12Ef. The direction from the second end portion 12Ee toward the second other end portion 12Ef is along the Y-axis direction.

For example, the direction from the first end portion 11Ee toward the second end portion 12Ee is along the X-axis direction. The direction from the first other end portion 11Ef toward the second other end portion 12Ef is along the X-axis direction.

For example, the second circuit 72 is electrically connected to the first element 11E and the second element 12E. For example, the second circuit 72 is electrically connected to the first end portion 11Ee and electrically connected to the second end portion 12Ee. The first other end portion 11Ef is electrically connected to the second other end portion 12Ef. In the example, the first element 11E and the second element 12E are electrically connected in series to each other.

For example, the second circuit 72 supplies a current Id1 to the first element 11E. The second circuit 72 supplies a current Id2 to the second element 12E. For example, the second circuit 72 applies a direct current voltage to the first element 11E and the second element 12E.

A third circuit 73 is provided in the example. The third circuit 73 detects the potential of a connection point 73p between the first element 11E and the second element 12E.

For example, the magnetic field Hm from the outside which is the detection object is applied to the magnetic sensor 111. The potential of the connection point 73p changes according to the magnetic field Hm from the outside when the alternating current is supplied to the first wire 21, the first side wire 21B, the second wire 22, and the second side wire 22B. The magnetic field Hm from the outside which is the detection object can be detected by detecting the potential of the connection point 73p.

An example of the change of the electrical resistance due to the magnetic field Hm from the outside will now be described. Characteristics of the first element 11E will be described. The description that relates to the first element 11E is applicable also to the second element 12E.

For example, a magnetic field is applied to the first element 11E. The magnetic field includes, for example, a component along the X-axis direction. The electrical resistance of the first element 11E has an even-function characteristic of the magnetic field.

Figure 7:
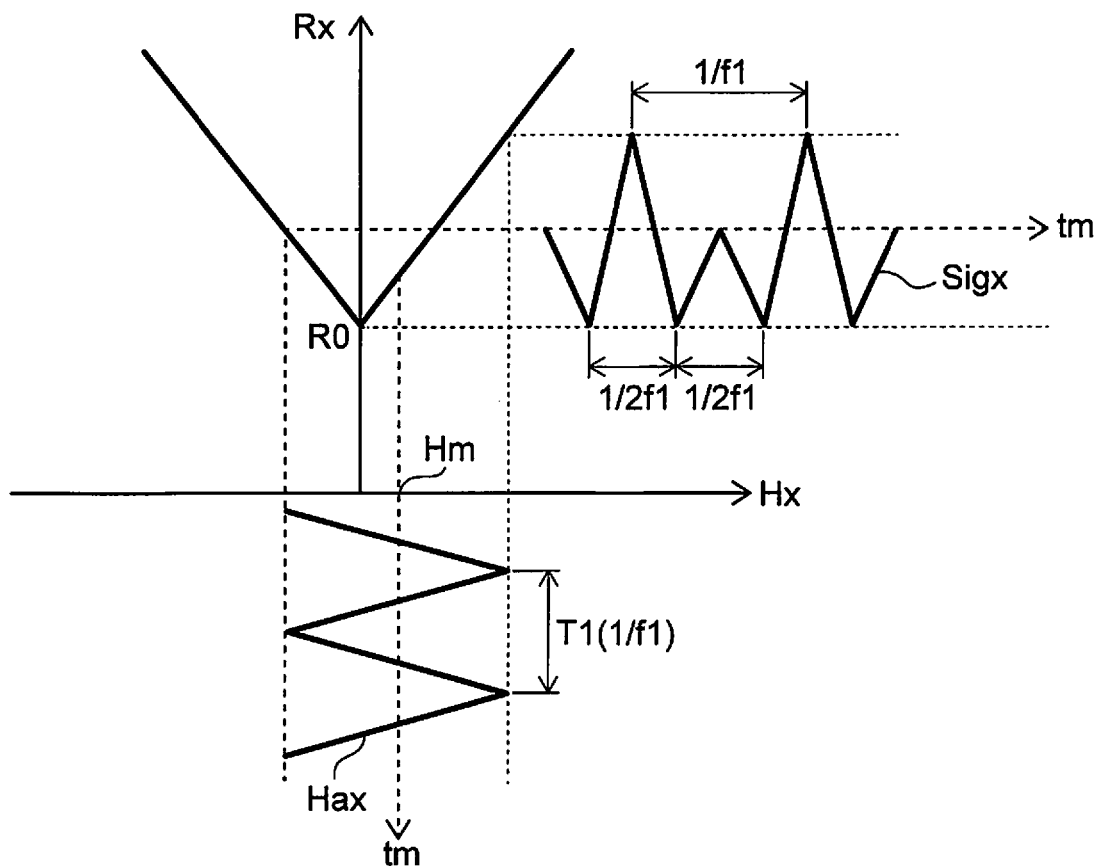
FIG. 7 is a graph illustrating the characteristics of the magnetic sensor.

FIG. 7 is a graph illustrating the characteristics of the magnetic sensor.

FIG. 7 illustrates the characteristics when an alternating-current magnetic field Hax and the magnetic field Hm are applied as a magnetic field Hx to the first element 11E. The magnetic field Hm is the magnetic field of the measurement object (the detection object). The horizontal axis corresponds to the magnetic field Hx. The vertical axis corresponds to an electrical resistance Rx of the first element 11E. In the example of FIG. 7, the alternating-current magnetic field Hax is a triangular wave. The alternating-current magnetic field Hax may be a sine wave, a pulse wave, etc. The frequency of the alternating-current magnetic field Hax is taken as a first frequency f1. The reciprocal of the first frequency f1 corresponds to a first period T1. As shown in FIG. 7, the alternating-current magnetic field Hax changes with a time tm.

As shown in FIG. 7, for example, a signal Sigx is obtained from the first element 11E when the alternating-current magnetic field Hax and the magnetic field Hm are applied. The signal Sigx corresponds to the change of the electrical resistance Rx. In the signal Sigx, a waveform that has two types of frequency components referenced to an electrical resistance R0 is obtained.

The signal Sigx (the electrical resistance Rx) has a frequency component of the first frequency f1 and a component of a double frequency 2f1. The waveform component that corresponds to the frequency of the first frequency f1 is caused by the magnetic field Hm. In the case where the magnetic field Hm is 0, peaks that correspond to the frequency of the first frequency f1 substantially are not generated; and the component of the double frequency 2f1 is generated. For example, the component that corresponds to the frequency of the first frequency f1 can be extracted using a filter, etc. The magnetic field Hm which is the detection object can be known by measuring the intensity of the peak corresponding to the frequency of the first frequency f1. The signal of the double frequency 2f1 is, for example, an unnecessary signal (e.g., noise).

The magnetic field Hm may be a direct-current magnetic field or an alternating-current magnetic field. In the case where the magnetic field Hm is an alternating-current magnetic field, the frequency of the magnetic field Hm is lower than the frequency (the first frequency f1) of the alternating-current magnetic field Hax.

FIG. 7 illustrates the case where one alternating-current magnetic field Hax is applied to one element (the first element 11E). In the embodiment, for example, a first alternating-current magnetic field is applied to the first element 11E based on the alternating current flowing in the first wire 21, etc. A second alternating-current magnetic field is applied to the second element 12E based on the alternating current flowing in the second wire 22, etc.

Figure 8:
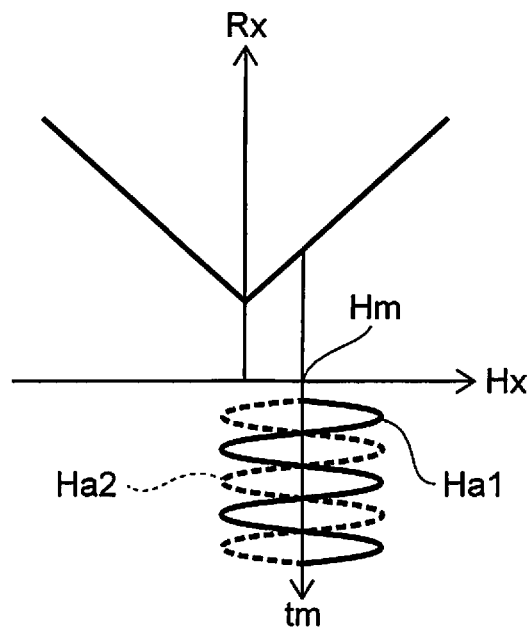
FIG. 8 is a graph illustrating a characteristic of the magnetic sensor.

FIG. 8 is a graph illustrating a characteristic of the magnetic sensor.

The horizontal axis of FIG. 8 corresponds to the magnetic field Hx. The vertical axis of FIG. 8 corresponds to the electrical resistance Rx. As illustrated in FIG. 8, the phases are mutually-reversed for the first alternating-current magnetic field Ha1 applied to the first element 11E and the second alternating-current magnetic field Ha2 applied to the second element 12E.

The two types of signals Sigx corresponding respectively to the first alternating-current magnetic field Ha1 and the second alternating-current magnetic field Ha2 are generated (referring to FIG. 7). The phases are shifted by a period of "1/2f1" between the two types of signals Sigx. Therefore, for example, in the composite signal of the two types of signals Sigx, the components of the double frequency 2f1 substantially cancel. A signal that corresponds to the frequency of the first frequency f1 remains. The magnetic field Hm which is the detection object can be known by measuring the strength of the signal (e.g., the peak) corresponding to the frequency of the first frequency f1. By using such alternating-current magnetic fields having reverse phases, the component of the double frequency 2f1 (e.g., the unnecessary signal) can be suppressed. According to the embodiment, a magnetic sensor can be provided in which the detection sensitivity can be increased.

For example, a signal that corresponds to the change of the potential of the connection point 73p between the first element 11E and the second element 12E illustrated in FIG. 6B is detected. Information that relates to the magnetic field Hm which is the detection object is obtained by measuring the signal strength of this signal corresponding to the frequency of the first frequency f1. For example, in the signal at the connection point 73p, the signal strength corresponding to the double frequency 2f1 is smaller than the signal strength corresponding to the frequency of the first frequency f1. In such a signal, a component that corresponds to the double frequency 2f1 substantially is not generated.

In the embodiment, a component that corresponds to the double frequency 2f1 may be generated by fluctuation of the characteristics of the multiple elements (the first element 11E and the second element 12E), the characteristics of the wires electrically connected to these elements, etc. The unnecessary signal can be suppressed by markedly reducing the component corresponding to the double frequency 2f1. The detection sensitivity can be increased. For example, amplification is easy. For example, an amplifier that has a high amplification factor can be used.

In the embodiment, the first element 11E may be provided, and the second element 12E may be omitted. In such a case, detection is possible with high sensitivity by using a circuit (a filter or the like) that can reduce the signal corresponding to the double frequency 2f1 and selectively amplify the signal corresponding to the frequency of the first frequency f1.

For example, in the magnetic sensor 110A described in reference to FIG. 4, the first resistance part R1 may include an element including the first element 11E, the first wire 21, and the first magnetic part 31. The second resistance part R2 may include an element including the second element 12E, the second wire 22, and the second magnetic part 32. For example, higher detection sensitivity is obtained by forming a bridge circuit of the two elements of the magnetic sensor 111. The phases of the magnetic fields applied to the element including the first element 11E and the element including the second element 12E are reversed between the elements.

In one example of the case where the two elements of the magnetic sensor 111 are used as the first resistance part R1 and the second resistance part R2, the third resistance part R3 and the fourth resistance part R4 each include an element and a wire but do not include magnetic parts. The third resistance part R3 and the fourth resistance part R4 function as resistors.

As recited above, the magnetic sensor 111 (referring to FIG. 6A) includes the first element 11E including the first magnetic layer 11, the second element 12E including the second magnetic layer 12, the first wire 21, the second wire 22, the first circuit 71, and the second circuit 72. The first circuit 71 is electrically connected to the first wire 21 and the second wire 22. The second circuit 72 is electrically connected to the first element 11E and the second element 12E. The first circuit 71 supplies a first alternating current (the alternating current Ia1) to the first wire 21 and supplies a second alternating current (the alternating current Ia2) to the second wire 22. The second circuit 72 supplies a first element current (the current Id1) to the first element 11E and supplies a second element current (the current Id2) to the second element 12E (referring to FIG. 6A).

A first time is a time when the first alternating current (the alternating current Ia1) is positive. A second time is a time when the first alternating current (the alternating current Ia1) is negative.

At the first time, the first alternating current (the alternating current Ia1) has a first alternating current orientation, and the second alternating current (the alternating current Ia2) has a second alternating current orientation. For example, the orientations of these currents are the orientations of the "arrows" illustrated in FIG. 6A and FIG. 6B.

At the second time, the first alternating current (the alternating current Ia1) has the reverse orientation of the first alternating current orientation, and the second alternating current (the alternating current Ia2) has the reverse orientation of the second alternating current orientation. For example, the orientations of these currents are the reverse orientations of the "arrows" illustrated in FIG. 6A and FIG. 6B.

At the first time, the first element current (the current Id1) has a first element current orientation, and the second element current (the current Id2) has a second element current orientation. For example, the orientations of these currents are the "arrow" orientations illustrated in FIG. 6A and FIG. 6B.

At the second time, the first element current (the current Id1) has the first element current orientation, and the second element current (the current Id1) has the second element current orientation. For example, the orientations of these currents are the orientations of the "arrows" illustrated in FIG. 6A and FIG. 6B.

In the embodiment, the first alternating current orientation has a component in the orientation of the first element current (referring to FIG. 6A and FIG. 6B). The second alternating current orientation has a component in the reverse orientation of the orientation of the second element current.

For example, the phase of the first alternating current is the reverse of the phase of the second alternating current in at least a portion of time in the orientation of the external magnetic field applied to the first element 11E and the second element 12E.

Thus, the phases are mutually-reversed between the first alternating-current magnetic field Ha1 applied to the first element 11E and the second alternating-current magnetic field Ha2 applied to the second element 12E. By using such alternating-current magnetic fields having reverse phases, the component of the double frequency $2f1$ (e.g., the unnecessary signal) can be suppressed. According to the embodiment, a magnetic sensor can be provided in which the detection sensitivity can be increased.

A sensor module 211 according to the embodiment (referring to FIG. 6A and FIG. 6B) includes, for example, the magnetic sensor 111 and the first circuit 71. The sensor module 211 may include the second circuit 72 and the third circuit 73.

Figure 9A:
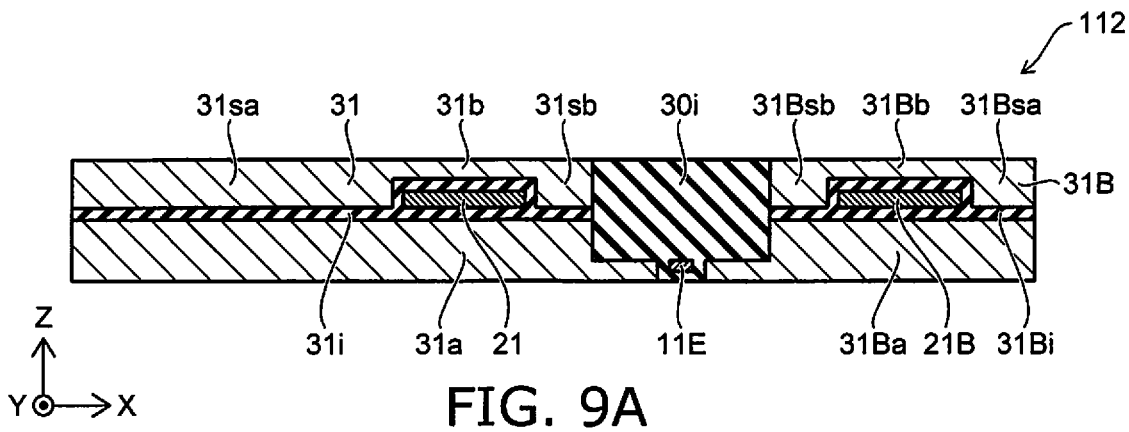
FIG. 9A and FIG. 9B are schematic cross-sectional views illustrating magnetic sensors according to the first embodiment.
Figure 9B:
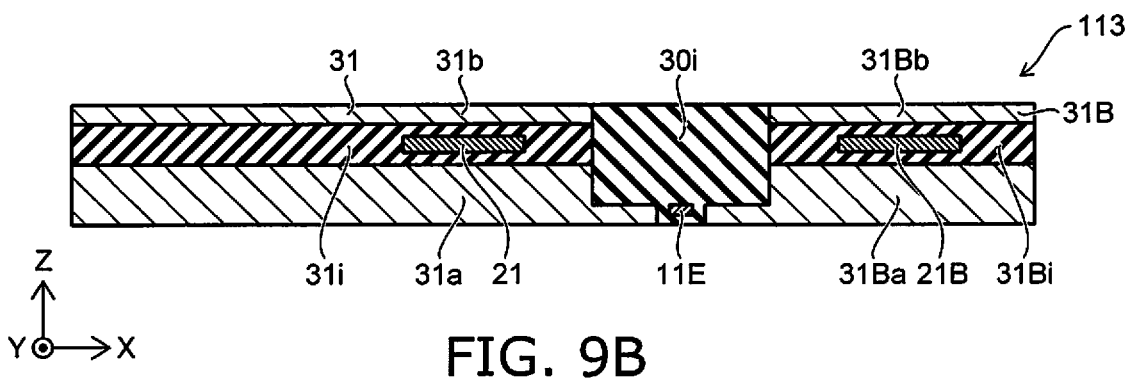

FIG. 9A and FIG. 9B are schematic cross-sectional views illustrating magnetic sensors according to the first embodiment.

In a magnetic sensor 112 according to the embodiment as shown in FIG. 9A, the first side region 31*sa* and the first counter side region 31*sb* are continuous with the first counter region 31*b* in the first magnetic part 31. The first side region 31*sa* and the first counter side region 31*sb* are separated from the first region 31*a*. For example, the insulating region 31*i* is provided between the first side region 31*sa* and the first region 31*a*. For example, the insulating region 31*i* is provided between the first counter side region 31*sb* and the first region 31*a*.

In the first side magnetic part 31B, the first side region 31Bsa of the first side magnetic part 31B and the first counter side region 31Bsb of the first side magnetic part 31B are continuous with the first counter region 31Bb of the first side magnetic part 31B. For example, the insulating region 31Bi is provided between the first side region 31Bsa of the first side magnetic part 31B and the first region 31Ba of the first side magnetic part 31B. For example, the insulating region 31Bi is provided between the first counter side region 31Bsb of the first side magnetic part 31B and the first region 31Ba of the first side magnetic part 31B.

In a magnetic sensor 113 according to the embodiment as shown in FIG. 9B, the first side region 31*sa* and the first counter side region 31*sb* may be omitted from the first magnetic part 31.

In the magnetic sensors 112 and 113 as well, a magnetic sensor can be provided in which the detection sensitivity can be increased.

As shown in FIG. 9A and FIG. 9B, an insulating region 30*i* may be provided between the first magnetic part 31 and the first side magnetic part 31B.

FIG. 10, FIG. 11, FIG. 12A, FIG. 12B, FIG. 13A, and FIG. 13B are schematic views illustrating a magnetic sensor according to the first embodiment.

Figure 10:
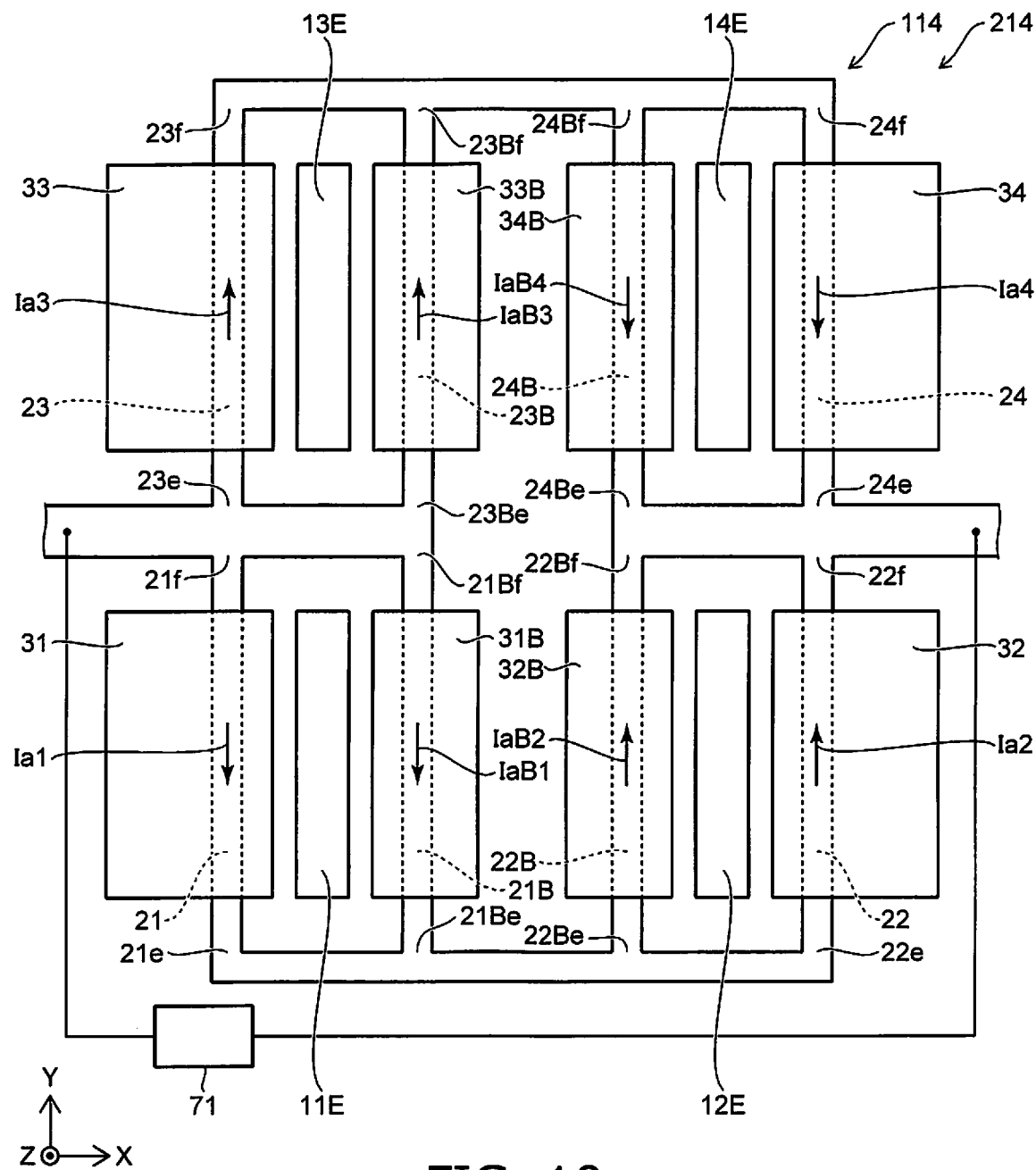
FIG. 10 is a schematic view illustrating a magnetic sensor according to the first embodiment.
Figure 11:
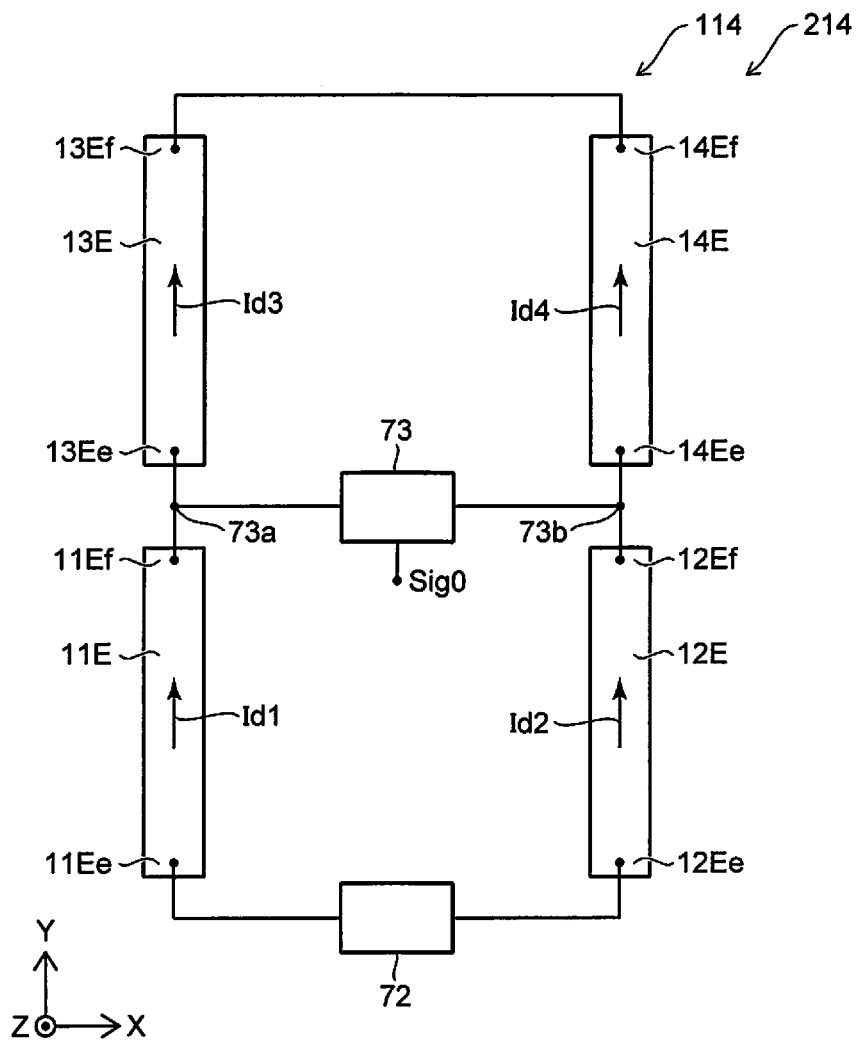
FIG. 11 is a schematic view illustrating the magnetic sensor according to the first embodiment.
Figure 12A:
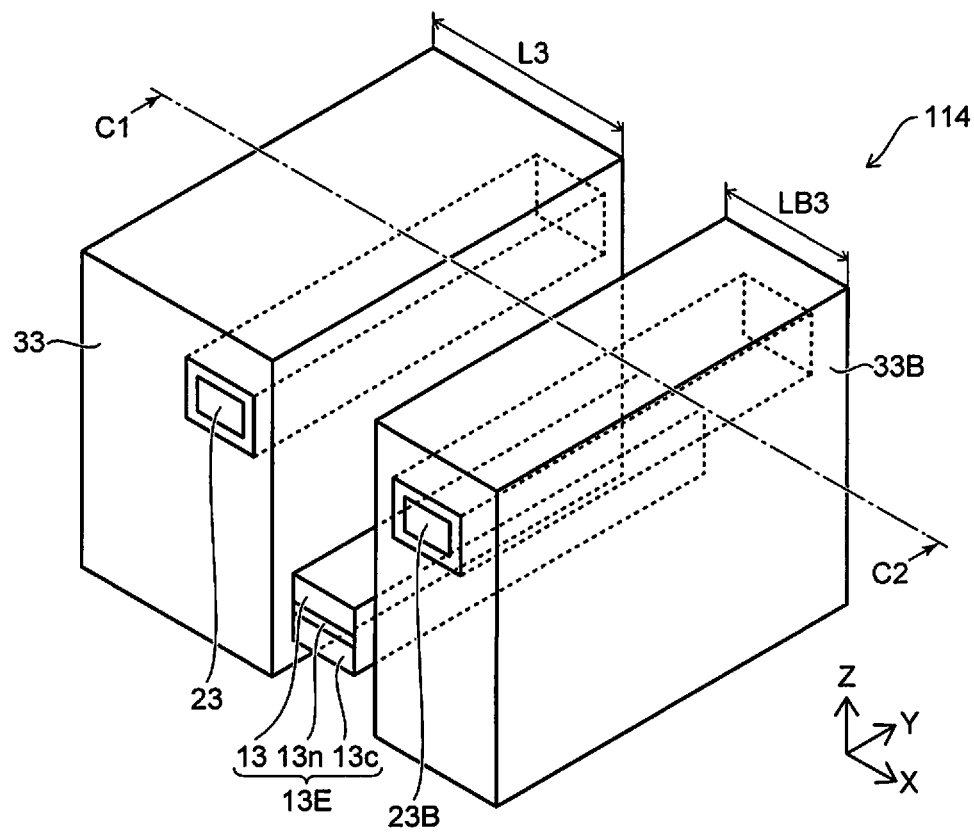
FIG. 12A and FIG. 12B are schematic views illustrating the magnetic sensor according to the first embodiment.
Figure 12B:
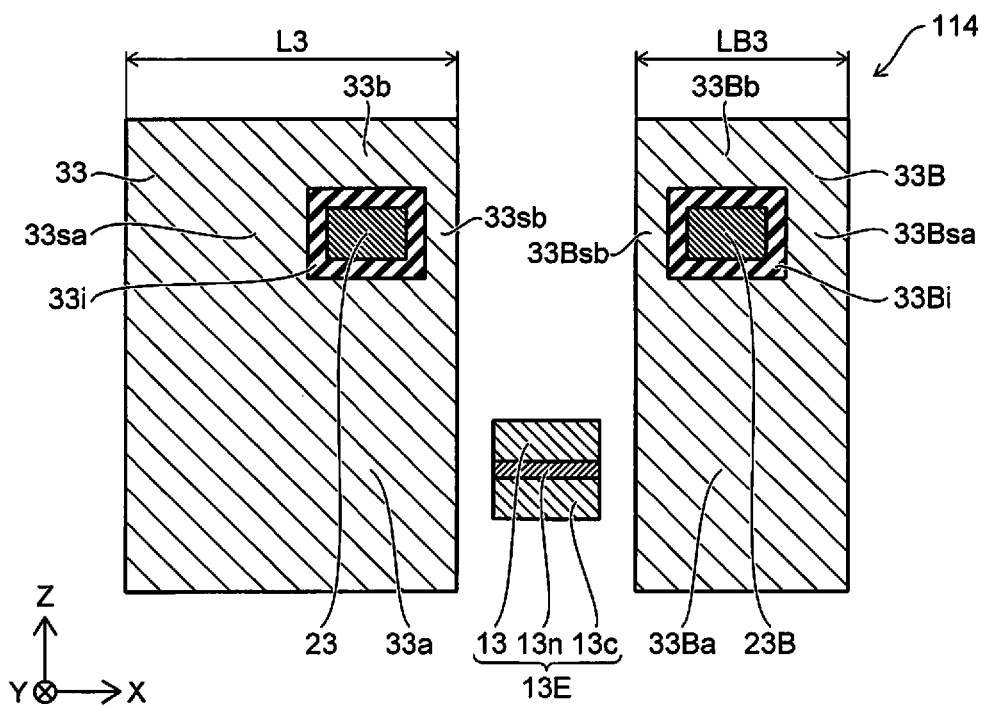
Figure 13A:
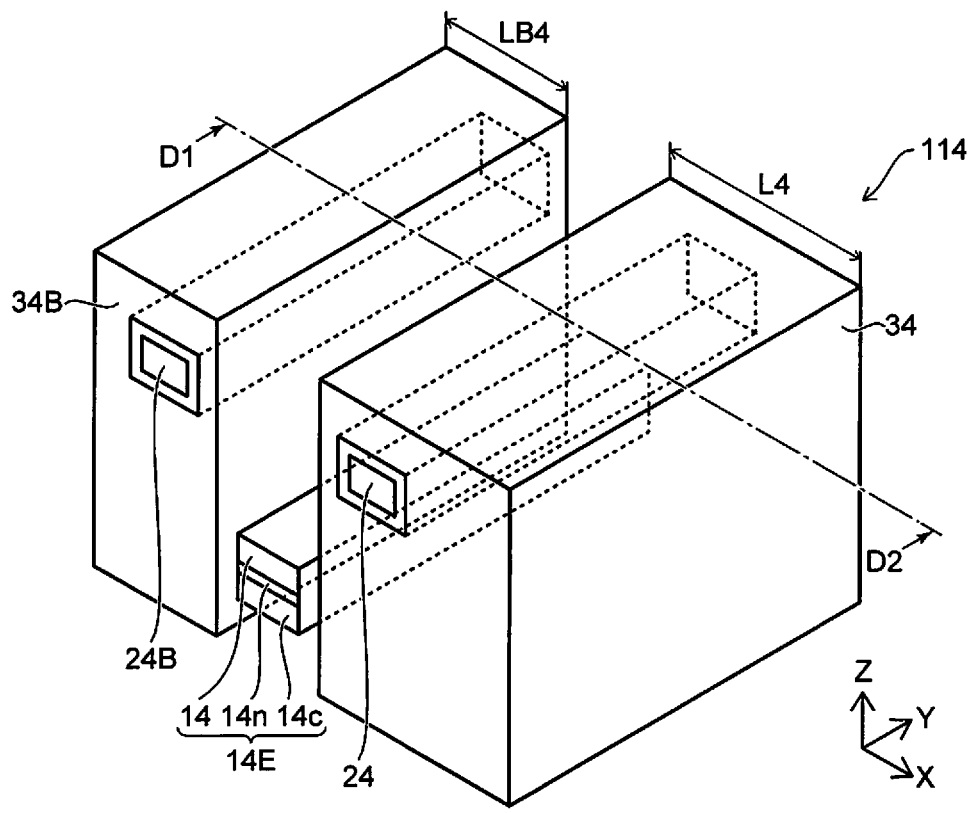
FIG. 13A and FIG. 13B are schematic views illustrating the magnetic sensor according to the first embodiment.
Figure 13B:
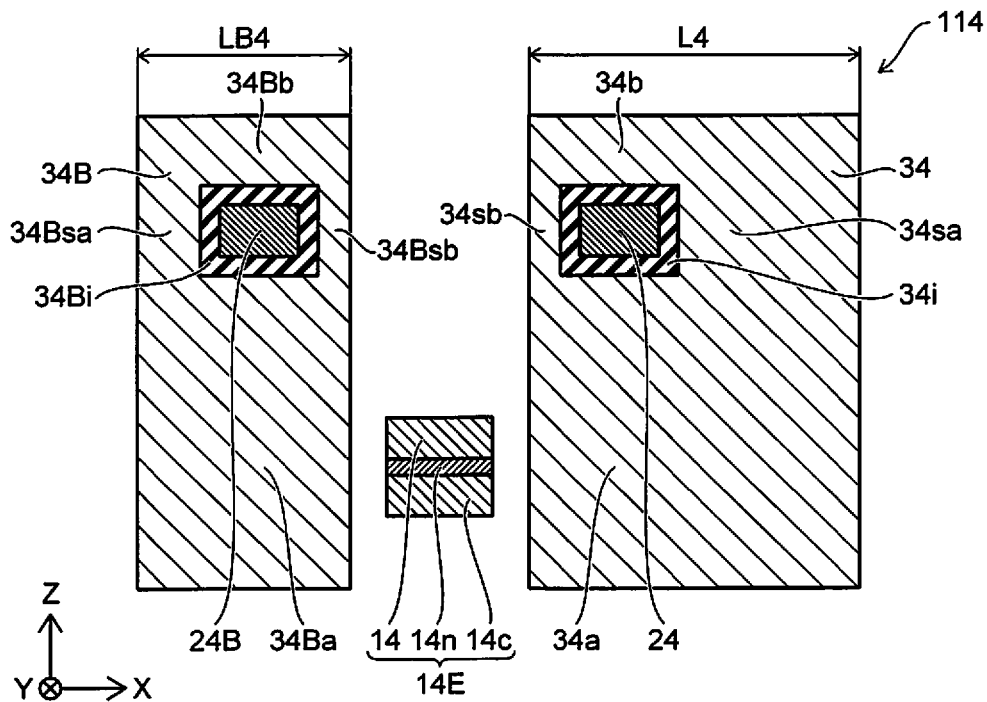

FIG. 10 and FIG. 11 are schematic plan views. FIG. 12A is a perspective view. FIG. 12B is a line C1-C2 cross-sectional view of FIG. 12A. FIG. 13A is a perspective view. FIG. 13B is a line D1-D2 cross-sectional view of FIG. 13A.

As shown in FIG. 10, the magnetic sensor 114 according to the embodiment includes a third element 13E, a third wire 23, a third magnetic part 33, a fourth element 14E, a fourth wire 24, and a fourth magnetic part 34 in addition to the first element 11E, the first wire 21, the first magnetic part 31, the second element 12E, the second wire 22, and the second magnetic part 32. The configurations described above are applicable to the first element 11E, the first wire 21, the first magnetic part 31, the second element 12E, the second wire 22, and the second magnetic part 32.

As shown in FIG. 12A and FIG. 12B, the third element 13E includes a third magnetic layer 13, a third counter magnetic layer 13c, and a third nonmagnetic layer 13n. The third nonmagnetic layer 13n is provided between the third magnetic layer 13 and the third counter magnetic layer 13c. The direction from the third counter magnetic layer 13c toward the third magnetic layer 13 is along the first direction (the Z-axis direction).

The third wire 23 extends in the second direction (e.g., the Y-axis direction).

As shown in FIG. 12B, the third magnetic part 33 includes a third region 33a and a third counter region 33b. At least a portion of the third wire 23 is between the third region 33a and the third counter region 33b in the first direction (the Z-axis direction).

As shown in FIG. 13A and FIG. 13B, the fourth element 14E includes a fourth magnetic layer 14, a fourth counter magnetic layer 14c, and a fourth nonmagnetic layer 14n. The fourth nonmagnetic layer 14n is provided between the fourth magnetic layer 14 and the fourth counter magnetic layer 14c. The direction from the fourth counter magnetic layer 14c toward the fourth magnetic layer 14 is along the first direction (the Z-axis direction).

The fourth wire 24 extends in the second direction (the Y-axis direction).

As shown in FIG. 13B, the fourth magnetic part 34 includes a fourth region 34a and a fourth counter region 34b. At least a portion of the fourth wire 24 is between the fourth region 34a and the fourth counter region 34b in the first direction (the Z-axis direction).

As shown in FIG. 10, the third wire 23 includes a third end portion 23e of the third wire 23 and a third other end portion 23f of the third wire 23. The direction from the third end portion 23e of the third wire 23 toward the third other end portion 23f of the third wire 23 is along the second direction (the Y-axis direction).

The fourth wire 24 includes a fourth end portion 24e of the fourth wire 24 and a fourth other end portion 24f of the fourth wire 24. The direction from the fourth end portion 24e of the fourth wire 24 toward the fourth other end portion 24f of the fourth wire 24 is along the second direction (the Y-axis direction).

The third other end portion 23f of the third wire 23 is electrically connected to the fourth other end portion 24f of the fourth wire 24. The third end portion 23e of the third wire 23 is electrically connected to the first other end portion 21f of the first wire 21. The fourth end portion 24e of the fourth wire 24 is electrically connected to the second other end portion 22f of the second wire 22.

In the example, the magnetic sensor 114 further includes a third side wire 23B, a third side magnetic part 33B, a fourth side wire 24B, and a fourth side magnetic part 34B.

The third side wire 23B and the fourth side wire 24B extend in the second direction (the Y-axis direction).

As shown in FIG. 12B, the third side magnetic part 33B includes a third region 33Ba of the third side magnetic part 33B and a third counter region 33Bb of the third side magnetic part 33B. At least a portion of the third side wire 23B is between the third region 33Ba of the third side magnetic part 33B and the third counter region 33Bb of the third side magnetic part 33B in the first direction (the Z-axis direction).

The position in the third direction (the X-axis direction) of the third element 13E is between the position in the third direction of the third wire 23 and the position in the third direction of the third side wire 23B.

As shown in FIG. 13B, the fourth side magnetic part 34B includes a fourth region 34Ba of the fourth side magnetic part 34B and a fourth counter region 34Bb of the fourth side magnetic part 34B. At least a portion of the fourth side wire 24B is between the fourth region 34Ba of the fourth side magnetic part 34B and the fourth counter region 34Bb of the fourth side magnetic part 34B in the first direction (the Z-axis direction).

The position in the third direction (the X-axis direction) of the fourth element 14E is between the position in the third direction of the fourth wire 24 and the position in the third direction of the fourth side wire 24B.

In the example as shown in FIG. 12B, a length L3 along the third direction (the X-axis direction) of the third magnetic part 33 is longer than a length LB3 along the third direction of the third side magnetic part 33B.

In the example as shown in FIG. 13B, a length L4 along the third direction (the X-axis direction) of the fourth magnetic part 34 is longer than a length LB4 along the third direction of the fourth side magnetic part 34B.

As shown in FIG. 12B, an insulating region 33i may be provided between the third wire 23 and the third magnetic part 33. An insulating region 33Bi may be provided between the third side wire 23B and the third side magnetic part 33B.

As shown in FIG. 13B, an insulating region 34i may be provided between the fourth wire 24 and the fourth magnetic part 34. An insulating region 34Bi may be provided between the fourth side wire 24B and the fourth side magnetic part 34B.

In the example as shown in FIG. 12B, the direction from the third region 33a toward the third element 13E is along the third direction (the X-axis direction).

In the example, the third magnetic part 33 further includes a third side region 33sa and a third counter side region 33sb. At least a portion of the third wire 23 is between the third side region 33sa and the third counter side region 33sb in the third direction (the X-axis direction).

For example, the third side magnetic part 33B further includes a third side region 33Bsa of the third side magnetic part 33B and a third counter side region 33Bsb of the third side magnetic part 33B. At least a portion of the third side wire 23B is between the third side region 33Bsa of the third side magnetic part 33B and the third counter side region 33Bsb of the third side magnetic part 33B in the third direction (the X-axis direction).

The position in the third direction (the X-axis direction) of the third counter side region 33sb of the third magnetic part 33 is between the position in the third direction of the third side region 33sa of the third magnetic part 33 and the position in the third direction of the third side region 33Bsa of the third side magnetic part 33B.

The position in the third direction (the X-axis direction) of the third counter side region 33Bsb of the third side magnetic part 33B is between the position in the third direction of the third counter side region 33sb of the third magnetic part 33 and the position in the third direction of the third side region 33Bsa of the third side magnetic part 33B.

In the example as shown in FIG. 13B, the direction from the fourth element 14E toward the fourth region 34a is along the third direction (the X-axis direction).

In the example, the fourth magnetic part 34 further includes a fourth side region 34*sa* and a fourth counter side region 34*sb*. At least a portion of the fourth wire 24 is between the fourth side region 34*sa* and the fourth counter side region 34*sb* in the third direction (the X-axis direction).

For example, the fourth side magnetic part 34B further includes a fourth side region 34Bsa of the fourth side magnetic part 34B and a fourth counter side region 34Bsb of the fourth side magnetic part 34B. At least a portion of the fourth side wire 24B is between the fourth side region 34Bsa of the fourth side magnetic part 34B and the fourth counter side region 34Bsb of the fourth side magnetic part 34B in the third direction (the X-axis direction).

The position in the third direction (the X-axis direction) of the fourth counter side region 34*sb* of the fourth magnetic part 34 is between the position in the third direction of the fourth side region 34*sa* of the fourth magnetic part 34 and the position in the third direction of the fourth side region 34Bsa of the fourth side magnetic part 34B.

The position in the third direction (the X-axis direction) of the fourth counter side region 34Bsb of the fourth side magnetic part 34B is between the position in the third direction of the fourth counter side region 34*sb* of the fourth magnetic part 34 and the position in the third direction of the fourth side region 34Bsa of the fourth side magnetic part 34B.

As shown in FIG. 10, for example, the third side wire 23B includes a third end portion 23Be of the third side wire 23B and a third other end portion 23Bf of the third side wire 23B. The direction from the third end portion 23Be of the third side wire 23B toward the third other end portion 23Bf of the third side wire 23B is along the second direction (the Y-axis direction).

The direction from the third end portion 23*e* of the third wire 23 toward the third end portion 23Be of the third side wire 23B is along the third direction (the X-axis direction). The direction from the third other end portion 23*f* of the third wire 23 toward the third other end portion 23Bf of the third side wire 23B is along the third direction (the X-axis direction). The third end portion 23*e* of the third wire 23 and the third end portion 23Be of the third side wire 23B are electrically connected to each other. The third other end portion 23*f* of the third wire 23 and the third other end portion 23Bf of the third side wire 23B are electrically connected to each other.

As shown in FIG. 10, for example, the fourth side wire 24B includes a fourth end portion 24Be of the fourth side wire 24B and a fourth other end portion 24Bf of the fourth side wire 24B. The direction from the fourth end portion 24Be of the fourth side wire 24B toward the fourth other end portion 24Bf of the fourth side wire 24B is along the second direction (the Y-axis direction).

The direction from the fourth end portion 24Be of the fourth side wire 24B toward the fourth end portion 24*e* of the fourth wire 24 is along the third direction (the X-axis direction). The direction from the fourth other end portion 24Bf of the fourth side wire 24B toward the fourth other end portion 24*f* of the fourth wire 24 is along the third direction (the X-axis direction). The fourth end portion 24*e* of the fourth wire 24 and the fourth end portion 24Be of the fourth side wire 24B are electrically connected to each other. The fourth other end portion 24*f* of the fourth wire 24 and the fourth other end portion 24Bf of the fourth side wire 24B are electrically connected to each other.

An alternating current Ia3 is supplied from the first circuit 71 to the third wire 23. An alternating current IaB3 is supplied from the first circuit 71 to the third side wire 23B.

An alternating current Ia4 is supplied from the first circuit 71 to the fourth wire 24. An alternating current IaB4 is supplied from the first circuit 71 to the fourth side wire 24B.

The orientation (the phase) of the alternating current Ia3 is the reverse of the orientation (the phase) of the alternating current Ia1. The orientation (the phase) of the alternating current Ia4 is the reverse of the orientation (the phase) of the alternating current Ia2. The orientation (the phase) of the alternating current IaB3 is the reverse of the orientation (the phase) of the alternating current IaB1. The orientation (the phase) of the alternating current IaB4 is the reverse of the orientation (the phase) of the alternating current IaB2.

As shown in FIG. 11, the third element 13E includes a third end portion 13Ee and a third other end portion 13Ef. The direction from the third end portion 13Ee toward the third other end portion 13Ef is along the Y-axis direction. The fourth element 14E includes a fourth end portion 14Ee and a fourth other end portion 14Ef. The direction from the fourth end portion 14Ee toward the fourth other end portion 14Ef is along the Y-axis direction.

For example, the direction from the third end portion 13Ee toward the fourth end portion 14Ee is along the X-axis direction. The direction from the third other end portion 13Ef toward the fourth other end portion 14Ef is along the X-axis direction.

For example, the second circuit 72 is electrically connected to the first to fourth elements 11E to 14E. In the example, the second circuit 72 is electrically connected to the first end portion 11Ee and electrically connected to the second end portion 12Ee. The first other end portion 11Ef is electrically connected to the third other end portion 13Ef. The second other end portion 12Ef is electrically connected to the fourth other end portion 14Ef. The third other end portion 13Ef is electrically connected to the fourth other end portion 14Ef. For example, the second circuit 72 applies a direct current voltage to the first to fourth elements 11E to 14E. For example, a bridge circuit is formed of the first to fourth elements 11E to 14E.

For example, the second circuit 72 supplies the current Id1 to the first element 11E. The second circuit 72 supplies the current Id2 to the second element 12E. The second circuit 72 supplies a current Id3 to the third element 13E. The second circuit 72 supplies a current Id4 to the fourth element 14E. These currents are, for example, direct currents. In one example, these currents flow in the plane (in the X-Y plane). In another example, these currents may flow in the Z-axis direction.

For example, the first element 11E and the third element 13E are electrically connected in series to each other. The second element 12E and the fourth element 14E are electrically connected in series to each other. The third circuit 73 detects the potential between a connection point 73*a* between the first element 11E and the second element 12E and a connection point 73*b* between the second element 12E and the fourth element 14E.

The signal Sigx (referring to FIG. 7) is suppressed in an output signal Sig0 of the third circuit 73. The detection sensitivity is improved more easily.

For example, in the magnetic sensor 110A described in reference to FIG. 4, elements that each include the first to fourth elements 11E to 14E, the first to fourth wires 21 to 24, and the first to fourth magnetic parts 31 to 34 are used as the first to fourth resistance parts R1 to R4. For example, higher detection sensitivity is obtained.

It is favorable for the distance (e.g., the distance along the X-axis direction) between the second magnetic part 32 and the second element 12E to be, for example, not more than 1/1000 times the length (e.g., the width) along the third direction (the X-axis direction) of the second magnetic part 32. It is favorable for the distance (e.g., the distance along the X-axis direction) between the third magnetic part 33 and the third element 13E to be, for example, not more than 1/1000 times the length (e.g., the thickness) along the third direction (the X-axis direction) of the third magnetic part 33. It is favorable for the distance (e.g., the distance along the X-axis direction) between the fourth magnetic part 34 and the fourth element 14E to be, for example, not more than 1/1000 times the length (e.g., the thickness) along the third direction (the X-axis direction) of the fourth magnetic part 34. Thereby, the magnetic fields from the magnetic parts easily are applied efficiently to the elements.

A sensor module 214 according to the embodiment (referring to FIG. 10 and FIG. 11) includes, for example, the magnetic sensor 114 and the first circuit 71. The sensor module 214 may include the second circuit 72 and the third circuit 73.

Second Embodiment

FIG. 14A, FIG. 14B, FIG. 15A, and FIG. 15B are schematic views illustrating a magnetic sensor according to a second embodiment.

Figure 14A:
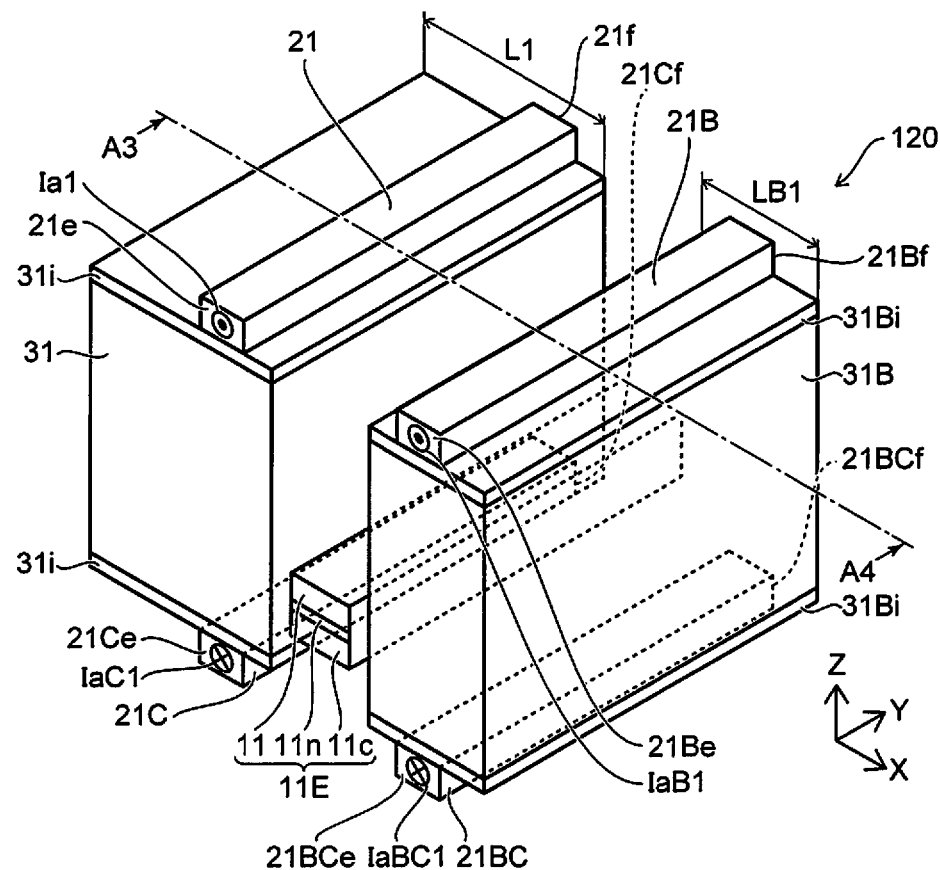
FIG. 14A and FIG. 14B are schematic views illustrating a magnetic sensor according to a second embodiment.
Figure 14B:
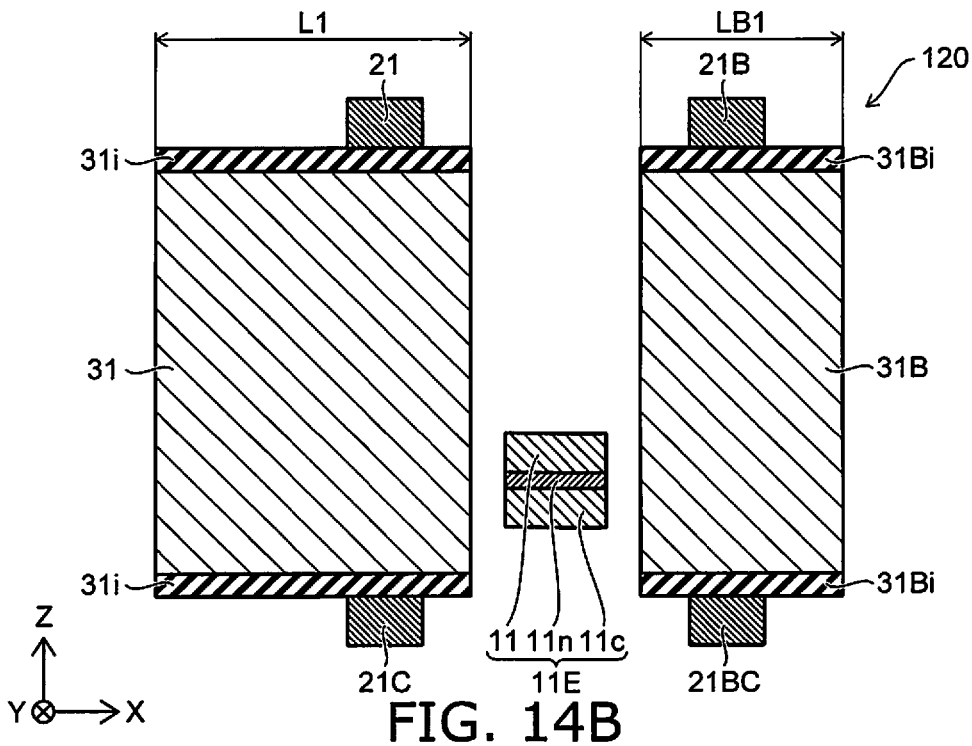
Figure 15A:
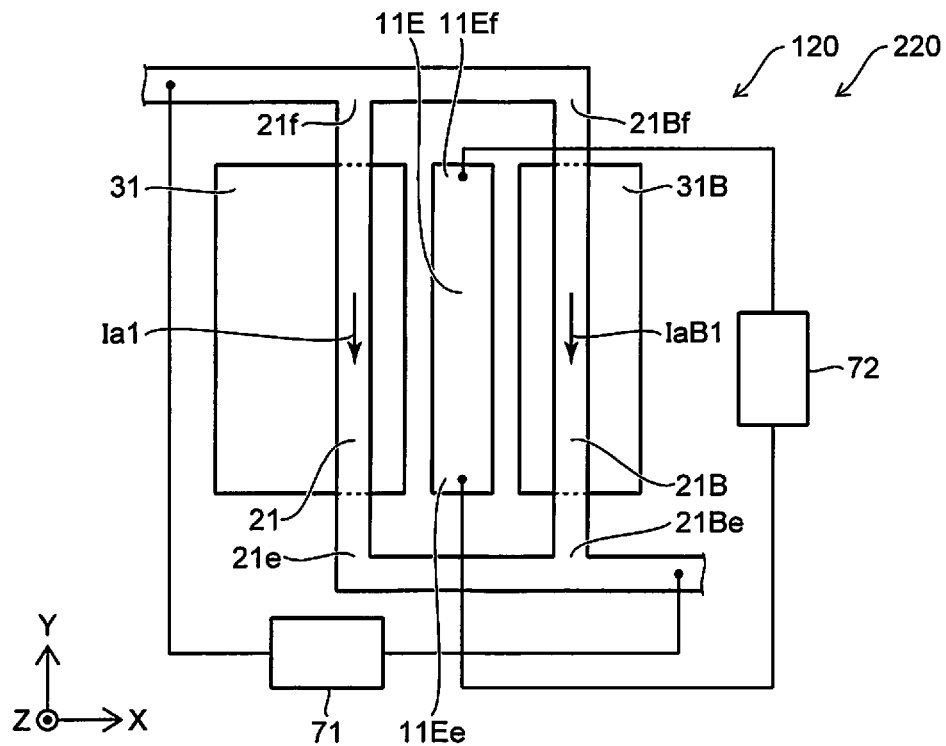
FIG. 15A and FIG. 15B are schematic views illustrating the magnetic sensor according to a second embodiment.
Figure 15B:
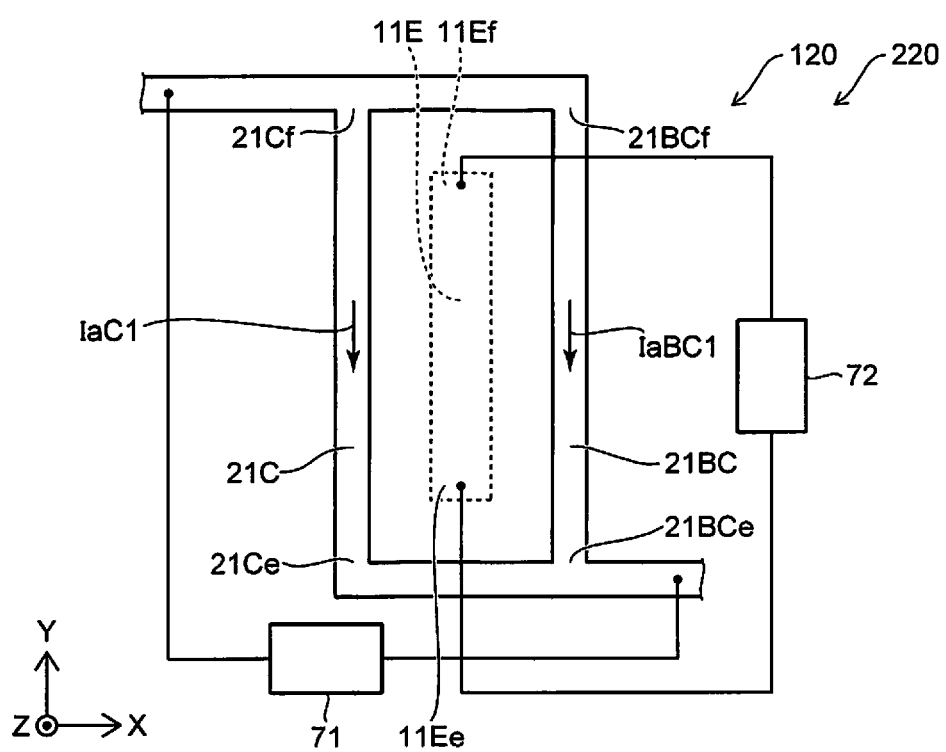

FIG. 14A is a perspective view. FIG. 14B is a line A3-A4 cross-sectional view of FIG. 14A. FIG. 15A and FIG. 15B are plan views. A state in which the first magnetic part 31, etc., are removed is illustrated in FIG. 15B for easier viewing of the drawing.

As shown in FIG. 14A, the magnetic sensor 120 according to the embodiment includes the first element 11E, the first wire 21, a first counter wire 21C, and the first magnetic part 31.

The first element 11E includes the first magnetic layer 11, the first counter magnetic layer 11c, and the first nonmagnetic layer 11n. The first nonmagnetic layer 11n is provided between the first magnetic layer 11 and the first counter magnetic layer 11c. The direction from the first counter magnetic layer 11c toward the first magnetic layer 11 is along the first direction. The first direction is taken as the Z-axis direction.

The first wire 21 extends in the second direction crossing the first direction. The second direction is, for example, the Y-axis direction. The first counter wire 21C also extends in the second direction (the Y-axis direction).

The first magnetic part 31 is provided between the first wire 21 and the first counter wire 21C in the first direction (the Z-axis direction). In the example, the insulating region 31i is provided between the first wire 21 and the first magnetic part 31 and between the first counter wire 21C and the first magnetic part 31.

The first wire 21 includes the first end portion 21e of the first wire 21 and the first other end portion 21f of the first wire 21. The direction from the first end portion 21e of the first wire 21 toward the first other end portion 21f of the first wire 21 is along the second direction (the Y-axis direction).

The first counter wire 21C includes a first end portion 21Ce of the first counter wire 21C and a first other end portion 21Cf of the first counter wire 21C. The direction from the first end portion 21Ce of the first counter wire 21C toward the first other end portion 21Cf of the first counter wire 21C is along the second direction (the Y-axis direction).

The direction from the first end portion 21Ce of the first counter wire 21C toward the first end portion 21e of the first wire 21 is along the first direction (the Z-axis direction). The direction from the first other end portion 21Cf of the first counter wire 21C toward the first other end portion 21f of the first wire 21 is along the first direction (the Z-axis direction).

As shown in FIG. 15A and FIG. 15B, the first circuit 71 is provided in the magnetic sensor 120. In FIG. 15A, the first counter wire 21C overlaps the first wire 21 and is not illustrated. The first counter wire 21C is illustrated in FIG. 15B.

As shown in FIG. 14A, FIG. 15A, and FIG. 15B, for example, the first circuit 71 supplies the alternating current Ia1 to the first wire 21 and supplies an alternating current IaC1 to the first counter wire 21C. The orientations (the phases) of these alternating currents are mutually-reversed.

For example, the first circuit 71 sets the potential of the first end portion 21Ce of the first counter wire 21C to be higher than the potential of the first other end portion 21Cf of the first counter wire 21C at the first time at which the potential of the first end portion 21e of the first wire 21 is set to be lower than the potential of the first other end portion 21f of the first wire 21. The polarity (the phase) of the alternating current Ia1 is the reverse of the polarity (the phase) of the alternating current IaC1.

The first circuit 71 sets the potential of the first end portion 21Ce of the first counter wire 21C to be lower than the potential of the first other end portion 21Cf of the first counter wire 21C at the second time at which the potential of the first end portion 21e of the first wire 21 is set to be higher than the potential of the first other end portion 21f of the first wire 21. The polarity (the phase) of the alternating current Ia1 is the reverse of the polarity (the phase) of the alternating current IaC1.

By such a configuration, as described below, the alternating-current magnetic field that is generated by the alternating current Ia1 flowing in the first wire 21 and the alternating-current magnetic field that is generated by the alternating current IaC1 flowing in the first counter wire 21C strengthen each other at the position of the first element 11E. Thereby, the alternating-current magnetic fields can be applied efficiently to the first element 11E. The detection sensitivity can be increased thereby. In the embodiment, a magnetic sensor can be provided in which the detection sensitivity can be improved.

As shown in FIG. 14A and FIG. 14B, the magnetic sensor 120 may further include the first side wire 21B, a first counter side wire 21BC, and the first side magnetic part 31B. The configurations of the first wire 21, the first counter wire 21C, and the first magnetic part 31 respectively are applicable to the first side wire 21B, the first counter side wire 21BC, and the first side magnetic part 31B. In the example, the insulating region 31Bi is provided between the first side wire 21B and the first side magnetic part 31B and between the first counter side wire 21BC and the first side magnetic part 31B.

The first circuit 71 supplies the alternating current IaB1 to the first side wire 21B. The first circuit 71 supplies an alternating current IaBC1 to the first counter side wire 21BC.

The first side wire 21B includes the first end portion 21Be of the first side wire 21B and the first other end portion 21Bf of the first side wire 21B. The direction from the first end portion 21Be of the first side wire 21B toward the first other end portion 21Bf of the first side wire 21B is along the second direction (the Y-axis direction).

The first counter side wire 21BC includes a first end portion 21BCe of the first counter side wire 21BC and a first other end portion 21BCf of the first counter side wire 21BC. The direction from the first end portion 21BCe of the first counter side wire 21BC toward the first other end portion 21BCf of the first counter side wire 21BC is along the second direction (the Y-axis direction).

At the first time recited above, the first circuit 71 sets the potential of the first end portion 21Be of the first side wire 21B to be lower than the potential of the first other end portion 21Bf of the first side wire 21B. At the first time recited above, the first circuit 71 sets the potential of the first end portion 21BCe of the first counter side wire 21BC to be higher than the potential of the first other end portion 21BCf of the first counter side wire 21BC.

At the second time recited above, the first circuit 71 sets the potential of the first end portion 21Be of the first side wire 21B to be higher than the potential of the first other end portion 21Bf of the first side wire 21B. At the second time recited above, the first circuit 71 sets the potential of the first end portion 21BCe of the first counter side wire 21BC to be lower than the potential of the first other end portion 21BCf of the first counter side wire 21BC.

As shown in FIG. 14A and FIG. 14B, for example, the length L1 along the third direction of the first magnetic part 31 may be longer than the length LB1 along the third direction of the first side magnetic part 31B.

The second circuit 72 may be provided as shown in FIG. 15A and FIG. 15B. The first element 11E includes the first end portion 11Ee and the first other end portion 11Ef. The second circuit 72 is electrically connected to the first end portion 11Ee and the first other end portion 11Ef. The second circuit 72 detects a value corresponding to the electrical resistance of the first element 11E.

Figure 16:
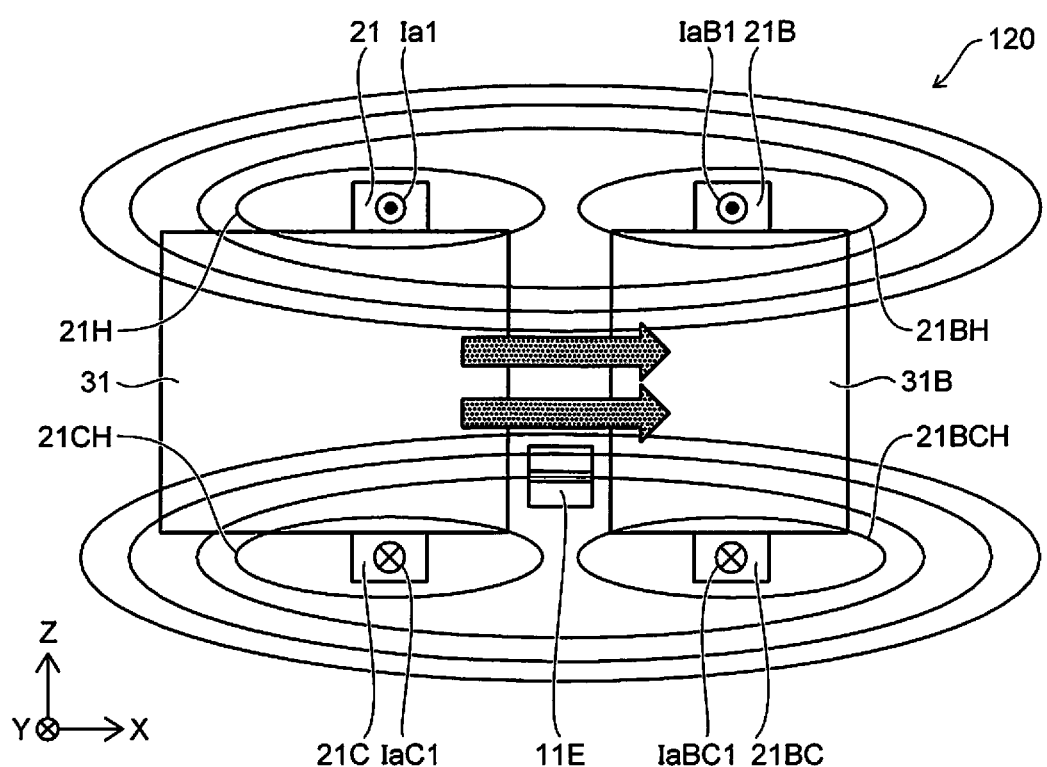
FIG. 16 is a schematic cross-sectional view illustrating an operation of the magnetic sensor according to the second embodiment.

FIG. 16 is a schematic cross-sectional view illustrating an operation of the magnetic sensor according to the second embodiment.

As shown in FIG. 16, the magnetic flux 21H that is generated by the alternating current Ia1 flowing in the first wire 21 and a magnetic flux 21CH that is generated by the alternating current IaC1 flowing in the first counter wire 21C strengthen each other at the position of the first element 11E. On the other hand, these magnetic fields weaken each other outside the first magnetic part 31.

The magnetic flux 21BH that is generated by the alternating current IaB1 flowing in the first side wire 21B and a magnetic flux 21BCH that is generated by the alternating current IaBC1 flowing in the first counter side wire 21BC strengthen each other at the position of the first element 11E. On the other hand, these magnetic fields weaken each other outside the first side magnetic part 31B.

The alternating-current magnetic fields are applied efficiently to the first element 11E. The detection sensitivity can be increased thereby.

A sensor module 220 according to the embodiment (referring to FIG. 15A and FIG. 15B) includes, for example, the magnetic sensor 120 and the first circuit 71. The sensor module 220 may include the second circuit 72 and the third circuit 73.

Figure 17A:
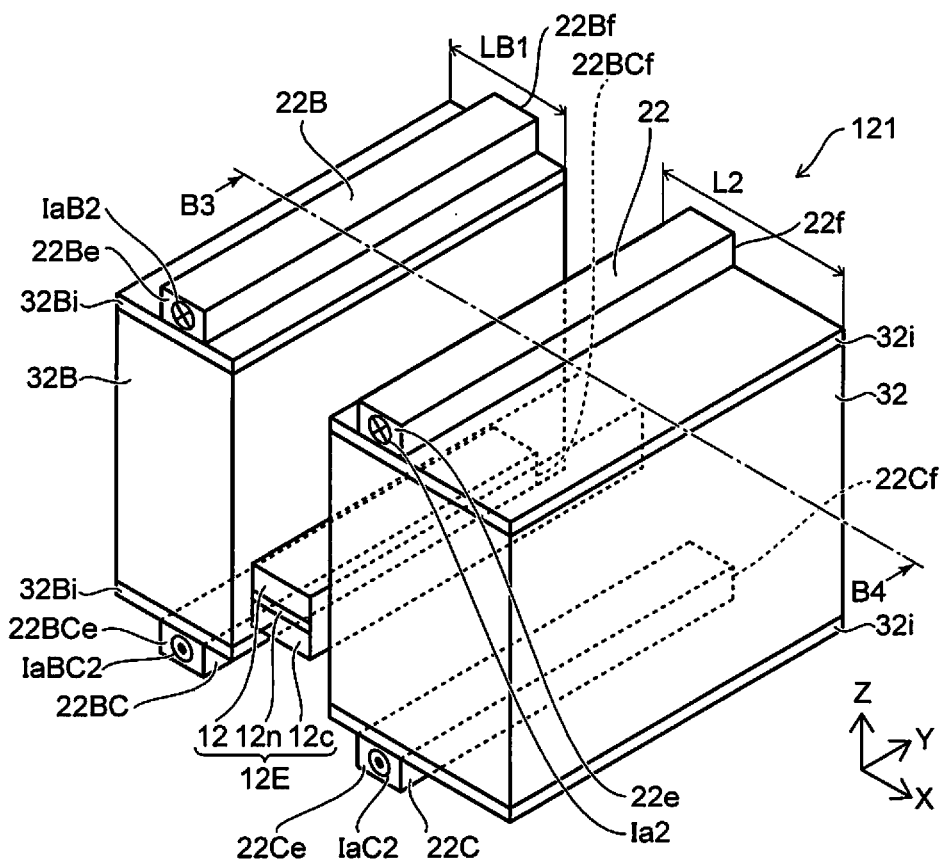
FIG. 17A and FIG. 17B are schematic views illustrating a portion of a magnetic sensor according to the second embodiment.
Figure 17B:
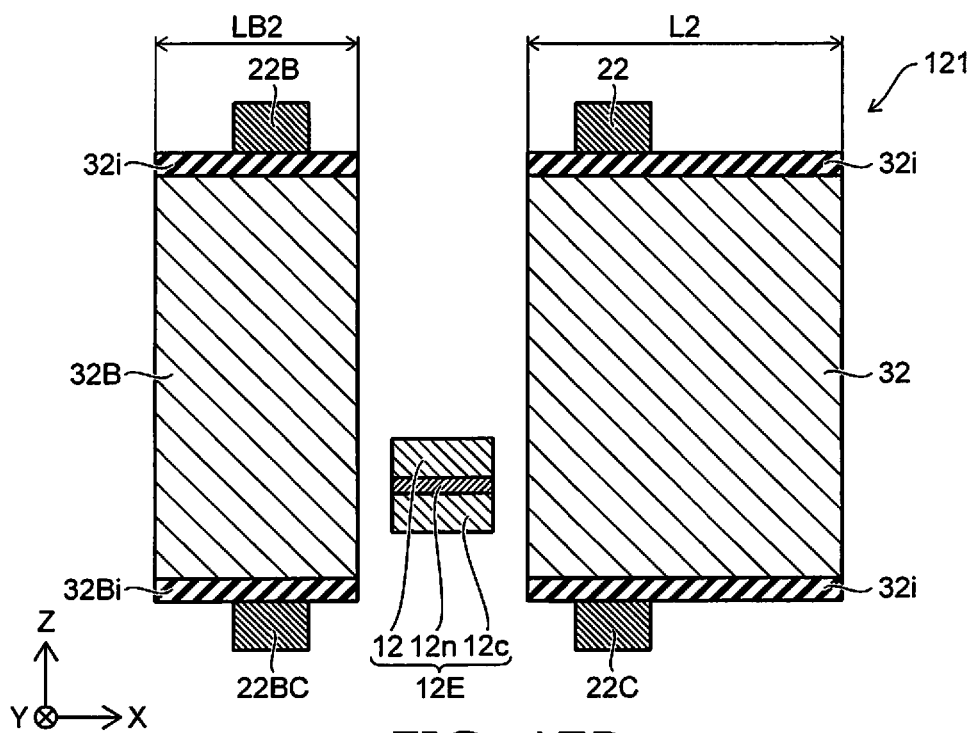

FIG. 17A and FIG. 17B are schematic views illustrating a portion of a magnetic sensor according to the second embodiment.

FIG. 17A is a perspective view. FIG. 17B is a line B3-B4 cross-sectional view of FIG. 17A.

Figure 18A:
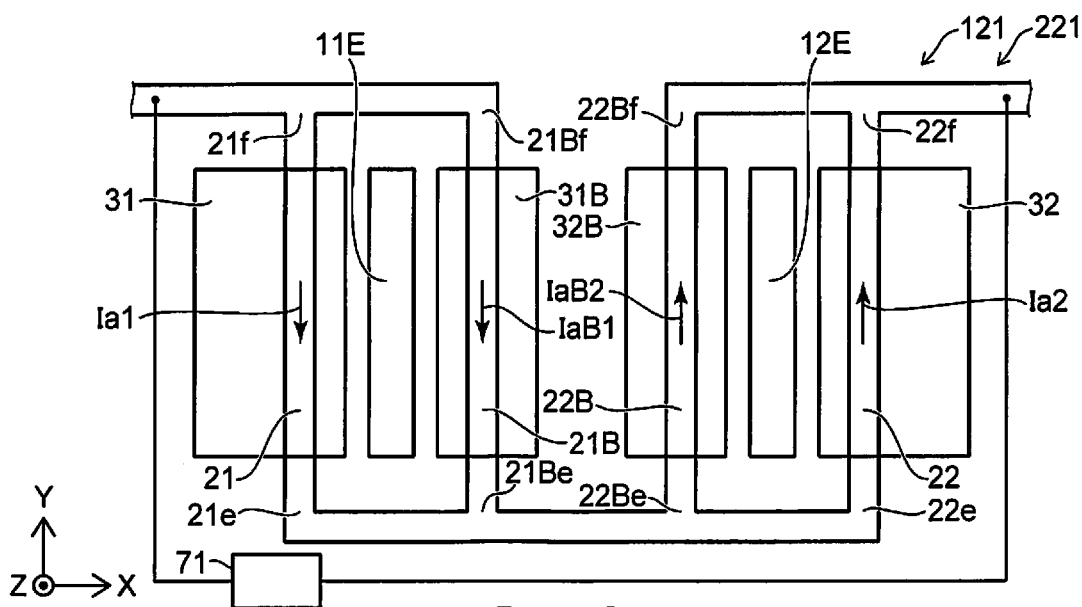
FIG. 18A to FIG. 18C are schematic plan views illustrating the magnetic sensor according to the second embodiment.
Figure 18B:
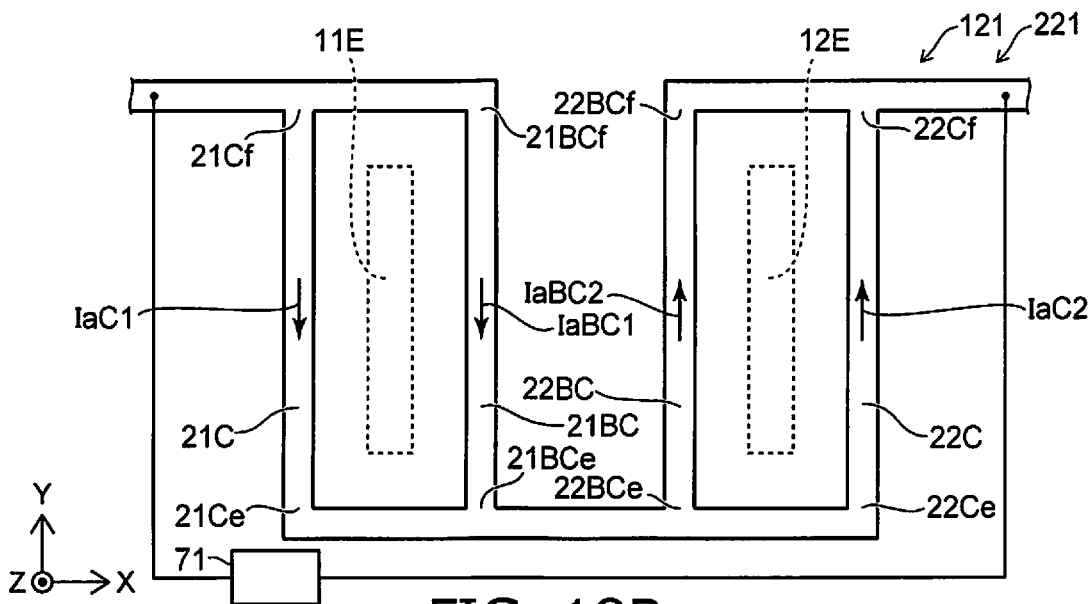
Figure 18C:
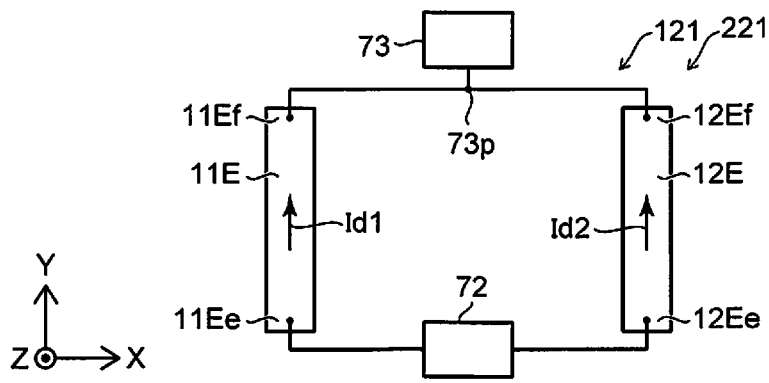

FIG. 18A to FIG. 18C are schematic plan views illustrating the magnetic sensor according to the second embodiment.

A state in which the first magnetic part 31, etc., are removed is illustrated in FIG. 18B for easier viewing of the drawing.

The magnetic sensor 121 illustrated in FIG. 17A includes the second element 12E, the second wire 22, a second counter wire 22C, and the second magnetic part 32 in addition to the first element 11E, the first wire 21, the first counter wire 21C, and the first magnetic part 31 described above.

For example, these elements and these wires are connected as described in reference to FIG. 6A and FIG. 6B (referring to FIG. 18A to FIG. 18C).

The second element 12E includes the second magnetic layer 12, the second counter magnetic layer 12c, and the second nonmagnetic layer 12n. The second nonmagnetic layer 12n is provided between the second magnetic layer 12 and the second counter magnetic layer 12c. The direction from the second counter magnetic layer 12c toward the second magnetic layer 12 is along the first direction (the Z-axis direction).

The second wire 22 extends in the second direction (the Y-axis direction). The second counter wire 22C extends in the second direction. The second magnetic part 32 is provided between the second wire 22 and the second counter wire 22C in the first direction (the Z-axis direction).

The second wire 22 includes the second end portion 22e of the second wire 22 and the second other end portion 22f of the second wire 22. The direction from the second end portion 22e of the second wire 22 toward the second other end portion 22f of the second wire 22 is along the second direction (the Y-axis direction).

The second counter wire 22C includes a second end portion 22Ce of the second counter wire 22C and a second other end portion 22Cf of the second counter wire 22C. The direction from the second end portion 22Ce of the second counter wire 22C toward the second other end portion 22Cf of the second counter wire 22C is along the second direction.

The direction from the second end portion 22Ce of the second counter wire 22C toward the second end portion 22e of the second wire 22 is along the first direction (the Z-axis direction). The direction from the second other end portion 22Cf of the second counter wire 22C toward the second other end portion 22f of the second wire 22 is along the first direction.

The first circuit 71 (referring to FIGS. 15A and 15B) supplies the alternating current Ia2 to the second wire 22. The first circuit 71 supplies an alternating current IaC2 to the second counter wire 22C. The polarities (e.g., the phases) of these alternating currents are mutually-reversed.

For example, at the first time recited above, the first circuit 71 sets the potential of the second end portion 22e of the second wire 22 to be higher than the potential of the second other end portion 22f of the second wire 22. At the first time recited above, the first circuit 71 sets the potential of the second end portion 22Ce of the second counter wire 22C to be lower than the potential of the second other end portion 22Cf of the second counter wire 22C.

At the second time recited above, the first circuit 71 sets the potential of the second end portion 22e of the second wire 22 to be lower than the potential of the second other end portion 22f of the second wire 22. At the second time recited above, the first circuit 71 sets the potential of the second end portion 22Ce of the second counter wire 22C to be higher than the potential of the second other end portion 22Cf of the second counter wire 22C.

Thus, the polarity (the phase) of the alternating current Ia2 flowing in the second wire 22 is the reverse of the polarity (the phase) of the alternating current Ia1 flowing in the first wire 21. The polarity (the phase) of the alternating current IaC2 flowing in the second counter wire 22C is the reverse of the polarity (the phase) of the alternating current IaC1 flowing in the first counter wire 21C. The polarity (the phase) of the alternating current IaC2 flowing in the second counter wire 22C is the reverse of the polarity (the phase) of the alternating current Ia2 flowing in the second wire 22.

For example, the alternating-current magnetic fields due to the alternating currents substantially cancel each other in the first element 11E and the second element 12E. The detection sensitivity can be improved easily.

As shown in FIG. 17A and FIG. 17B, the magnetic sensor 121 may further include the second side wire 22B, a second counter side wire 22BC, and the second side magnetic part 32B. The configurations of the second wire 22, the second counter wire 22C, and the second magnetic part 32 respectively are applicable to the second side wire 22B, the second counter side wire 22BC, and the second side magnetic part 32B. In the example, the insulating region 32Bi is provided between the second side wire 22B and the second side magnetic part 32B and between the second counter side wire 22BC and the second side magnetic part 32B.

The first circuit 71 supplies the alternating current IaB2 to the second side wire 22B. The first circuit 71 supplies an alternating current IaBC2 to the second counter side wire 22BC.

The second side wire 22B includes the second end portion 22Be of the second side wire 22B and the second other end portion 22Bf of the second side wire 22B. The direction from the second end portion 22Be of the second side wire 22B toward the second other end portion 22Bf of the second side wire 22B is along the second direction (the Y-axis direction).

The second counter side wire 22BC includes a second end portion 22BCe of the second counter side wire 22BC and a second other end portion 22BCf of the second counter side wire 22BC. The direction from the second end portion 22BCe of the second counter side wire 22BC toward the second other end portion 22BCf of the second counter side wire 22BC is along the second direction (the Y-axis direction).

At the first time recited above, the first circuit 71 sets the potential of the second end portion 22Be of the second side wire 22B to be lower than the potential of the second other end portion 22Bf of the second side wire 22B. At the first time recited above, the first circuit 71 sets the potential of the second end portion 22BCe of the second counter side wire 22BC to be higher than the potential of the second other end portion 22BCf of the second counter side wire 22BC.

At the second time recited above, the first circuit 71 sets the potential of the second end portion 22Be of the second side wire 22B to be higher than the potential of the second other end portion 22Bf of the second side wire 22B. At the second time recited above, the first circuit 71 sets the potential of the second end portion 22BCe of the second counter side wire 22BC to be lower than the potential of the second other end portion 22BCf of the second counter side wire 22BC.

As shown in FIG. 17A and FIG. 17B, for example, the length L2 along the third direction of the second magnetic part 32 may be longer than the length LB2 along the third direction of the second side magnetic part 32B.

A sensor module 221 according to the embodiment (referring to FIG. 18A to FIG. 18C) includes, for example, the magnetic sensor 121 and the first circuit 71. The sensor module 221 may include the second circuit 72 and the third circuit 73.

FIG. 19A, FIG. 19B, FIG. 20A, and FIG. 20B are schematic views illustrating a portion of a magnetic sensor according to the second embodiment.

Figure 19A:
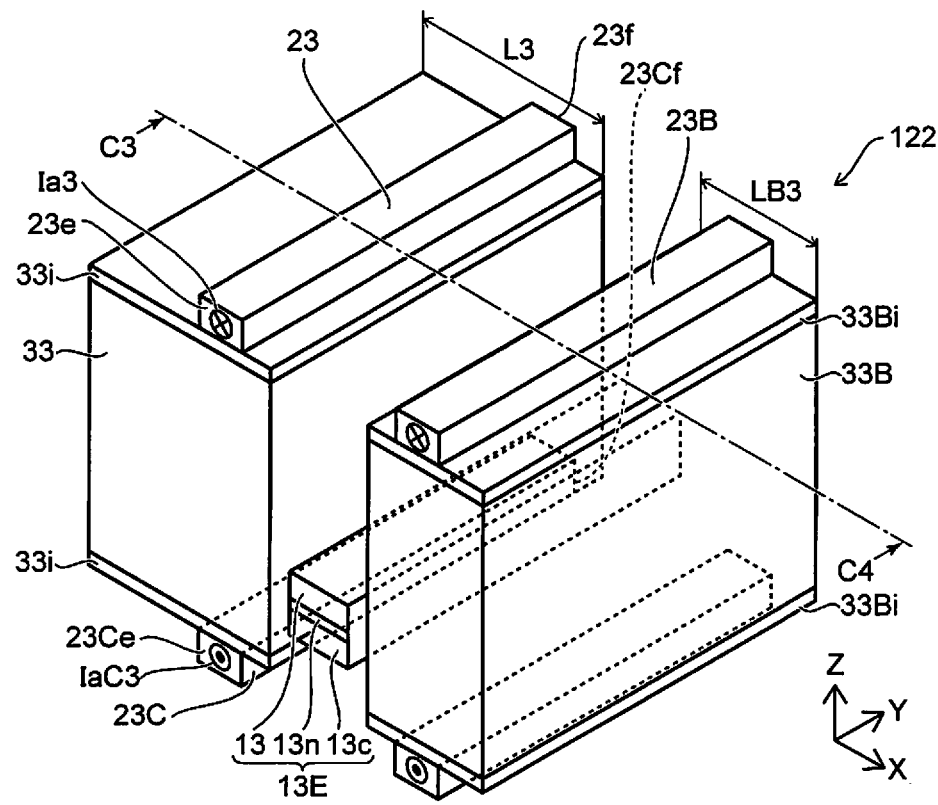
FIG. 19A and FIG. 19B are schematic views illustrating a portion of a magnetic sensor according to the second embodiment.
Figure 19B:
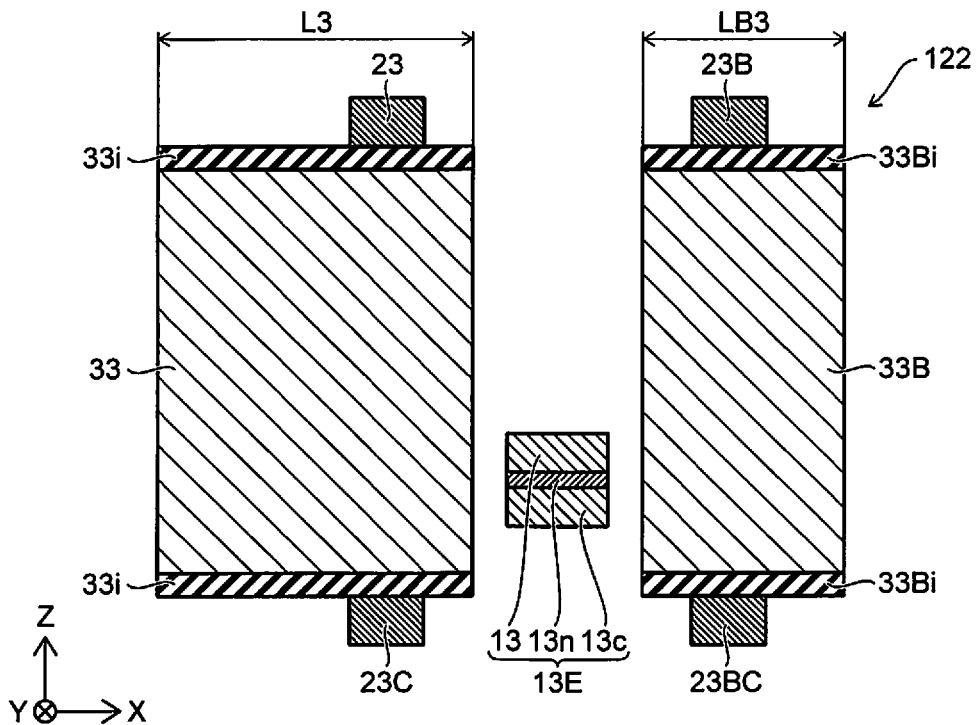
Figure 20A:
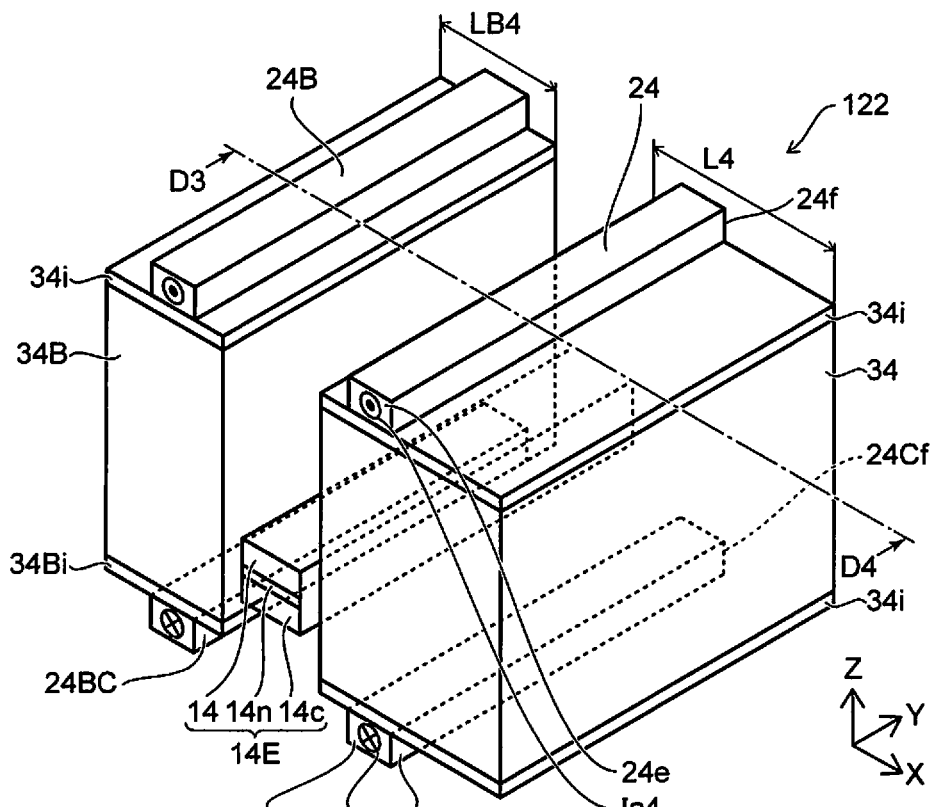
FIG. 20A and FIG. 20B are schematic views illustrating a portion of the magnetic sensor according to the second embodiment.
Figure 20B:
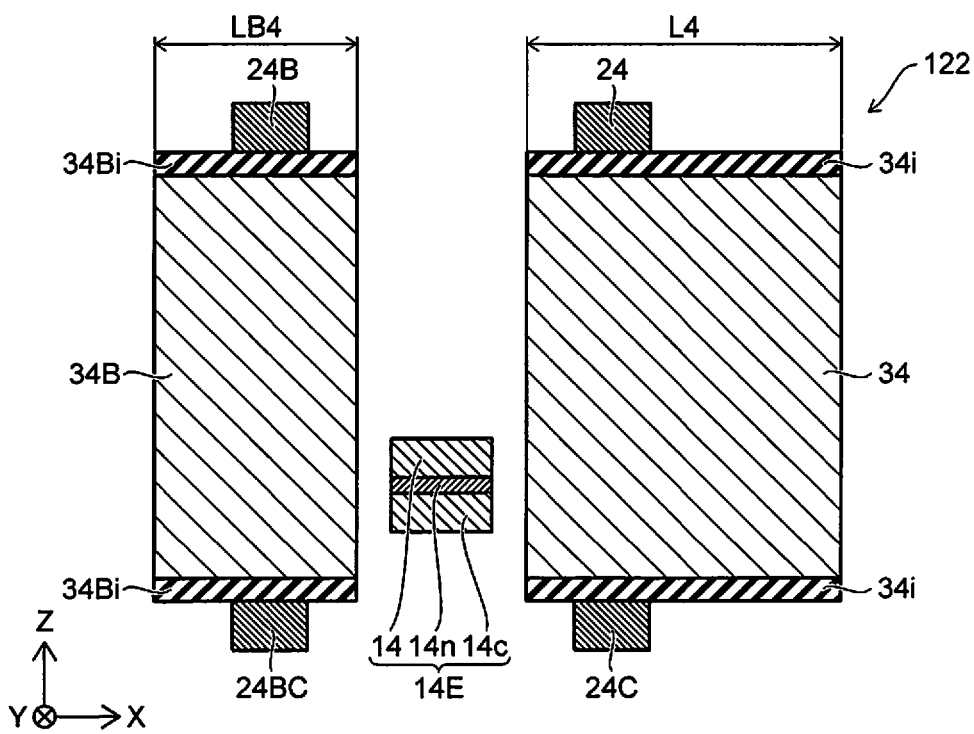

FIG. 19A is a perspective view. FIG. 19B is a line C3-C4 cross-sectional view of FIG. 19A. FIG. 20A is a perspective view. FIG. 20B is a line D3-D4 cross-sectional view of FIG. 20A.

Figure 21:
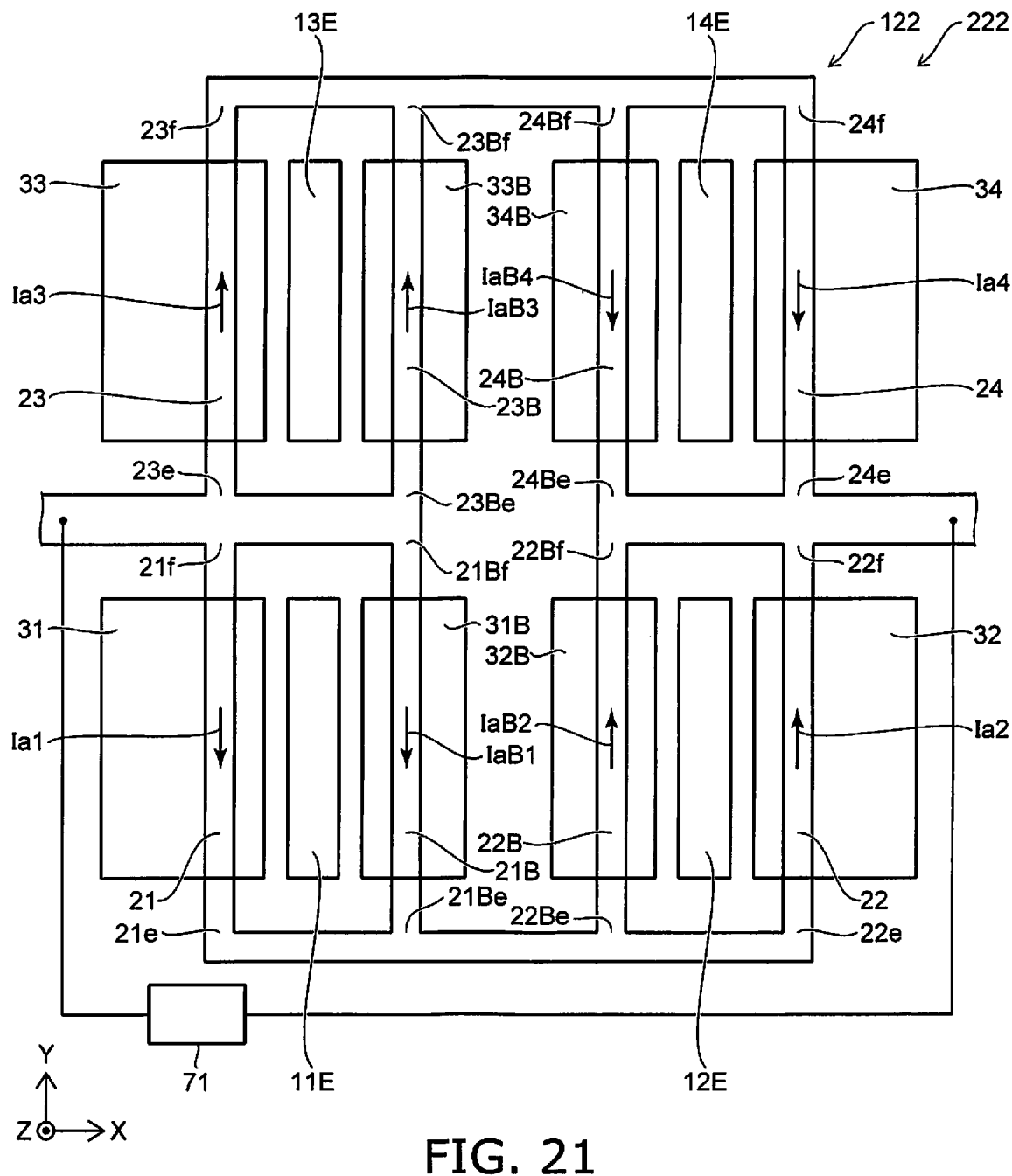
FIG. 21 is a schematic plan view illustrating the magnetic sensor according to the second embodiment.
Figure 22:
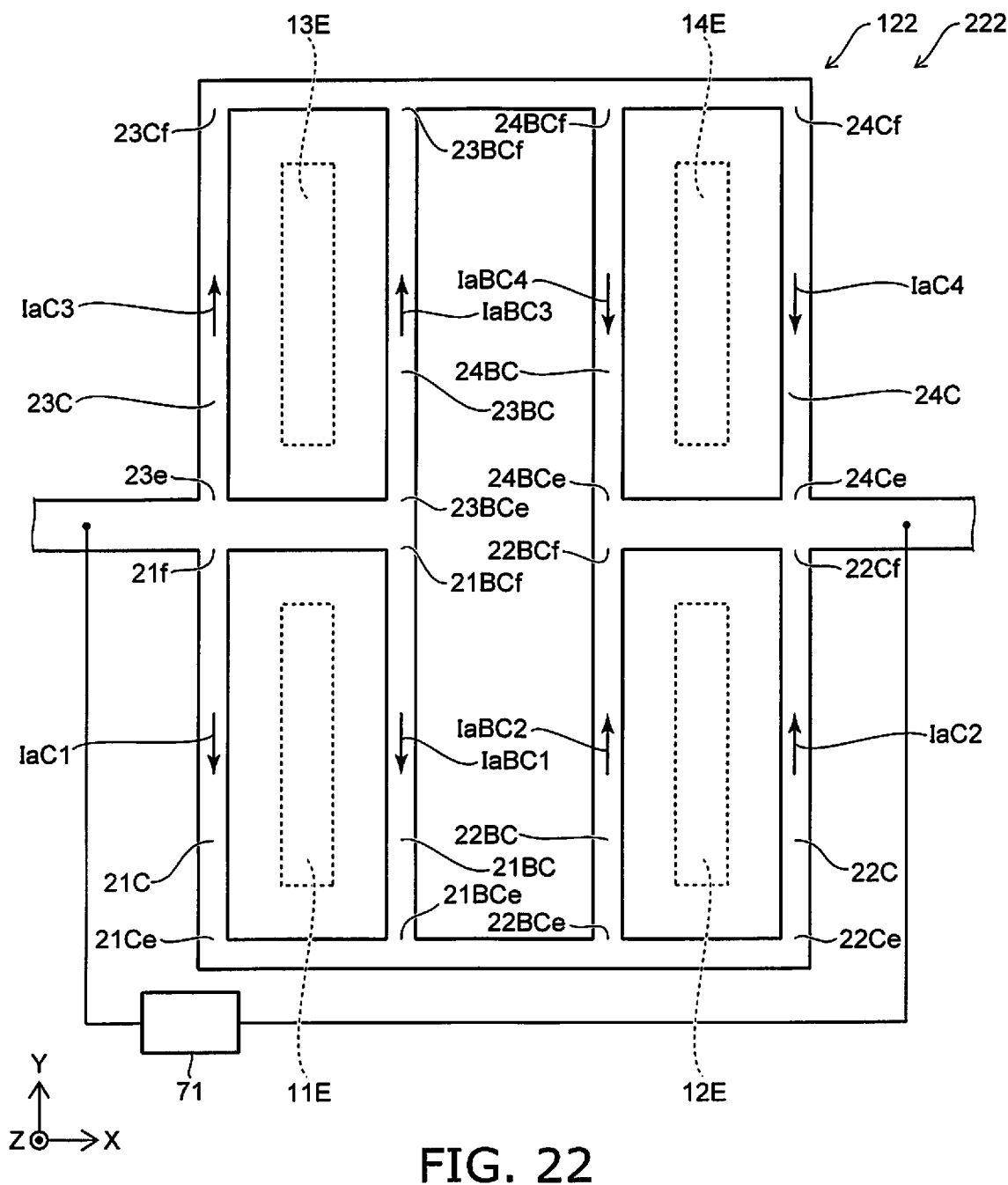
FIG. 22 is a schematic plan view illustrating the magnetic sensor according to the second embodiment.
Figure 23:
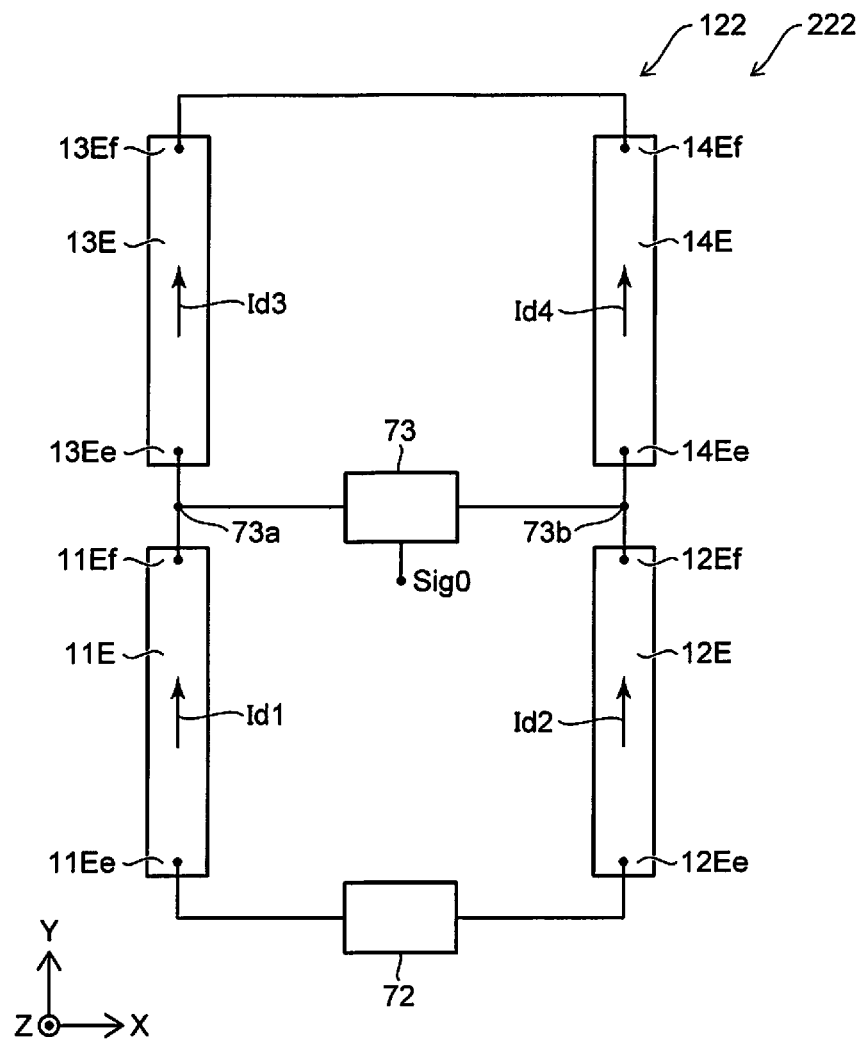
FIG. 23 is a schematic plan view illustrating the magnetic sensor according to the second embodiment.

FIG. 21 to FIG. 23 are schematic plan views illustrating the magnetic sensor according to the second embodiment.

A state in which the first magnetic part 31, etc., are removed is illustrated in FIG. 22 for easier viewing of the drawing.

The magnetic sensor 122 illustrated in FIG. 19A and FIG. 19B includes the third element 13E, the third wire 23, a third counter wire 23C, the third magnetic part 33, the fourth element 14E, the fourth wire 24, a fourth counter wire 24C, and the fourth magnetic part 34 in addition to the first element 11E, the first wire 21, the first counter wire 21C, the first magnetic part 31, the second element 12E, the second wire 22, the second counter wire 22C, and the second magnetic part 32 described above.

The configurations described in reference to the first wire 21, the first counter wire 21C, and the first magnetic part 31 are applicable to the third element 13E, the third wire 23, the third counter wire 23C, and the third magnetic part 33. The configurations described in reference to the second element 12E, the second wire 22, the second counter wire 22C, and the second magnetic part 32 are applicable to the fourth element 14E, the fourth wire 24, the fourth counter wire 24C, and the fourth magnetic part 34.

For example, these elements and these wires are connected as described in reference to FIG. 10 and FIG. 11 (referring to FIG. 21 to FIG. 23).

As shown in FIG. 19A, the first circuit 71 (referring to FIG. 15A and FIG. 15B) supplies the alternating current Ia3 to the third wire 23. The first circuit 71 supplies an alternating current IaC3 to the third counter wire 23C. The polarities (e.g., the phases) of these alternating currents are mutually-reversed.

For example, at the first time recited above, the first circuit 71 sets the potential of the third end portion 23e of the third wire 23 to be higher than the potential of the third other end portion 23f of the third wire 23. At the first time recited above, the first circuit 71 sets the potential of a third end portion 23Ce of the third counter wire 23C to be lower than the potential of a third other end portion 23Cf of the third counter wire 23C.

At the second time recited above, the first circuit 71 sets the potential of the third end portion 23e of the third wire 23 to be lower than the potential of the third other end portion 23f of the third wire 23. At the second time recited above, the first circuit 71 sets the potential of the third end portion 23Ce of the third counter wire 23C to be higher than the potential of the third other end portion 23Cf of the third counter wire 23C.

The magnetic sensor 122 may further include the third side wire 23B, a third counter side wire 23BC, and the third side magnetic part 33B.

The magnetic sensor 122 may include the insulating regions 33i and 33Bi. The length L3 along the third direction (the X-axis direction) of the third magnetic part 33 may be longer than the length LB3 along the third direction of the third side magnetic part 33B.

As shown in FIG. 20A, the first circuit 71 (referring to FIG. 15A and FIG. 15B) supplies the alternating current Ia4 to the fourth wire 24. The first circuit 71 supplies an alternating current IaC4 to the fourth counter wire 24C. The polarities (e.g., the phases) of these alternating currents are mutually-reversed.

For example, at the first time recited above, the first circuit 71 sets the potential of the fourth end portion 24e of the fourth wire 24 to be lower than the potential of the fourth other end portion 24f of the fourth wire 24. At the first time recited above, the first circuit 71 sets the potential of a fourth end portion 24Ce of the fourth counter wire 24C to be higher than the potential of a fourth other end portion 24Cf of the fourth counter wire 24C.

At the second time recited above, the first circuit 71 sets the potential of the fourth end portion 24e of the fourth wire 24 to be higher than the potential of the fourth other end portion 24f of the fourth wire 24. At the second time recited above, the first circuit 71 sets the potential of the fourth end portion 24Ce of the fourth counter wire 24C to be lower than the potential of the fourth other end portion 24Cf of the fourth counter wire 24C.

The magnetic sensor 122 may further include the fourth side wire 24B, a fourth counter side wire 24BC, and the fourth side magnetic part 34B.

The magnetic sensor 122 may include the insulating regions 34i and 34Bi. The length L4 along the third direction (the X-axis direction) of the fourth magnetic part 34 may be longer than the length LB4 along the third direction of the fourth side magnetic part 34B.

A sensor module 222 according to the embodiment (referring to FIG. 21 to FIG. 23) includes, for example, the magnetic sensor 122 and the first circuit 71. The sensor module 222 may include the second circuit 72 and the third circuit 73.

An example of a method for manufacturing the magnetic sensor according to the embodiment will now be described.

FIG. 24A to FIG. 24D and FIG. 25A to FIG. 25C are schematic cross-sectional views illustrating the method for manufacturing the magnetic sensor according to the embodiment.

Figure 24A:
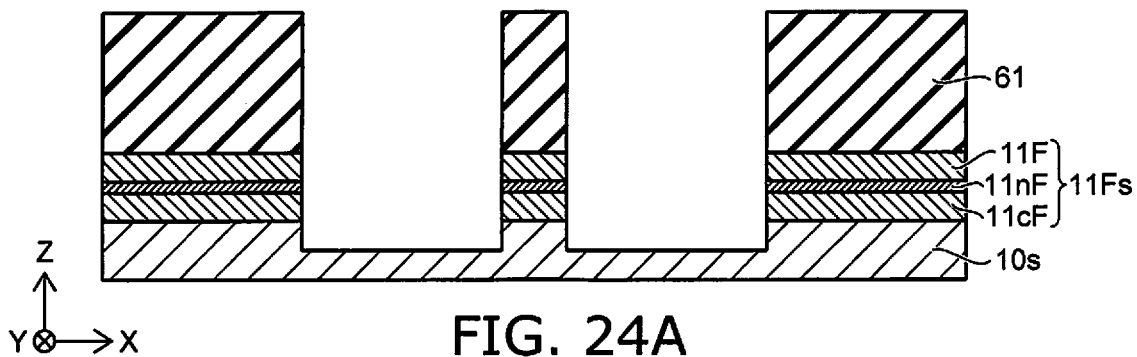
FIG. 24A to FIG. 24D are schematic cross-sectional views illustrating a method for manufacturing the magnetic sensor according to the embodiment.

As shown in FIG. 24A, a stacked film 11Fs is formed on a base body 10s; and a mask material 61 is formed on the stacked film 11Fs. The stacked film 11Fs includes a magnetic film 11cF used to form the first counter magnetic layer 11c, a nonmagnetic film 11nF used to form the first nonmagnetic layer 11n, and a magnetic film 11F used to form the first magnetic layer 11. An opening is provided in the mask material 61; and a portion of the stacked film 11Fs is removed using the mask material 61 as a mask. A portion of the base body 10s may be removed.

Figure 24B:
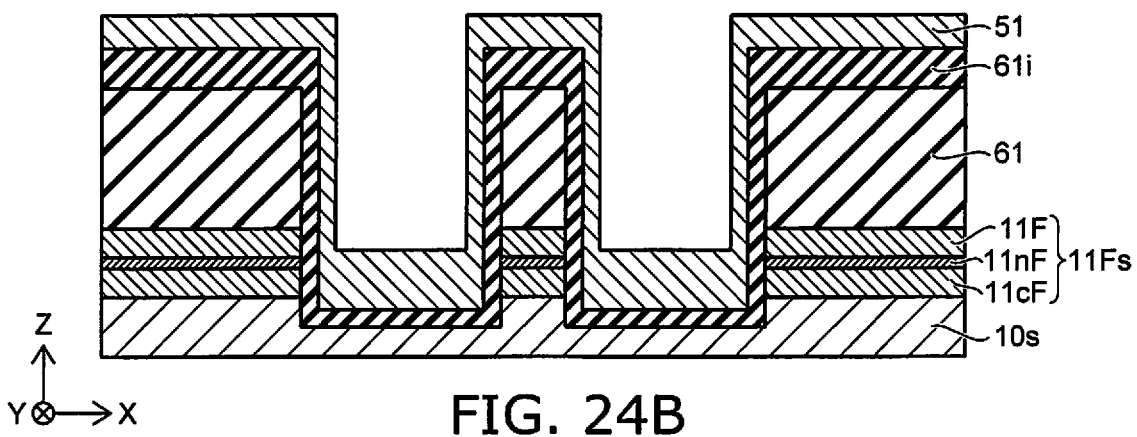

As shown in FIG. 24B, an insulating film 61i is formed; and a magnetic film 51 is formed on the insulating film 61i.

Figure 24C:
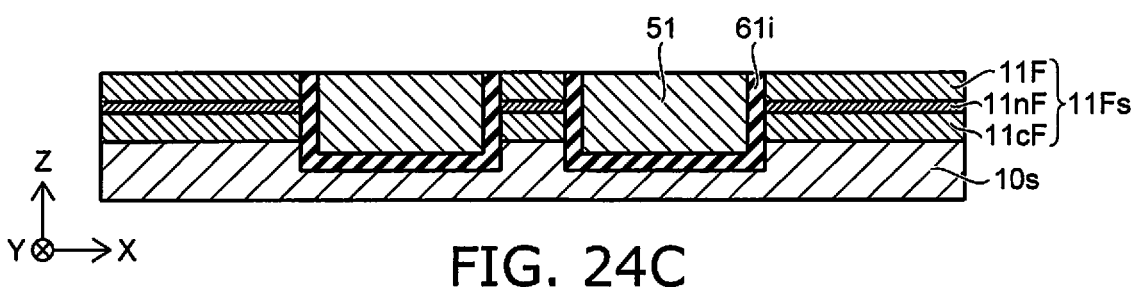

As shown in FIG. 24C, planarization is performed; and the stacked film 11Fs is exposed.

Figure 24D:
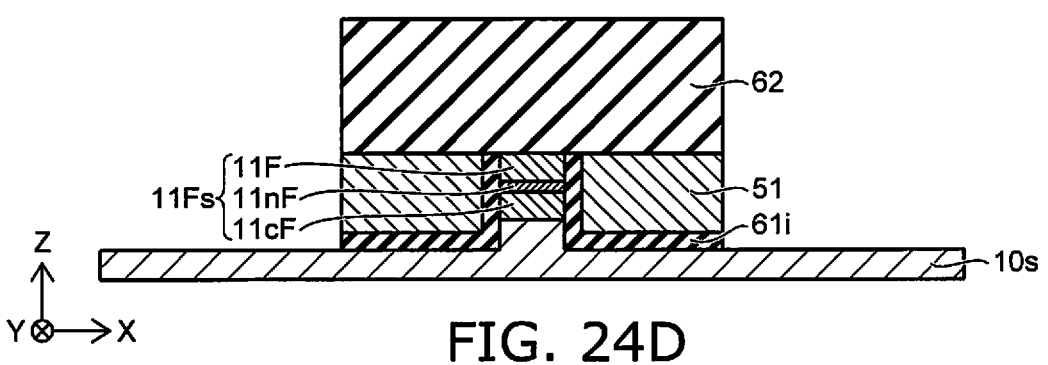

A mask material 62 is formed as shown in FIG. 24D. A portion of the stacked film 11Fs is removed via the opening of the mask material 62. For example, the remaining stacked film 11Fs is used to form the first element 11E. The mask material 62 is removed.

Figure 25A:
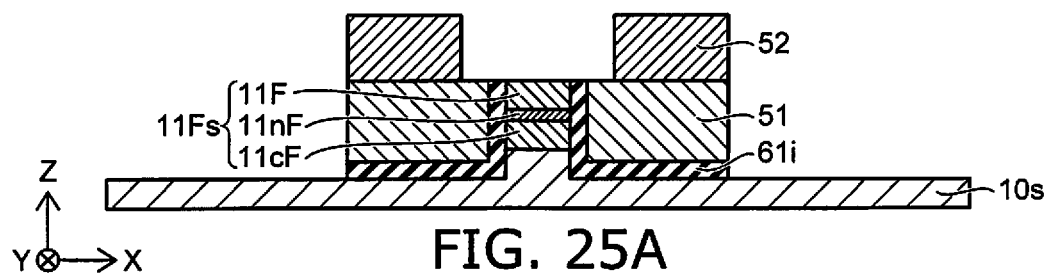
FIG. 25A to FIG. 25C are schematic cross-sectional views illustrating a method for manufacturing the magnetic sensor according to the embodiment.

As shown in FIG. 25A, another magnetic film 52 is formed on the remaining magnetic film 51.

Figure 25B:
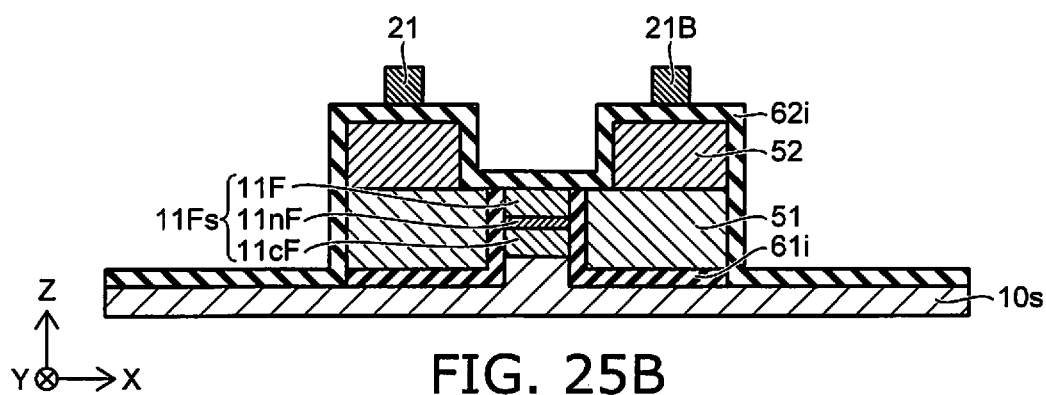

As shown in FIG. 25B, an insulating film 62i is formed; and the first wire 21 and the first side wire 21B are formed on the insulating film 62i.

Figure 25C:
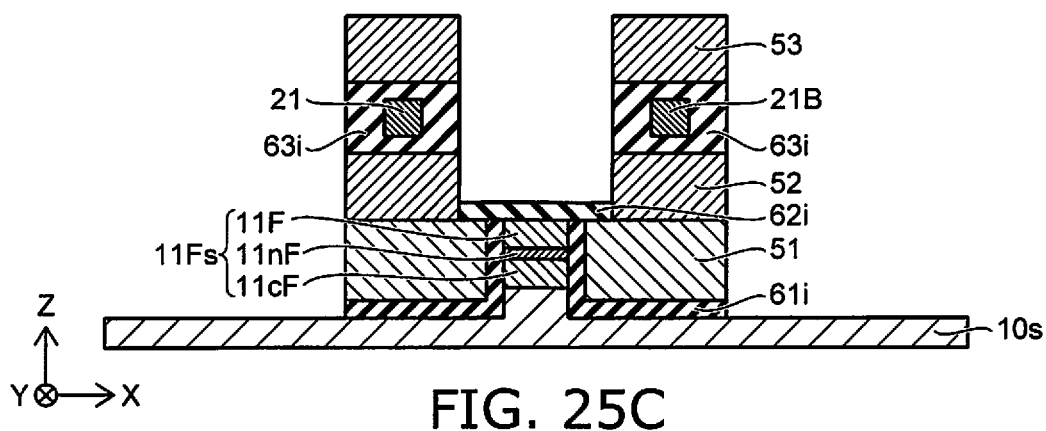

As shown in FIG. 25C, an insulating film 63i is formed on the first wire 21 and the first side wire 21B. A magnetic film 53 is formed on the insulating film 63i. For example, the first magnetic part 31 and the first side magnetic part 31B are obtained from the magnetic films 51, 52, and 53. Thus, for example, the magnetic sensor 113 illustrated in FIG. 9B is obtained.

In the embodiment, the magnetization is substantially fixed for one of the first magnetic layer 11 or the first counter magnetic layer 11c. The orientation of the magnetization changes for the other of the first magnetic layer 11 or the first counter magnetic layer 11c. The length along the Y-axis direction of the first element 11E is, for example, not less than 5 times (which may be, for example, not less than 10 times) the length along the X-axis direction of the first element 11E.

The first element 11E may include, for example, an antiferromagnetic film (an IrMn film, etc.). The first element 11E may include a nonmagnetic film (e.g., a Ru film), etc. For example, the nonmagnetic film is provided between the antiferromagnetic film and one of the first magnetic layer 11 or the first counter magnetic layer 11c.

The first element 11E may include a foundation layer. The foundation layer may include, for example, at least one selected from the group consisting of Ta, Ru, Hf, and NiFeCr. For example, good crystallinity is obtained. For example, a large crystal grain size is easier to obtain. For example, a crystal orientation in the film surface perpendicular direction is easier to obtain. The other of the first magnetic layer 11 or the first counter magnetic layer 11c (e.g., a free layer) may include, for example, at least one selected from the group consisting of a CoFe alloy, a NiFe alloy, and a CoFeNi alloy. The other of the first magnetic layer 11 or the first counter magnetic layer 11c may include a stacked film including a CoFe film and a NiFe film.

In one example, the first nonmagnetic layer 11n includes, for example, a Cu film.

In another example, the first nonmagnetic layer 11n may include MgO. The thickness of the MgO film is, for example, not less than 0.5 nm and not more than 2 nm. The first nonmagnetic layer 11n may include $Al_2O_3$. The first nonmagnetic layer 11n may have, for example, a crystal structure of a NaCl structure. The first nonmagnetic layer 11n may include $MgAl_2O_4$. The first nonmagnetic layer 11n may include a spinel material.

The first magnetic part 31 includes, for example, at least one selected from the group consisting of NiFe and CoZrNb. For example, a Ta film or the like may be provided as the foundation layer of the first magnetic part 31. The thickness of the Ta film is, for example, not less than about 3 nm and not more than 10 nm. By providing such a foundation layer, for example, the crystal orientation of the first magnetic part 31 easily can be isotropic even in the case where the thickness of the first magnetic part 31 is thick (e.g., 100 nm or more). For example, isotropy of the magnetization direction is obtained.

Such a configuration of the first element 11E is applicable to the second to fourth elements 12E to 13E.

At least one of the second to fourth magnetic parts 32 to 34 or the first to fourth side magnetic parts 31B to 34B includes the materials described in reference to the first magnetic part 31.

At least one of the first to fourth wires 21 to 24, the first to fourth side wires 21B to 24B, the first to fourth counter wires 21C to 24C, or the first to fourth counter side wires 21BC to 24BC includes at least one selected from the group consisting of Cu, Al, and Au.

At least one of the first to fourth magnetic layers 11 to 14 or the first to fourth counter magnetic layers 11c to 14c includes, for example, at least one selected from the group consisting of Fe, Co, and Ni.

According to the embodiment, for example, the size of the magnetic sensor can be small. For example, the resolution can be increased. For example, the alternating-current magnetic fields due to the alternating currents are applied effectively to the elements. The loss of the alternating current can be suppressed. For example, the power consumption can be reduced.

An application example of the magnetic sensor according to the embodiment will now be described.

Third Embodiment

For example, the magnetic sensor according to the embodiment is applicable to a diagnostic device, etc.

Figure 26:
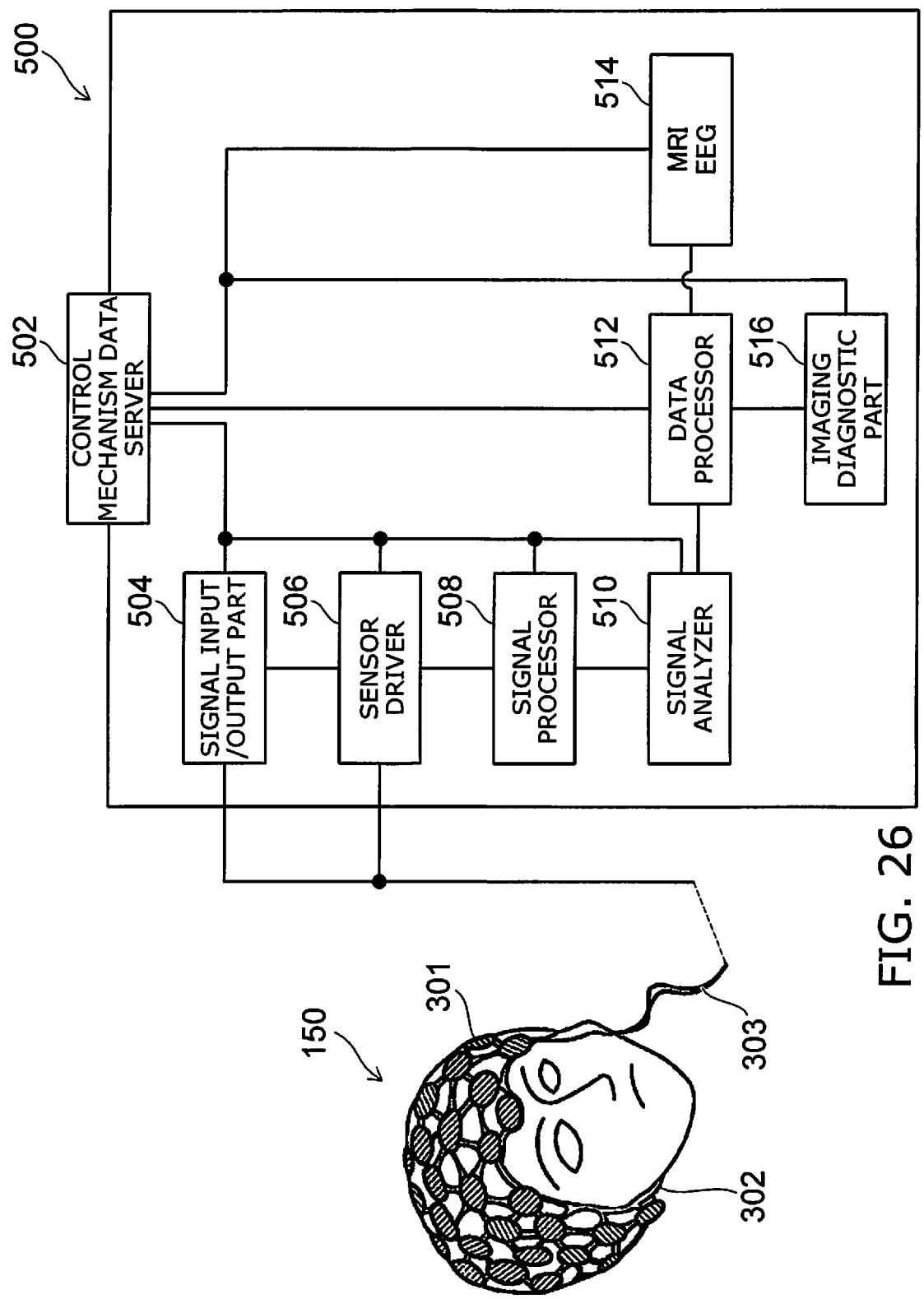
FIG. 26 is a schematic view showing a magnetic sensor and a diagnostic device according to a third embodiment.

FIG. 26 is a schematic view showing the magnetic sensor and the diagnostic device according to the third embodiment.

As shown in FIG. 26, the diagnostic device 500 includes the magnetic sensor 150. The magnetic sensor 150 includes the magnetic sensors (and the magnetic sensor devices) described in reference to the first embodiment and the second embodiment and modifications of the magnetic sensors (and the magnetic sensor devices).

In the diagnostic device 500, the magnetic sensor 150 is, for example, a magnetoencephalograph device. The magnetoencephalograph device detects a magnetic field generated by cranial nerves. In the case where the magnetic sensor 150 is included in a magnetoencephalograph device, the size of the magnetic element included in the magnetic sensor 150 is, for example, not less than 1 mm and less than 10 mm. The size is, for example, the length including the MFC.

As shown in FIG. 26, the magnetic sensor 150 (the magnetoencephalograph device) is mounted to, for example, the head of a human body. The magnetic sensor 150 (the magnetoencephalograph device) includes a sensor part 301. The sensor part 301 includes, for example, the magnetic sensor according to the first embodiment or the second embodiment.

The magnetic sensor 150 (the magnetoencephalograph device) may include multiple sensor parts 301. The number of the multiple sensor parts 301 is, for example, about 100 (e.g., not less than 50 and not more than 150). The multiple sensor parts 301 are provided in a base body 302 that is pliable.

The magnetic sensor 150 may include, for example, a circuit for differential detection, etc. The magnetic sensor 150 may include a sensor other than a magnetic sensor (e.g., a potential terminal, an acceleration sensor, etc.).

The size of the magnetic sensor 150 (the magnetic sensor described in reference to the first embodiment and the second embodiment) is small compared to the size of a conventional SQUID magnetic sensor. Therefore, the mounting of the multiple sensor parts 301 is easy. The mounting of the multiple sensor parts 301 and the other circuits is easy. It is easy for the multiple sensor parts 301 to coexist with the other sensors.

The base body 302 may include, for example, an elastic body such as a silicone resin, etc. For example, the multiple sensor parts 301 are linked to each other and provided in the base body 302. For example, the base body 302 can be closely adhered to the head.

An input/output wire 303 of the sensor part 301 is connected to a sensor driver 506 and a signal input/output part 504 of the diagnostic device 500. Magnetic field measurement is performed in the sensor part 301 based on the electrical power from the sensor driver 506 and the control signal from the signal input/output part 504. The result is input to the signal input/output part 504. The signal that is obtained by the signal input/output part 504 is supplied to a signal processor 508. Processing such as, for example, the removal of noise, filtering, amplification, signal calculation, etc., are performed in the signal processor 508. The signal that is processed by the signal processor 508 is supplied to a signal analyzer 510. For example, the signal analyzer 510 extracts a designated signal for magnetoencephalography. For example, signal analysis to match the signal phases is performed in the signal analyzer 510.

The output of the signal analyzer 510 (the data for which the signal analysis has ended) is supplied to a data processor 512. Data analysis is performed in the data processor 512. It is possible to include image data such as, for example, MRI (Magnetic Resonance Imaging), etc., in the data analysis. It is possible to include, for example, scalp potential information such as an EEG (Electroencephalogram), etc., in the data analysis. For example, nerve firing point analysis, inverse analysis, or the like is performed by the data analysis.

For example, the result of the data analysis is supplied to an imaging diagnostic part 516. Imaging is performed by the imaging diagnostic part 516. The diagnosis is supported by the imaging.

For example, the series of operations recited above is controlled by a control mechanism 502. For example, necessary data such as preliminary signal data, metadata partway through the data processing, or the like is stored in a data server. The data server and the control mechanism may be integrated.

The diagnostic device 500 according to the embodiment includes the magnetic sensor 150, and a processor that processes the signal obtained from the magnetic sensor 150. The processor includes, for example, at least one of the signal processor 508 or the data processor 512. The processor includes, for example, a computer, etc.

In the magnetic sensor 150 shown in FIG. 26, the sensor part 301 is mounted to the head of a human body. The sensor part 301 may be mounted to the chest of the human body. Magnetocardiography is possible thereby. For example, the sensor part 301 may be mounted to the abdomen of a pregnant woman. Palmoscopy of the fetus can be performed thereby.

It is favorable for the magnetic sensor device including the participant to be mounted inside a shielded room. For example, the effects of geomagnetism or magnetic noise can be suppressed thereby.

For example, a mechanism may be provided to locally shield the sensor part 301 or the measurement section of the human body. For example, a shield mechanism may be provided in the sensor part 301. For example, the signal analysis or the data processing may be effectively shielded.

In the embodiment, the base body 302 may be pliable or substantially may not be pliable. In the example shown in FIG. 26, the base body 302 is a continuous film that is patterned into a hat-like configuration. The base body 302 may have a net configuration. For example, good wearability is obtained thereby. For example, the adhesion of the base body 302 with the human body improves. The base body 302 may have a hard helmet-like configuration.

Figure 27:
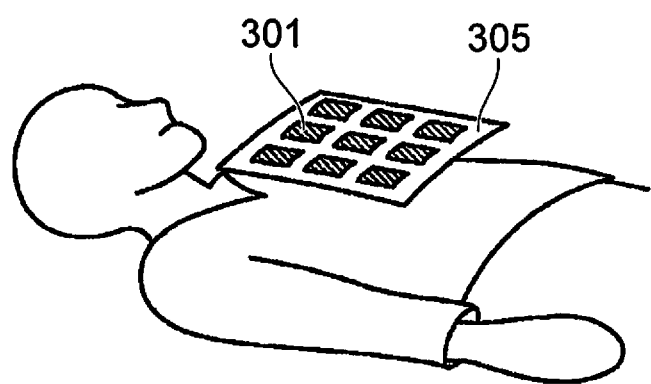
FIG. 27 is a schematic view showing another magnetic sensor according to a fourth embodiment.

FIG. 27 is a schematic view showing another magnetic sensor according to a fourth embodiment.

In the example shown in FIG. 27, the sensor part 301 is provided on a hard base body 305 having a flat plate configuration.

The input and output of the signal obtained from the sensor part 301 in the example shown in FIG. 27 is similar to the input and output described in reference to FIG. 26. The processing of the signal obtained from the sensor part 301 in the example shown in FIG. 27 is similar to the processing described in reference to FIG. 26.

There is a reference example in which a SQUID (Superconducting Quantum Interference Device) magnetic sensor is used as a device to measure a faint magnetic field such as a magnetic field generated from a living body, etc. Because superconductivity is used in the reference example, the device is large; and the power consumption is large. The burden on the measurement object (the patient) is large.

According to the embodiment, the device can be small. The power consumption can be suppressed. The burden on the measurement object (the patient) can be reduced. According to the embodiment, the SN ratio of the magnetic field detection can be improved. The detection sensitivity can be increased.

The embodiments may include the following configurations (e.g., technological proposals).

Configuration 1

A magnetic sensor, comprising:

a first element including a first magnetic layer, a first counter magnetic layer, and a first nonmagnetic layer provided between the first magnetic layer and the first counter magnetic layer, a direction from the first counter magnetic layer toward the first magnetic layer being along a first direction;

a first wire extending in a second direction crossing the first direction; and a first magnetic part including a first region and a first counter region, at least a portion of the first wire being between the first region and the first counter region in the first direction.

Configuration 2

The magnetic sensor according to Configuration 1, wherein a third direction from the first region toward the first element crosses a plane including the first direction and the second direction.

Configuration 3

The magnetic sensor according to Configuration 2, wherein the first magnetic part further includes a first side region and a first counter side region, and the at least a portion of the first wire is between the first side region and the first counter side region in the third direction.

Configuration 4

The magnetic sensor according to Configuration 1 or 2, further comprising:

a first side wire extending in the second direction; and a first side magnetic part, the first side magnetic part including a first region of the first side magnetic part and a first counter region of the first side magnetic part, at least a portion of the first side wire being between the first region of the first side magnetic part and the first counter region of the first side magnetic part in the first direction, a position of the first element in a third direction being between a position in the third direction of the first wire and a position in the third direction of the first side wire, the third direction being from the first region toward the first element.

Configuration 5

The magnetic sensor according to Configuration 4, wherein the first magnetic part further includes a first side region of the first magnetic part and a first counter side region of the first magnetic part, the at least a portion of the first wire is between the first side region of the first magnetic part and the first counter side region of the first magnetic part in the third direction, the first side magnetic part further includes a first side region of the first side magnetic part and a first counter side region of the first side magnetic part, the at least a portion of the first side wire is between the first side region of the first side magnetic part and the first counter side region of the first side magnetic part in the third direction, a position in the third direction of the first counter side region of the first magnetic part is between a position in the third direction of the first side region of the first magnetic part and a position in the third direction of the first side region of the first side magnetic part, and a position in the third direction of the first counter side region of the first side magnetic part is between the position in the third direction of the first counter side region of the first magnetic part and a position in the third direction of the first side region of the first side magnetic part.

Configuration 6

The magnetic sensor according to Configuration 4 or 5, wherein a length along the third direction of the first magnetic part is longer than a length along the third direction of the first side magnetic part.

Configuration 7

The magnetic sensor according to any one of Configurations 4 to 6, further comprising a first circuit, the first wire including a first end portion of the first wire and a first other end portion of the first wire, a direction from the first end portion of the first wire toward the first other end portion of the first wire being along the second direction, the first side wire including a first end portion of the first side wire and a first other end portion of the first side wire, a direction from the first end portion of the first side wire toward the first other end portion of the first side wire being along the second direction, a direction from the first end portion of the first wire toward the first end portion of the first side wire being along the third direction, a direction from the first other end portion of the first wire toward the first other end portion of the first side wire being along the third direction, the first end portion of the first wire and the first end portion of the first side wire being electrically connected to each other, the first other end portion of the first wire and the first other end portion of the first side wire being electrically connected to each other, the first circuit being electrically connected to the first end portion of the first wire and the first other end portion of the first wire and supplying an alternating current to the first wire and the first side wire.

Configuration 8

The magnetic sensor according to any one of Configurations 1 to 6, further comprising:

a second element;

a second wire; and a second magnetic part, the second element including a second magnetic layer, a second counter magnetic layer, and a second nonmagnetic layer provided between the second magnetic layer and the second counter magnetic layer, a direction from the second counter magnetic layer toward the second magnetic layer being along the first direction, the second wire extending in the second direction, the second magnetic part including a second region and a second counter region, at least a portion of the second wire being between the second region and the second counter region in the first direction.

Configuration 9

The magnetic sensor according to Configuration 8, further comprising:

a second side wire extending in the second direction; and a second side magnetic part, the second side magnetic part including a second region of the second side magnetic part and a second side region of the second side magnetic part, at least a portion of the second side wire being between the second region of the second side magnetic part and the second side region of the second side magnetic part in the first direction, a a position in the third direction of the second element being between a position in the third direction of the second wire and a position in the third direction of the second side wire.

Configuration 10

The magnetic sensor according to Configuration 9, wherein a length along the third direction of the second magnetic part is longer than a length along the third direction of the second side magnetic part.

Configuration 11

The magnetic sensor according to Configuration 9 or 10, further comprising a first circuit, the first wire including a first end portion of the first wire and a first other end portion of the first wire, a direction from the first end portion of the first wire toward the first other end portion of the first wire being along the second direction, the first side wire including a first end portion of the first side wire and a first other end portion of the first side wire, a direction from the first end portion of the first side wire toward the first other end portion of the first side wire being along the second direction, a direction from the first end portion of the first wire toward the first end portion of the first side wire being along the third direction, a direction from the first other end portion of the first wire toward the first other end portion of the first side wire being along the third direction, the first end portion of the first wire and the first end portion of the first side wire being electrically connected to each other, the first other end portion of the first wire and the first other end portion of the first side wire being electrically connected to each other, the second wire including a second end portion of the second wire and a second other end portion of the second wire, a direction from the second end portion of the second wire toward the second other end portion of the second wire being along the second direction, the second side wire including a second end portion of the second side wire and a second other end portion of the second side wire, a direction from the second end portion of the second side wire toward the second other end portion of the second side wire being along the second direction, a direction from the second end portion of the second side wire toward the second end portion of the second wire being along the third direction, a direction from the second other end portion of the second side wire toward the second other end portion of the second wire being along the third direction, the second end portion of the second wire and the second end portion of the second side wire being electrically connected to each other, the second other end portion of the second wire and the second other end portion of the second side wire being electrically connected to each other, the second end portion of the second wire being electrically connected to the first end portion of the first wire, the first circuit being electrically connected to the first other end portion of the first wire and the second other end portion of the second wire and supplying an alternating current to the first wire, the first side wire, the second wire, and the second side wire.

Configuration 12

The magnetic sensor according to Configuration 11, further comprising a second circuit applying a direct current voltage to the first element and the second element.

Configuration 13

The magnetic sensor according to Configuration 12, further comprising a third circuit, the first element and the second element being connected in series to each other, the third circuit detecting a potential of a connection point between the first element and the second element.

Configuration 14

The magnetic sensor according to Configuration 11, further comprising:

a third element;

a fourth element;

a third wire;

a fourth wire;

a third magnetic part; and a fourth magnetic part, the third element including a third magnetic layer, a third counter magnetic layer, and a third nonmagnetic layer provided between the third magnetic layer and the third counter magnetic layer, a direction from the third counter magnetic layer toward the third magnetic layer being along the first direction, the third wire extending in the second direction, the third magnetic part including a third region and a third counter region, at least a portion of the third wire being between the third region and the third counter region in the first direction, the fourth element including a fourth magnetic layer, a fourth counter magnetic layer, and a fourth nonmagnetic layer provided between the fourth magnetic layer and the fourth counter magnetic layer, a direction from the fourth counter magnetic layer toward the fourth magnetic layer being along the first direction, the fourth wire extending in the second direction, the fourth magnetic part including a fourth region and a fourth counter region, at least a portion of the fourth wire being between the fourth region and the fourth counter region in the first direction, the third wire including a third end portion of the third wire and a third other end portion of the third wire, a direction from the third end portion of the third wire toward the third other end portion of the third wire being along the second direction, the fourth wire including a fourth end portion of the fourth wire and a fourth other end portion of the fourth wire, a direction from the fourth end portion of the fourth wire toward the fourth other end portion of the fourth wire being along the second direction, the third other end portion of the third wire being electrically connected to the fourth other end portion of the fourth wire, the third end portion of the third wire being electrically connected to the first other end portion of the first wire, the fourth end portion of the fourth wire being electrically connected to the second other end portion of the second wire.

Configuration 15

The magnetic sensor according to Configuration 14, further comprising:
 a third side wire extending in the second direction;
 a third side magnetic part;
 a fourth side wire extending in the second direction; and
 a fourth side magnetic part,
 the third side magnetic part including a third region of the third side magnetic part and a third counter region of the third side magnetic part,
 at least a portion of the third side wire being between the third region of the third side magnetic part and the third counter region of the third side magnetic part in the first direction,
 a position in the third direction of the third element being between a position in the third direction of the third wire and a position in the third direction of the third side wire,
 the fourth side magnetic part including a fourth region of the fourth side magnetic part and a fourth counter region of the fourth side magnetic part,
 at least a portion of the fourth side wire being between the fourth region of the fourth side magnetic part and the fourth counter region of the fourth side magnetic part in the first direction,
 a position in the third direction of the fourth element being between a position in the third direction of the fourth wire and a position in the third direction of the fourth side wire,
 a length along the third direction of the third magnetic part being longer than a length along the third direction of the third side magnetic part,
 a length along the third direction of the fourth magnetic part being longer than a length along the third direction of the fourth side magnetic part.

Configuration 16

The magnetic sensor according to Configuration 14 or 15, further comprising a second circuit,
 the second circuit applying a direct current voltage to the first to fourth elements.

Configuration 17

The magnetic sensor according to Configuration 16, further comprising a third circuit,
 the first element and the third element being connected in series to each other,
 the second element and the fourth element being connected in series to each other,
 the third circuit detecting a potential between a connection point between the first element and the second element and a connection point between the second element and the fourth element.

Configuration 18

A magnetic sensor, comprising:
 a first element including a first magnetic layer, a first counter magnetic layer, and a first nonmagnetic layer provided between the first magnetic layer and the first counter magnetic layer, a direction from the first counter magnetic layer toward the first magnetic layer being along a first direction;
 a first wire extending in a second direction crossing the first direction;
 a first counter wire extending in the second direction; and
 a first magnetic part provided between the first wire and the first counter wire in the first direction.

Configuration 19

The magnetic sensor according to Configuration 18, further comprising a first circuit,
 the first wire including a first end portion of the first wire and a first other end portion of the first wire, a direction from the first end portion of the first wire toward the first other end portion of the first wire being along the second direction,
 the first counter wire including a first end portion of the first counter wire and a first other end portion of the first counter wire, a direction from the first end portion of the first counter wire toward the first other end portion of the first counter wire being along the second direction,
 a direction from the first end portion of the first counter wire toward the first end portion of the first wire being along the first direction,
 a direction from the first other end portion of the first counter wire toward the first other end portion of the first wire being along the first direction,
 at a first time, the first circuit setting a potential of the first end portion of the first wire to be lower than a potential of the first other end portion of the first wire and setting a potential of the first end portion of the first counter wire to be higher than a potential of the first other end portion of the first counter wire,
 at a second time, the first circuit setting the potential of the first end portion of the first wire to be higher than the potential of the first other end portion of the first wire and setting the potential of the first end portion of the first counter wire to be lower than the potential of the first other end portion of the first counter wire.

Configuration 20

The magnetic sensor according to Configuration 19, further comprising:
 a second element;
 a second wire;
 a second counter wire; and
 a second magnetic part,
 the second element including a second magnetic layer, a second counter magnetic layer, and a second nonmagnetic layer provided between the second magnetic layer and the second counter magnetic layer, a direction from the second counter magnetic layer toward the second magnetic layer being along the first direction,
 the second wire extending in the second direction,
 the second counter wire extending in the second direction,
 the second magnetic part being provided between the second wire and the second counter wire in the first direction,
 the second wire including a second end portion of the second wire and a second other end portion of the second wire, a direction from the second end portion of the second wire toward the second other end portion of the second wire being along the second direction,
 the second counter wire including a second end portion of the second counter wire and a second other end portion of the second counter wire, a direction from the second end portion of the second counter wire toward the second other end portion of the second counter wire being along the second direction, a direction from the second end portion of the second counter wire toward the second end portion of the second wire being along the first direction, a direction from the second other end portion of the second counter wire toward the second other end portion of the second wire being along the first direction, at the first time, the first circuit setting a potential of the second end portion of the second wire to be higher than a potential of the second other end portion of the second wire and setting a potential of the second end portion of the second counter wire to be lower than a potential of the second other end portion of the second counter wire, at the second time, the first circuit setting the potential of the second end portion of the second wire to be lower than the potential of the second other end portion of the second wire and setting the potential of the second end portion of the second counter wire to be higher than the potential of the second other end portion of the second counter wire.

Configuration 21

A sensor module, comprising:
the magnetic sensor according to any one of Configurations 1 to 3; and
a first circuit,
the first circuit being electrically connected to the first wire and supplying an alternating current to the first wire.

Configuration 22

A sensor module, comprising:
the magnetic sensor according to Configuration 18; and
a first circuit,
the first circuit being electrically connected to the first wire and the first counter wire and supplying an alternating current to the first wire and the first counter wire.

Configuration 23

A diagnostic device, comprising:
the magnetic sensor according to any one of Configurations 1 to 20; and
a processor processing a signal obtained from the magnetic sensor.

The embodiments may include the following configurations (e.g., technological proposals). For example, the first to fourth alternating currents correspond to the alternating currents Ia1 to Ia4. For example, the first to fourth element currents correspond to the currents Id1 to Id4.

Configuration A1

A magnetic sensor, comprising:
a first element including a first magnetic layer;
a second element including a second magnetic layer;
a first wire;
a second wire;
a first circuit electrically connected to the first wire and the second wire; and
a second circuit electrically connected to the first element and the second element,
the first circuit supplying a first alternating current to the first wire and supplying a second alternating current to the second wire,
the second circuit supplying a first element current to the first element and supplying a second element current to the second element,
at a first time, the first alternating current having a first alternating current orientation, and the second alternating current having a second alternating current orientation,
at a second time, the first alternating current having a reverse orientation of the first alternating current orientation, and the second alternating current having a reverse orientation of the second alternating current orientation, at the first time, the first element current having a first element current orientation, and the second element current having a second element current orientation, at the second time, the first element current having the first element current orientation, and the second element current having the second element current orientation, the first alternating current orientation having a component in an orientation of the first element current, the second alternating current orientation having a component in a reverse orientation of an orientation of the second element current.

Configuration A2

The magnetic sensor according to Configuration A1, wherein a distance between the first wire and the first element is shorter than a distance between the first wire and the second element, a distance between the second wire and the second element is shorter than a distance between the second wire and the first element, the first wire includes a first wire end portion and a second wire end portion, the second wire includes a third wire end portion and a fourth wire end portion, an orientation from the third wire end portion toward the fourth wire end portion is along an orientation from the first wire end portion toward the second wire end portion, at the first time, the first alternating current has the orientation from the first wire end portion toward the second wire end portion, and at the first time, the first alternating current has an orientation from the fourth wire end portion toward the third wire end portion.

Configuration A3

The magnetic sensor according to Configuration A1, wherein the first element and the second element are electrically connected in series.

Configuration A4

The magnetic sensor according to Configuration A3, further comprising a third circuit, the first element including a first element end portion and a second element end portion, the second element including a third element end portion and a fourth element end portion, the second element end portion and the fourth element end portion being electrically connected to each other, the second circuit being electrically connected to the first element end portion and the third element end portion, the third circuit being electrically connected to the second element end portion and the fourth element end portion, the third circuit outputting a signal corresponding to a change of a potential of the second element end portion and the fourth element end portion.

Configuration A5

The magnetic sensor according to Configuration A4, wherein the first alternating current and the second alternating current have a first frequency, and the signal corresponds to a component of the first frequency of the change of the potential of the second element end portion and the fourth element end portion.

Configuration A6

The magnetic sensor according to Configuration A1 or A2, further comprising:
a first resistance part; and
a second resistance part, the first element including a first element end portion and a second element end portion, the second element including a third element end portion and a fourth element end portion, the second element end portion and the fourth element end portion being electrically connected to each other, the first resistance part including a first resistance end portion and a second resistance end portion, the second resistance part including a third resistance end portion and a fourth resistance end portion, the second resistance end portion and the first element end portion being electrically connected to each other, the fourth resistance end portion and the third element end portion being electrically connected to each other, the second circuit being electrically connected to the first resistance end portion, the third resistance end portion, the second element end portion, and the fourth element end portion, the second circuit supplying the first element current to a set of the first resistance part and the first element and supplying the second element current to a set of the second resistance part and the second element.

Configuration A7

The magnetic sensor according to Configuration A6, further comprising a third circuit, the third circuit outputting a signal corresponding to a difference between a potential of the first element end portion and a potential of the third element end portion.

Configuration A8

The magnetic sensor according to Configuration A7, wherein the first resistance part includes a third magnetic layer, a third counter magnetic layer, and a third nonmagnetic layer provided between the third magnetic layer and the third counter magnetic layer, and the second resistance part includes a fourth magnetic layer, a fourth counter magnetic layer, and a fourth nonmagnetic layer provided between the fourth magnetic layer and the fourth counter magnetic layer.

Configuration A9

A magnetic sensor, comprising:

a first element including a first magnetic layer;

a second element including a second magnetic layer;

a first wire;

a second wire;

a first circuit electrically connected to the first wire and the second wire; and a second circuit electrically connected to the first element and the second element, the first circuit supplying a first alternating current to the first wire and supplying a second alternating current to the second wire, the second circuit supplying a first element current to the first element and supplying a second element current to the second element, in at least a portion of time, a phase of the first alternating current being the reverse of a phase of the second alternating current in an orientation of an external magnetic field applied to the first element and the second element.

Configuration A10

The magnetic sensor according to any one of Configurations A1 to A9, further comprising:

a first magnetic part;

a first nonmagnetic region provided between the first magnetic part and the first element;

a second magnetic part; and a second nonmagnetic region provided between the second magnetic part and the second element.

Configuration A11

A magnetic sensor, comprising:

a first element including a first magnetic layer;

a second element including a second magnetic layer;

a third element including a third magnetic layer;

a fourth element including a fourth magnetic layer;

first to fourth wires;

a first circuit electrically connected to the first to fourth wires; and a second circuit electrically connected to the first to fourth elements, the first circuit supplying first to fourth alternating currents respectively to the first to fourth wires, the second circuit supplying first to fourth element currents respectively to the first to fourth elements, at a first time, the first to fourth alternating currents respectively having first to fourth alternating current orientations, at a second time, the first to fourth alternating currents respectively having reverse orientations of the first to fourth alternating current orientations, at the first time, the first to fourth element currents having first to fourth element current orientations, at the second time, the first to fourth element currents having the first to fourth element current orientations, the first alternating current orientation having a component in an orientation of the first element current, the second alternating current orientation having a component in a reverse orientation of an orientation of the second element current, the third alternating current orientation having a component in an orientation of the third element current, the fourth alternating current orientation having a component in a reverse orientation of an orientation of the fourth element current.

Configuration A12

The magnetic sensor according to Configuration A11, wherein a distance between the first wire and the first element is shorter than a distance between the first wire and the second element, shorter than a distance between the first wire and the third element, and shorter than a distance between the first wire and the fourth element, a distance between the second wire and the second element is shorter than a distance between the second wire and the first element, shorter than a distance between the second wire and the third element, and shorter than a distance between the second wire and the fourth element, a distance between the third wire and the third element is shorter than a distance between the third wire and the first element, shorter than a distance between the third wire and the second element, and shorter than a distance between the third wire and the fourth element, a distance between the fourth wire and the fourth element is shorter than a distance between the fourth wire and the first element, shorter than a distance between the fourth wire and the second element, and shorter than a distance between the fourth wire and the third element, the first wire includes a first wire end portion and a second wire end portion, the second wire includes a third wire end portion and a fourth wire end portion, the third wire includes a fifth wire end portion and a sixth wire end portion, the fourth wire includes a seventh wire end portion and an eighth wire end portion, an orientation from the third wire end portion toward the fourth wire end portion is along an orientation from the first wire end portion toward the second wire end portion, an orientation from the seventh wire end portion toward the eighth wire end portion is along an orientation from the fifth wire end portion toward the sixth wire end portion, the orientation from the seventh wire end portion toward the eighth wire end portion is along the orientation from the first wire end portion toward the second wire end portion, at the first time, the first alternating current has the orientation from the first wire end portion toward the second wire end portion, at the first time, the second alternating current has an orientation from the fourth wire end portion toward the third wire end portion, at the first time, the third alternating current has the orientation from the fifth wire end portion toward the sixth wire end portion, and at the first time, the fourth alternating current has an orientation from the eighth wire end portion toward the seventh wire end portion.

Configuration A13

The magnetic sensor according to Configuration A12, wherein the first element and the second element are electrically connected in series, and the fourth element and the third element are electrically connected in series.

Configuration A14

The magnetic sensor according to Configuration A13, wherein the first element includes a first element end portion and a second element end portion, the second element includes a third element end portion and a fourth element end portion, the third element includes a fifth element end portion and a sixth element end portion, the fourth element includes a seventh element end portion and an eighth element end portion, the first element end portion and the seventh element end portion are electrically connected to each other, the fourth element end portion and the sixth element end portion are electrically connected to each other, the second element end portion and the third element end portion are electrically connected to each other, the eighth element end portion and the fifth element end portion are electrically connected to each other, and the second circuit is electrically connected to the first element end portion, the seventh element end portion, the fourth element end portion, and the sixth element end portion.

Configuration A15

The magnetic sensor according to Configuration A14, further comprising a third circuit, the third circuit outputting a signal corresponding to a difference between a potential of the second element end portion and a potential of the eighth element end portion.

Configuration A16

The magnetic sensor according to any one of Configurations A11 to A15, wherein the third element further includes a third counter magnetic layer, and a third nonmagnetic layer provided between the third magnetic layer and the third counter magnetic layer, and the fourth element further includes a fourth counter magnetic layer, and a fourth nonmagnetic layer provided between the fourth magnetic layer and the fourth counter magnetic layer.

Configuration A17

The magnetic sensor according to Configuration A16, wherein a length of the third magnetic layer along a third magnetic layer direction is longer than a length of the third magnetic layer along a third magnetic layer cross direction, the third magnetic layer direction crossing a third stacking direction from the third counter magnetic layer toward the third magnetic layer, the third magnetic layer cross direction crossing a plane including the third stacking direction and the third magnetic layer direction, and a length of the fourth magnetic layer along a fourth magnetic layer direction is longer than a length of the fourth magnetic layer along a fourth magnetic layer cross direction, the fourth magnetic layer direction crossing a fourth stacking direction from the fourth counter magnetic layer toward the fourth magnetic layer, the fourth magnetic layer cross direction crossing a plane including the fourth stacking direction and the fourth magnetic layer direction.

Configuration A18

The magnetic sensor according to any one of Configurations A1 to A17, wherein the first element further includes a first counter magnetic layer, and a first nonmagnetic layer provided between the first magnetic layer and the first counter magnetic layer, and the second element further includes a second counter magnetic layer, and a second nonmagnetic layer provided between the second magnetic layer and the second counter magnetic layer.

Configuration A19

The magnetic sensor according to Configuration A18, wherein a length of the first magnetic layer along a first magnetic layer direction is longer than a length of the first magnetic layer along a first magnetic layer cross direction, the first magnetic layer direction crossing a first stacking direction from the first counter magnetic layer toward the first magnetic layer, the first magnetic layer cross direction crossing a plane including the first stacking direction and the first magnetic layer direction, and a length of the second magnetic layer along a second magnetic layer direction is longer than a length of the second magnetic layer along a second magnetic layer cross direction, the second magnetic layer direction crossing a second stacking direction from the second counter magnetic layer toward the second magnetic layer, the second magnetic layer cross direction crossing a plane including the second stacking direction and the second magnetic layer direction.

Configuration A20

The magnetic sensor according to any one of Configurations A1 to A19, wherein an electrical resistance of the first element has an even-function characteristic of a magnetic field applied to the first element, and an electrical resistance of the second element has an even-function characteristic of a magnetic field applied to the second element.

Configuration A21 a diagnostic device, comprising:

the magnetic sensor according to any one of Configurations A1 to A20; and a processor processing a signal obtained from the magnetic sensor.

Figure 28A:
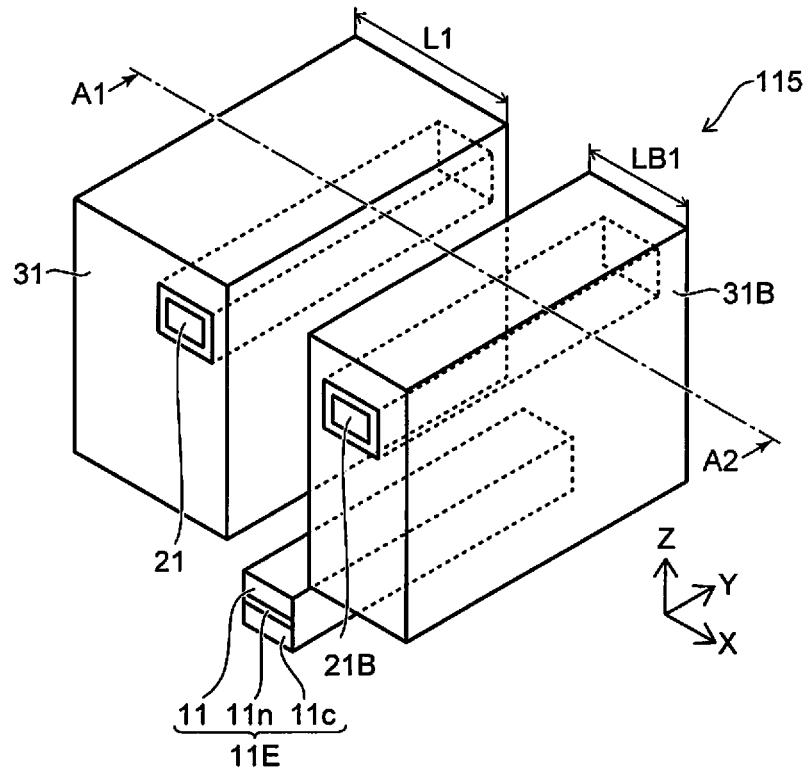
FIG. 28A and FIG. 28B are schematic views illustrating a magnetic sensor according to a first embodiment.
Figure 28B:
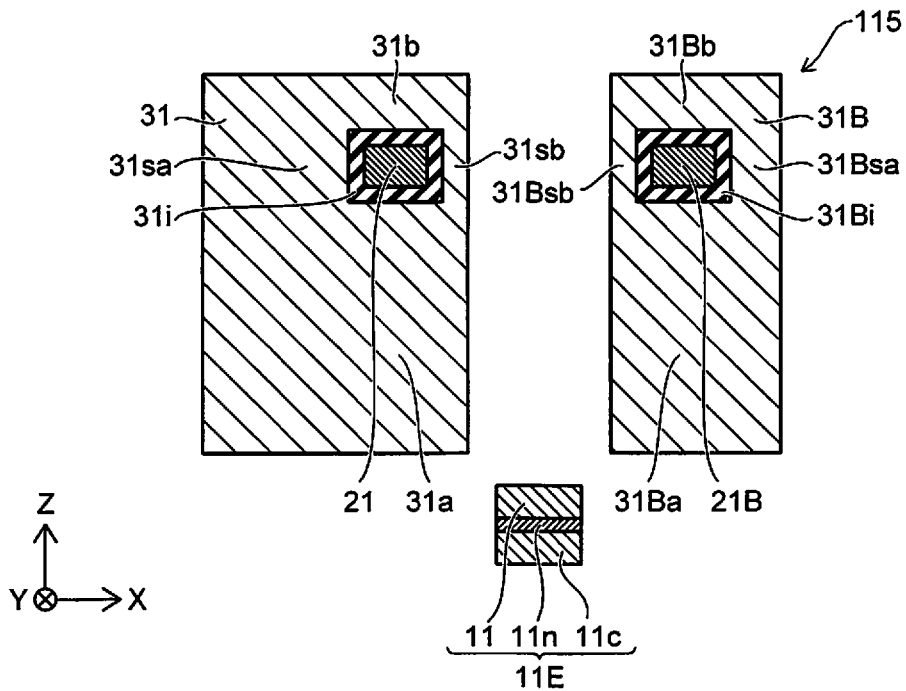

FIG. 28A and FIG. 28B are schematic views illustrating a magnetic sensor according to a first embodiment.

FIG. 28A is a perspective view. FIG. 28B is a line A1-A2 cross-sectional view of FIG. 1A.

As shown in FIG. 28A, the magnetic sensor 115 according to the embodiment includes a first element 11E, a first wire 21, and a first magnetic part 31. As shown in FIG. 28A and FIG. 28B, in the magnetic sensor 115, the first element 11E does not overlap the first magnetic part 31 in a third direction (X-axis direction) crossing a plane including the first direction and the second direction. In the third direction, the first element 11E does not overlap the first wire 21. Except such the disposition of the element, the descriptions for the magnetic sensor 110 can be are applied to the magnetic sensor 115. In the magnetic sensor 115 as well, a magnetic sensor can be provided in which the detection sensitivity can be increased.

According to the embodiments, a magnetic sensor, a sensor module, and a diagnostic device can be provided in which the detection sensitivity can be increased.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in magnetic sensors such as elements, magnetic layers, nonmagnetic layers, wires, resistance parts, circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors, sensor modules, and diagnostic devices practicable by an appropriate design modification by one skilled in the art based on the magnetic sensors, the sensor modules, and the diagnostic devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A magnetic sensor, comprising:
   a first element including a first magnetic layer, a first counter magnetic layer, and a first nonmagnetic layer provided between the first magnetic layer and the first counter magnetic layer, a direction from the first counter magnetic layer toward the first magnetic layer being along a first direction;
   a first wire extending in a second direction crossing the first direction;
   a first magnetic part including a first region and a first counter region, at least a portion of the first wire being between the first region and the first counter region in the first direction;
   a first side wire extending in the second direction; and
   a first side magnetic part,
   the first side magnetic part including a first region of the first side magnetic part and a first counter region of the first side magnetic part,
   at least a portion of the first side wire being between the first region of the first side magnetic part and the first counter region of the first side magnetic part in the first direction,
   a position of the first element in a third direction being between a position in the third direction of the first wire and a position in the third direction of the first side wire, the third direction being from the first region toward the first element,
   wherein a length along the third direction of the first magnetic part is longer than a length along the third direction of the first side magnetic part.

2. The sensor according to claim 1, further comprising a first circuit,
   the first wire including a first end portion of the first wire and a first other end portion of the first wire, a direction from the first end portion of the first wire toward the first other end portion of the first wire being along the second direction,
   the first side wire including a first end portion of the first side wire and a first other end portion of the first side wire, a direction from the first end portion of the first side wire toward the first other end portion of the first side wire being along the second direction,
   a direction from the first end portion of the first wire toward the first end portion of the first side wire being along the third direction,
   a direction from the first other end portion of the first wire toward the first other end portion of the first side wire being along the third direction,
   the first end portion of the first wire and the first end portion of the first side wire being electrically connected to each other,
   the first other end portion of the first wire and the first other end portion of the first side wire being electrically connected to each other,
   the first circuit being electrically connected to the first end portion of the first wire and the first other end portion of the first wire and supplying an alternating current to the first wire and the first side wire.

3. The sensor according to claim 1, further comprising:
   a second element;
   a second wire; and
   a second magnetic part,
   the second element including a second magnetic layer, a second counter magnetic layer, and a second nonmagnetic layer provided between the second magnetic layer and the second counter magnetic layer, a direction from the second counter magnetic layer toward the second magnetic layer being along the first direction,
   the second wire extending in the second direction,
   the second magnetic part including a second region and a second counter region, at least a portion of the second wire being between the second region and the second counter region in the first direction.

4. The sensor according to claim 3, further comprising:
a second side wire extending in the second direction; and
a second side magnetic part,
the second side magnetic part including a second region of the second side magnetic part and a second side region of the second side magnetic part,
at least a portion of the second side wire being between the second region of the second side magnetic part and the second side region of the second side magnetic part in the first direction,
a position in the third direction of the second element being between a position in the third direction of the second wire and a position in the third direction of the second side wire.

5. The sensor according to claim 3, further comprising a first circuit,
the first wire including a first end portion of the first wire and a first other end portion of the first wire, a direction from the first end portion of the first wire toward the first other end portion of the first wire being along the second direction,
a first side wire including a first end portion of the first side wire and a first other end portion of the first side wire, a direction from the first end portion of the first side wire toward the first other end portion of the first side wire being along the second direction,
a direction from the first end portion of the first wire toward the first end portion of the first side wire being along the third direction,
a direction from the first other end portion of the first wire toward the first other end portion of the first side wire being along the third direction,
the first end portion of the first wire and the first end portion of the first side wire being electrically connected to each other,
the first other end portion of the first wire and the first other end portion of the first side wire being electrically connected to each other,
the second wire including a second end portion of the second wire and a second other end portion of the second wire, a direction from the second end portion of the second wire toward the second other end portion of the second wire being along the second direction,
the second side wire including a second end portion of the second side wire and a second other end portion of the second side wire, a direction from the second end portion of the second side wire toward the second other end portion of the second side wire being along the second direction,
a direction from the second end portion of the second side wire toward the second end portion of the second wire being along the third direction,
a direction from the second other end portion of the second side wire toward the second other end portion of the second wire being along the third direction,
the second end portion of the second wire and the second end portion of the second side wire being electrically connected to each other,
the second other end portion of the second wire and the second other end portion of the second side wire being electrically connected to each other,
the second end portion of the second wire being electrically connected to the first end portion of the first wire,
the first circuit being electrically connected to the first other end portion of the first wire and the second other end portion of the second wire and supplying an alternating current to the first wire, the first side wire, the second wire, and the second side wire.

6. The sensor according to claim 5, further comprising:
a third element;
a fourth element;
a third wire;
a fourth wire;
a third magnetic part; and
a fourth magnetic part,
the third element including a third magnetic layer, a third counter magnetic layer, and a third nonmagnetic layer provided between the third magnetic layer and the third counter magnetic layer, a direction from the third counter magnetic layer toward the third magnetic layer being along the first direction,
the third wire extending in the second direction,
the third magnetic part including a third region and a third counter region, at least a portion of the third wire being between the third region and the third counter region in the first direction,
the fourth element including a fourth magnetic layer, a fourth counter magnetic layer, and a fourth nonmagnetic layer provided between the fourth magnetic layer and the fourth counter magnetic layer, a direction from the fourth counter magnetic layer toward the fourth magnetic layer being along the first direction,
the fourth wire extending in the second direction,
the fourth magnetic part including a fourth region and a fourth counter region, at least a portion of the fourth wire being between the fourth region and the fourth counter region in the first direction,
the third wire including a third end portion of the third wire and a third other end portion of the third wire, a direction from the third end portion of the third wire toward the third other end portion of the third wire being along the second direction,
the fourth wire including a fourth end portion of the fourth wire and a fourth other end portion of the fourth wire, a direction from the fourth end portion of the fourth wire toward the fourth other end portion of the fourth wire being along the second direction,
the third other end portion of the third wire being electrically connected to the fourth other end portion of the fourth wire,
the third end portion of the third wire being electrically connected to the first other end portion of the first wire,
the fourth end portion of the fourth wire being electrically connected to the second other end portion of the second wire.

7. A sensor module, comprising:
the magnetic sensor according to claim 1; and
a first circuit,
the first circuit being electrically connected to the first wire and supplying an alternating current to the first wire.

8. A diagnostic device, comprising:
the magnetic sensor according to claim 1; and
a processor processing a signal obtained from the magnetic sensor.

9. A magnetic sensor, comprising:
a first element including a first magnetic layer, a first counter magnetic layer, and a first nonmagnetic layer provided between the first magnetic layer and the first counter magnetic layer, a direction from the first counter magnetic layer toward the first magnetic layer being along a first direction;

a first wire extending in a second direction crossing the first direction;
a first counter wire extending in the second direction; and
a first magnetic part provided between the first wire and the first counter wire in the first direction; and
a first circuit,
the first wire including a first end portion of the first wire and a first other end portion of the first wire, a direction from the first end portion of the first wire toward the first other end portion of the first wire being along the second direction,
the first counter wire including a first end portion of the first counter wire and a first other end portion of the first counter wire, a direction from the first end portion of the first counter wire toward the first other end portion of the first counter wire being along the second direction,
a direction from the first end portion of the first counter wire toward the first end portion of the first wire being along the first direction,
a direction from the first other end portion of the first counter wire toward the first other end portion of the first wire being along the first direction,
at a first time, the first circuit setting a potential of the first end portion of the first wire to be lower than a potential of the first other end portion of the first wire and setting a potential of the first end portion of the first counter wire to be higher than a potential of the first other end portion of the first counter wire,
at a second time, the first circuit setting the potential of the first end portion of the first wire to be higher than the potential of the first other end portion of the first wire and setting the potential of the first end portion of the first counter wire to be lower than the potential of the first other end portion of the first counter wire.

10. The sensor according to claim 9, further comprising:
a second element;
a second wire;
a second counter wire; and
a second magnetic part,
the second element including a second magnetic layer, a second counter magnetic layer, and a second nonmagnetic layer provided between the second magnetic layer and the second counter magnetic layer, a direction from the second counter magnetic layer toward the second magnetic layer being along the first direction,
the second wire extending in the second direction,
the second counter wire extending in the second direction,
the second magnetic part being provided between the second wire and the second counter wire in the first direction,
the second wire including a second end portion of the second wire and a second other end portion of the second wire, a direction from the second end portion of the second wire toward the second other end portion of the second wire being along the second direction,
the second counter wire including a second end portion of the second counter wire and a second other end portion of the second counter wire, a direction from the second end portion of the second counter wire toward the second other end portion of the second counter wire being along the second direction,
a direction from the second end portion of the second counter wire toward the second end portion of the second wire being along the first direction,
a direction from the second other end portion of the second counter wire toward the second other end portion of the second wire being along the first direction,
at the first time, the first circuit setting a potential of the second end portion of the second wire to be higher than a potential of the second other end portion of the second wire and setting a potential of the second end portion of the second counter wire to be lower than a potential of the second other end portion of the second counter wire,
at the second time, the first circuit setting the potential of the second end portion of the second wire to be lower than the potential of the second other end portion of the second wire and setting the potential of the second end portion of the second counter wire to be higher than the potential of the second other end portion of the second counter wire.

11. A sensor module, comprising:
the magnetic sensor according to claim 9; and
a first circuit,
the first circuit being electrically connected to the first wire and the first counter wire and supplying an alternating current to the first wire and the first counter wire.

12. A magnetic sensor, comprising:
a first element including a first magnetic layer, a first counter magnetic layer, and a first nonmagnetic layer provided between the first magnetic layer and the first counter magnetic layer, a direction from the first counter magnetic layer toward the first magnetic layer being along a first direction;
a first wire extending in a second direction crossing the first direction;
a first magnetic part including a first region and a first counter region, at least a portion of the first wire being between the first region and the first counter region in the first direction; and
an insulating member being provided between the first wire and the first magnetic part, the insulating member physically contacting the first wire and the first magnetic part,
wherein the insulating member surrounds the first wire, and the first magnetic part surrounds the insulating member.

13. The sensor according to claim 12, wherein
a part of the insulating member is provided between the first region and at least a part of the first wire, and physically contacts the first region and the at least the part of the first wire, and
another part of the insulating member is provided between the first counter region and the at least the part of the first wire, and physically contacts the counter first region and the at least the part of the first wire.

14. A magnetic sensor, comprising:
a first element including a first magnetic layer, a first counter magnetic layer, and a first nonmagnetic layer provided between the first magnetic layer and the first counter magnetic layer, a direction from the first counter magnetic layer toward the first magnetic layer being along a first direction;
a first wire extending in a second direction crossing the first direction;
a first magnetic part including a first region and a first counter region, at least a portion of the first wire being between the first region and the first counter region in the first direction, the first magnetic part including at least one selected from the group consisting of a NiFe alloy, an FeCo alloy, and a CoZrNb alloy; and
an insulating member,
wherein the insulating member surrounds the first wire, and the first magnetic part surrounds the insulating member.

* * * * *